US007439039B2

(12) United States Patent
Blakely et al.

(10) Patent No.: US 7,439,039 B2
(45) Date of Patent: Oct. 21, 2008

(54) ASSAYS FOR NOVEL SEROTONIN TRANSPORTER (SERT) BLOCKERS

(75) Inventors: Randy D. Blakely, Brentwood, TN (US); Loren Keith Henry, Mount Juliet, TN (US); Erika M. Adkins, Layton, UT (US)

(73) Assignee: Vanderbilt University, Nashville, TN (US)

( * ) Notice: Subject to any disclaimer, the term of this patent is extended or adjusted under 35 U.S.C. 154(b) by 189 days.

(21) Appl. No.: 10/884,194

(22) Filed: Jul. 2, 2004

(65) Prior Publication Data

US 2005/0107299 A1 May 19, 2005

Related U.S. Application Data

(60) Provisional application No. 60/531,816, filed on Dec. 22, 2003, provisional application No. 60/485,261, filed on Jul. 3, 2003.

(51) Int. Cl.

| | |
|---|---|
| ***C12P 21/06*** | (2006.01) |
| ***C12P 1/00*** | (2006.01) |
| ***C12N 1/12*** | (2006.01) |
| ***C12N 15/00*** | (2006.01) |
| ***Q01N 33/53*** | (2006.01) |
| ***C07N 21/02*** | (2006.01) |

(52) U.S. Cl. ................ 435/69.1; 435/252.3; 435/320.1; 435/7.1; 435/7.2; 435/7.21; 536/23.1; 530/350

(58) Field of Classification Search ....................... None
See application file for complete search history.

(56) References Cited

U.S. PATENT DOCUMENTS

| | | | | |
|---|---|---|---|---|
| 5,418,162 | A | 5/1995 | Blakely et al. | 435/252.3 |
| 5,552,308 | A | 9/1996 | Hoffman et al. | 435/172.3 |
| 5,919,797 | A | 7/1999 | Goodman et al. | 514/319 |
| 6,165,716 | A | 12/2000 | Battersby et al. | 435/6 |
| 2002/0142312 | A1 | 10/2002 | Cigler et al. | 435/6 |
| 2003/0051266 | A1 | 3/2003 | Serafini | 800/18 |

FOREIGN PATENT DOCUMENTS

| | | |
|---|---|---|
| WO | WO 93/08261 | 4/1993 |
| WO | WO 97/11175 | 3/1997 |
| WO | WO 02/076204 | 10/2002 |

OTHER PUBLICATIONS

Adkins et al., "Interactions of tryptamine derivatives with serotonin transporter species variants implicate transmembrane domain I in substrate recognition," (abstract), *Molecular Pharmacology*, 59(3):514-523, 2001.

Barker and Blakeley, "Identification of a single amino-acid, phenylalanine-586, that is responsible for high-affinity interactions of tricyclic antidepressants with the human serotonin transporter," (abstract), *Molecular Pharmacology*, 50(4):957-965, 1996.

Barker et al., "High affinity recognition of serotonin transporter antagonists defined by species-scanning mutagenesis. An aromatic residue in transmembrane domain I dictates species-selective recognition of citalopram and mazindol," (abstract), *J. Biol. Chem.*, 273(31):19459-19468, 1998.

Barker et al., "Transmembrane domain I contributes to the permeation pathway for serotonin and ions in the serotonin transporter," (abstract), *J. Neurosci.*, 19(12):4705-4717, 1999.

Blakely and Bauman, "Biogenic amine transporters: regulation in flux," (abstract), *Curr. Opin. Neurobiol.*, 10(3):328-336, 2000.

Ewald et al., "A functional variant of the serotonin transporter gene in families with bipolar affective disorder," (abstract), *J. Affective Disorders*, 48/2-3:134-144, 1998.

Guterrez et al., "Variability in the serotonin transporter gene and increased risk for major depression with melancholia," (abstract), *Hum Genet.*, 103(3):319-322, 1998.

Henry et al., "Serotonin and cocaine-sensitive inactivation of human serotonin transporters by methanethiosulfonates targeted to transmembrane domain I," *J. Biol. Chem.*, 278(39):37052-37063, 2003.

Holmes et al., "Evaluation of antidepressant-related behavioral responses in mice lacking the serotonin transporter," (abstract), *Neuropsychopharmacology*, 27(6):914-923, 2002.

Lin et al., "Single-channel currents produced by the serotonin transporter and analysis of a mutation affecting ion permeation," (abstract), *Biophysical Journal*, 71(6):3126-3135, 1996.

Minov et al., "Serotonin-2A-receptor and -transporter polymorphisms: lack of association in patients with major depression," (abstract), *Neuroscience Letters*, 303(2):119-122, 2001.

Mortensen et al., "Species-scanning mutagenesis of the serotonin transporter reveals residues essential in selective, high-affinity recognition of antidepressants," (abstract), *J. Neurochemistry*, 79(2):237-247, 2001.

Penado et al., "Critical amino acid residues in transmembrane span 7 of the serotonin transporter identified by random mutagenesis," (abstract), *J. Biol. Chem.*, 273(43):28098-28106, 1998.

Ranganathan et al., "Mutations in the Caenorhabditis elegans serotonin reuptake transporter MOD-5 reveal serotonin-dependent and -independent activities of fluoxetine," (abstract), *J. Neurosci.*, 21(16):5871-5884, 2001.

Roman et al., "Identification of serotonin transporter domains involved in the molecular recognition of cocaine and amphetamine," (abstract), Society for Neuroscience Abstracts, 27(2):2154, 2001.

Sandhu et al., "A cocaine insensitive chimeric insect serotonin," (abstract), *European J. Biochem.*, 269(16):3934-3944, 2002.

(Continued)

*Primary Examiner*—Olga N Chernyshev
(74) *Attorney, Agent, or Firm*—Fulbright & Jaworski, LLP

(57) ABSTRACT

The serotonin transporter (SERT) is a target of various therapeutic agents used in the treatment of neurological and neurodegenerative disorders. The present invention provides novel forms of SERT that lacks high affinity recognition of specific serotonin reuptake inhibitors (SSRIs). The present invention therefore provides a novel target for use in screening and model development that can aid both the discovery of new medications and the discovery of novel pathways impacted in parallel with SERT blockade. Such novel targets can help identify new SSRI's with unique modifications and lead to discovery of pathways that secondarily support the therapeutic activity of these agents.

25 Claims, 4 Drawing Sheets

OTHER PUBLICATIONS

Serretti et al., "Genetics of the response to antidepressants in mood disorders," *Giornale Italiano di Psicopatologia*, 7/3:244-258, 2001.
Shen et al., "Refined mapping of the human serotonin transporter," (abstract), *Eur. J. Human Genetics*, 8(1):75-78, 2000.
Smicun et al., "The role of external loop regionsi n serotonin transport-loop scanning mutagenesis of the serotonin transporter external domain," (abstract), *J. Biol. Chem.*, 274(51):36058-36064, 1999.
Sur et al., "A single serine residue controls the caption dependence of substrate transport by the rat serotonin transporter," (abstract), *Proc. Natl. Acad. Sci., USA*, 94(14):7639-7644, 1997.
Sur et al., "The rat serotonin transporter: identification of cysteine residues important for substrate transport," (abstract), *Biochemical and Biophysical Research Communications*, 241(1):68-72, 1997.
Chen and Rudnick, "Permeation and gating residues in serotonin transporter," *Proc. Natl. Acad. Sci., USA*, 97(3):1044-1049, 2000.
Chen et al., "The third transmembrane domain of the serotonin transporter contains residues associated with substrate and cocaine binding," *J. Biol. Chem.*, 272(45):28321-28327, 1997.
Henry et al., "Identification of mutant serotonin transporters lacking high-affinity antidepressant interactions," *33rd Annual Meeting of the Society of Neuroscience*, Abstract No. 337.7, New Orleans, LA, Nov. 8-12, 2003.
Ramamoorthy et al., "Antidepressant- and cocaine-sensitive human serotonin transporter: molecular cloning, expression, and chromosomal localization," *Proc. Natl. Acad. Sci., USA*, 90:2542-2546, 1993.
Rudnick et al., "The third transmembrane domain of the serotonin transporter contains residues associated with substrate and cocaine binding," *Society for Neuroscience Abstracts*, 23(1-2):404, 1997.
Schloss and Williams, "The serotonin transporter: a primary target for antidepressant drugs," *Journal of Psychopharmacology*, 12(2):115-121, 1998.

human serotonin transporter (I172M)

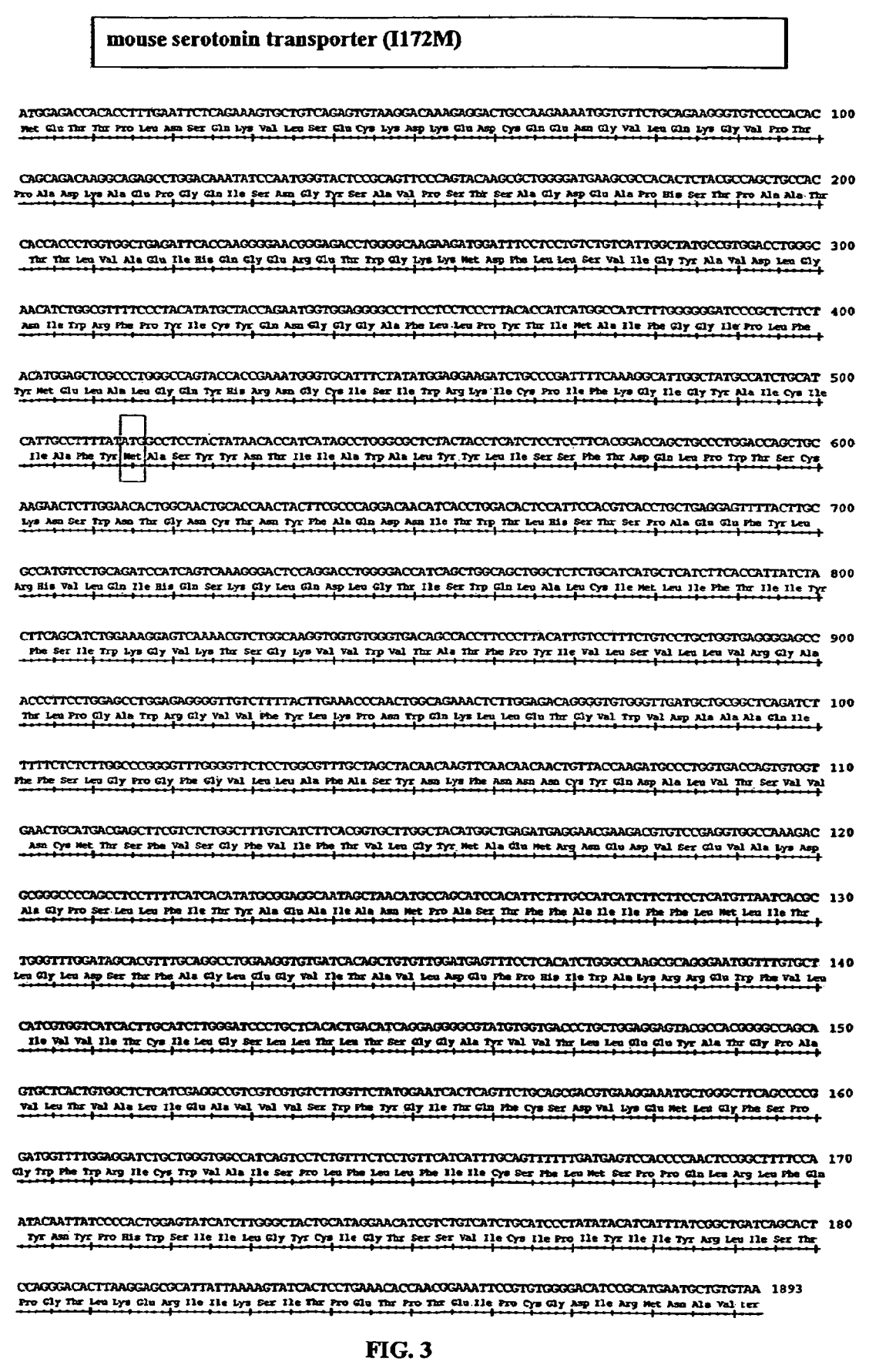

mouse serotonin transporter (I172M)

ATGGAGACCACACCTTTGAATTCTCAGAAAGTGCTGTCAGAGTGTAAGGACAAAGAGGACTGCCAAGAAAATGGTGTTCTGCAGAAGGGTGTCCCCACAC 100
Met Glu Thr Thr Pro Leu Asn Ser Gln Lys Val Leu Ser Glu Cys Lys Asp Lys Glu Asp Cys Gln Glu Asn Gly Val Leu Gln Lys Gly Val Pro Thr

CAGCAGACAAGGCAGAGCCTGGACAAATATCCAATGGGTACTCCGCAGTTCCCAGTACAAGCGCTGGGGATGAAGCGCCACACTCTACGCCAGCTGCCAC 200
Pro Ala Asp Lys Ala Glu Pro Gly Gln Ile Ser Asn Gly Tyr Ser Ala Val Pro Ser Thr Ser Ala Gly Asp Glu Ala Pro His Ser Thr Pro Ala Ala Thr

CACCACCCTGGTGGCTGAGATTCACCAAGGGGAACGGGAGACCTGGGGCAAGAAGATGGATTTCCTCCTGTCTGTCATTGGCTATGCCGTGGACCTGGGC 300
Thr Thr Leu Val Ala Glu Ile His Gln Gly Glu Arg Glu Thr Trp Gly Lys Lys Met Asp Phe Leu Leu Ser Val Ile Gly Tyr Ala Val Asp Leu Gly

AACATCTGGCGTTTTCCCTACATATGCTACCAGAATGGTGGAGGGGCCTTCCTCCTCCCTTACACCATCATGGCCATCTTTGGGGGGATCCCGCTCTTCT 400
Asn Ile Trp Arg Phe Pro Tyr Ile Cys Tyr Gln Asn Gly Gly Gly Ala Phe Leu Leu Pro Tyr Thr Ile Met Ala Ile Phe Gly Gly Ile Pro Leu Phe

ACATGGAGCTCGCCCTGGGCCAGTACCACCGAAATGGGTGCATTTCTATATGGAGGAAGATCTGCCCGATTTTCAAAGGCATTGGCTATGCCATCTGCAT 500
Tyr Met Glu Leu Ala Leu Gly Gln Tyr His Arg Asn Gly Cys Ile Ser Ile Trp Arg Lys Ile Cys Pro Ile Phe Lys Gly Ile Gly Tyr Ala Ile Cys Ile

CATTGCCTTTTATATGGCCTCCTACTATAACACCATCATAGCCTGGGCGCTCTACTACCTCATCTCCTCCTTCACGGACCAGCTGCCCTGGACCAGCTGC 600
Ile Ala Phe Tyr Met Ala Ser Tyr Tyr Asn Thr Ile Ile Ala Trp Ala Leu Tyr Tyr Leu Ile Ser Ser Phe Thr Asp Gln Leu Pro Trp Thr Ser Cys

AAGAACTCTTGGAACACTGGCAACTGCACCAACTACTTCGCCCAGGACAACATCACCTGGACACTCCATTCCACGTCACCTGCTGAGGAGTTTTACTTGC 700
Lys Asn Ser Trp Asn Thr Gly Asn Cys Thr Asn Tyr Phe Ala Gln Asp Asn Ile Thr Trp Thr Leu His Ser Thr Ser Pro Ala Glu Glu Phe Tyr Leu

GCCATGTCCTGCAGATCCATCAGTCAAAGGGACTCCAGGACCTGGGGACCATCAGCTGGCAGCTGGCTCTCTGCATCATGCTCATCTTCACCATTATCTA 800
Arg His Val Leu Gln Ile His Gln Ser Lys Gly Leu Gln Asp Leu Gly Thr Ile Ser Trp Gln Leu Ala Leu Cys Ile Met Leu Ile Phe Thr Ile Ile Tyr

CTTCAGCATCTGGAAAGGAGTCAAAACGTCTGGCAAGGTGGTGTGGGTGACAGCCACCTTCCCTTACATTGTCCTTTCTGTCCTGCTGGTGAGGGGAGCC 900
Phe Ser Ile Trp Lys Gly Val Lys Thr Ser Gly Lys Val Val Trp Val Thr Ala Thr Phe Pro Tyr Ile Val Leu Ser Val Leu Leu Val Arg Gly Ala

ACCCTTCCTGGAGCCTGGAGAGGGGTTGTCTTTTACTTGAAACCCAACTGGCAGAAACTCTTGGAGACAGGGGTGTGGGTTGATGCTGCGGCTCAGATCT 100
Thr Leu Pro Gly Ala Trp Arg Gly Val Val Phe Tyr Leu Lys Pro Asn Trp Gln Lys Leu Leu Glu Thr Gly Val Trp Val Asp Ala Ala Ala Gln Ile

TTTTCTCTCTTGGCCCCGGGTTTGGGGTTCTCCTGGCGTTTGCTAGCTACAACAAGTTCAACAACAACTGTTACCAAGATGCCCTGGTGACCAGTGTGGT 110
Phe Phe Ser Leu Gly Pro Gly Phe Gly Val Leu Leu Ala Phe Ala Ser Tyr Asn Lys Phe Asn Asn Asn Cys Tyr Gln Asp Ala Leu Val Thr Ser Val Val

GAACTGCATGACGAGCTTCGTCTCTGGCTTTGTCATCTTCACGGTGCTTGGCTACATGGCTGAGATGAGGAACGAAGACGTGTCCGAGGTGGCCAAAGAC 120
Asn Cys Met Thr Ser Phe Val Ser Gly Phe Val Ile Phe Thr Val Leu Gly Tyr Met Ala Glu Met Arg Asn Glu Asp Val Ser Glu Val Ala Lys Asp

GCGGGCCCCAGCCTCCTTTTCATCACATATGCGGAGGCAATAGCTAACATGCCAGCATCCACATTCTTTGCCATCATCTTCTTCCTCATGTTAATCACGC 130
Ala Gly Pro Ser Leu Leu Phe Ile Thr Tyr Ala Glu Ala Ile Ala Asn Met Pro Ala Ser Thr Phe Phe Ala Ile Ile Phe Phe Leu Met Leu Ile Thr

TGGGTTTGGATAGCACGTTTGCAGGCCTGGAAGGTGTGATCACAGCTGTGTTGGATGAGTTTCCTCACATCTGGGCCAAGCGCAGGGAATGGTTTGTGCT 140
Leu Gly Leu Asp Ser Thr Phe Ala Gly Leu Glu Gly Val Ile Thr Ala Val Leu Asp Glu Phe Pro His Ile Trp Ala Lys Arg Arg Glu Trp Phe Val Leu

CATCGTGGTCATCACTTGCATCTTGGGATCCCTGCTCACACTGACATCAGGAGGGGCGTATGTGGTGACCCTGCTGGAGGAGTACGCCACGGGGCCAGCA 150
Ile Val Val Ile Thr Cys Ile Leu Gly Ser Leu Leu Thr Leu Thr Ser Gly Gly Ala Tyr Val Val Thr Leu Leu Glu Glu Tyr Ala Thr Gly Pro Ala

GTGCTCACTGTGGCTCTCATCGAGGCCGTCGTCGTGTCTTGGTTCTATGGAATCACTCAGTTCTGCAGCGACGTGAAGGAAATGCTGGGCTTCAGCCCCG 160
Val Leu Thr Val Ala Leu Ile Glu Ala Val Val Val Ser Trp Phe Tyr Gly Ile Thr Gln Phe Cys Ser Asp Val Lys Glu Met Leu Gly Phe Ser Pro

GATGGTTTTGGAGGATCTGCTGGGTGGCCATCAGTCCTCTGTTTCTCCTGTTCATCATTTGCAGTTTTTTGATGAGTCCACCCCAACTCCGGCTTTTCCA 170
Gly Trp Phe Trp Arg Ile Cys Trp Val Ala Ile Ser Pro Leu Phe Leu Leu Phe Ile Ile Cys Ser Phe Leu Met Ser Pro Pro Gln Leu Arg Leu Phe Gln

ATACAATTATCCCCACTGGAGTATCATCTTGGGCTACTGCATAGGAACATCGTCTGTCATCTGCATCCCTATATACATCATTTATCGGCTGATCAGCACT 180
Tyr Asn Tyr Pro His Trp Ser Ile Ile Leu Gly Tyr Cys Ile Gly Thr Ser Ser Val Ile Cys Ile Pro Ile Tyr Ile Ile Tyr Arg Leu Ile Ser Thr

CCAGGGACACTTAAGGAGCGCATTATTAAAAGTATCACTCCTGAAACACCAACGGAAATTCCGTGTGGGGACATCCGCATGAATGCTGTGTAA 1893
Pro Gly Thr Leu Lys Glu Arg Ile Ile Lys Ser Ile Thr Pro Glu Thr Pro Thr Glu Ile Pro Cys Gly Asp Ile Arg Met Asn Ala Val ter

FIG. 3

ASSAYS FOR NOVEL SEROTONIN TRANSPORTER (SERT) BLOCKERS

The present application claims the benefit of the filing date of U.S. Provisional Patent Application Ser. No. 60/531,816, filed on Dec. 22, 2003 and U.S. Provisional Patent Application Ser. No. 60/485,261, filed on Jul. 3, 2003. The entire text of the above-referenced disclosures are specifically incorporated herein by reference without disclaimer.

The government owns rights in the present invention pursuant to grant numbers DA07390 and MH12399 from the National Institutes of Health.

BACKGROUND OF THE INVENTION

1. Field of the Invention

The present invention relates generally to the fields of neurobiology, pharmacology and psychiatry. More particularly, it concerns a screening method for identifying blockers or inhibitors of serotonin transport.

2. Description of Related Art

Neurotransmitters mediate signal transduction in the nervous system and modulate the processing of responses to a variety of sensory and physiological stimuli. An important regulatory step in neurotransmission is the inactivation of a neurotransmitter following its release into the synaptic cleft. This is especially true for the biogenic amine and amino acid neurotransmitters. Inactivation of neurotransmitters is typically mediated by uptake of the released neurotransmitter by neurotransmitters transporters that are located on the presynaptic neuron or in some cases on adjacent glial cells. Thus, neurotransmitter transporters are central to the processing of information in the nervous system and are associated with numerous neurological disorders.

For example, the neurotransmitter norepinephrine (also called noradrenalin) transduces signaling in the central nervous system that modulates attention, mood, arousal, learning, and memory (Aston-Jones et al., 1999; Coull et al., 1999; Skrebitsky and Chepkova, 1998; Hatfield and McGaugh, 1999). Norepinephrine (NE) transporters (NETs) attenuate neuronal signaling via rapid neurotransmitter clearance (Ressler and Nemeroff, 1999; Iversen et al., 1967; Axelrod and Kopin, 1969; Blakely et al., 1991). Norepinephrine transport is implicated in the pathology of major depression, post-traumatic stress disorder and attention deficit disorder (Ressler and Nemeroff, 1999; Southwick et al., 1999; Dow and Kline, 1997; Biederman and Spencer, 1999). Therapeutic agents that inhibit NET can elevate the concentration norepinephrine in the brain and periphery (Axelrod and Kopin, 1969; Bonisch, 1984; Ramamoorthy et al., 1993; Galli et al., 1995; Corey et al., 1994; Fleckenstein et al., 1999). Noradrenergic signaling in the peripheral nervous system influences blood pressure and heart rate (Jones, 1991; Jacob et al., 1999; Hartzell, 1980), and NET inhibitors, such as cocaine and antidepressants, induce cardiac complications (Watanabe et al., 1981; Clarkson et al., 1993; Glassman et al., 1985).

Similarly other neurotransmitters such as epinephrine (E), dopamine (DA), serotonin (SE), and their respective transporters such as epinephrine transporters (ET), dopamine transporters (DAT), and the serotonin transporters (SERT), mediate diverse aspects of neuronal signaling and are involved in the pathology of numerous nervous system related disorders. Thus, neurotransmitter transporters are the targets of various therapeutic agents used in the treatment of neurological disorders including, depression, epilepsy, schizophrenia, Parkinson's disease, attention deficit disorders, eating and sleeping disorders as well as some neurodegenerative disorders. In some instances, treatment of these disorders is mediated by the use of pharmaceutical agents that are antagonists of a neurotransmitter transporter. Antagonists block uptake and prolong and/or enhance the action of the neurotransmitter. For example, imipramine, a blocker of SE and NE uptake, is used as an antidepressant; benztropine, an antagonist of dopamine uptake, temporarily alleviates the symptoms of Parkinson's disease; and blockers of γ-amino butyric acid (GABA) uptake are used in the treatment of epilepsy.

Despite the relevance of neurotransmitter transporters, the art is hindered by very limited methods that are used in studying neurotransmitter transporter functions such as kinetics, affinity, temporal and spatial aspects of transport, voltage dependence and other transport mechanics (Galli et al., 1995; Corey et al., 1994; DeFelice and Galli, 1998; Prasad and Amara, 2001). Methods used to study neurotransmitter transport typically involve the use of radiometric substrates to measure neurotransmitter accumulation.

Unfortunately, traditional assays have made use of either native SERT or cloned SERT expressed in cells. These assays lack the ability assess whether the action of a drug is having its physiologic effect only by SERT blockade, even though it blocks the transporter in vitro or through other means as well. What is needed in the art is a novel form of SERT that lacks high affinity recognition of SSRIs to allow for discovery of novel drugs that block SERT in distinct ways and thus provide novel modes of action of SSRIs.

Thus, new methods for the analysis of neurotransmitter transport function are highly desirable in addition to cost effective and rapid screening methods to identify modulators of neurotransmitter transporters that may be useful as therapeutic agents in the treatment of nervous system disorders.

SUMMARY OF THE INVENTION

The deficiencies existing in the art include the inability to know if the action of a candidate neurotransmitter transport inhibitor is by SERT blockade, even though it blocks the transporter in vitro, or through some other mechanism. Thus, the ability to mask the affects of SERT blockade through known actions would permit the identification of new pathways of inhibition. To overcome these and other defects in the art, the present invention provides methods for the identification of novel serotonin transporter molecules for use in the screening of neutrotransmitter transporter inhibitors.

In particular embodiments of the present invention, novel serotonin transporter molecules that lack a conventional mode of antagonism, are identified and obtained. In a more particular embodiment, the present invention provides an isolated nucleic acid sequence encoding a serotonin transporter comprising the amino acid sequence of SEQ ID NO: 4, SEQ ID NO: 8, SEQ ID NO: 10, SEQ ID NO: 12, SEQ ID NO: 14, SEQ ID NO: 16, or SEQ ID NO: 18. The present invention further provides an isolated nucleic acid sequence encoding a serotonin transporter, further defined as having a nucleic acid sequence of SEQ ID NO: 3, SEQ ID NO: 7, SEQ ID NO: 9, SEQ ID NO: 11, SEQ ID NO: 13, SEQ ID NO: 15, or SEQ ID NO: 17. Such an isolated nucleic acid sequence may further be comprised in a vector, and may be operatively linked to a promoter that directs the expression of the nucleic acid in a cell. In particular embodiments, the promoter contemplated in the present invention is a serotonin transporter promoter.

The vector contemplated by the present invention may comprise a viral vector, such as but not limited to, an adenoviral vector, an adeno-associated viral vector, a retroviral vector, a lentiviral vector, a herpes viral vector, polyoma viral vector or hepatitis B viral vector.

In other particular embodiments, the present invention contemplates a host cell containing a nucleic acid sequence of SEQ ID NO: 3, SEQ ID NO: 7, SEQ ID NO: 9, SEQ ID NO: 11, SEQ ID NO: 13, SEQ ID NO: 15, or SEQ ID NO: 17. Such a host cell may be a mammalian cell which may include but is not limited to a human, mouse, rat, monkey, chicken, dog, cat, horse, pig, cow, sheep, goat, or hamster cell. It is further contemplated by the present invention that the host cell may be a neuronal cell or an insect cell. The host cell of the present invention may further comprise a vector.

In particular embodiments, the present invention provides a method of screening for a candidate substance that blocks serotonin transporter activity comprising (a) providing a cell or cell extract expressing a serotonin transporter having an amino acid sequence of SEQ ID NO: 4, SEQ ID NO: 8, SEQ ID NO: 10, SEQ ID NO: 12, SEQ ID NO: 14, SEQ ID NO: 16 or SEQ ID NO: 18; (b) exposing the cell or cell extract to a candidate substance; (c) measuring binding of the candidate substance to the serotonin transporter in step (a); and (d) comparing binding of the candidate substance by the serotonin transporter of step (a) to binding of the candidate substance by a serotonin transporter having an amino acid sequence of SEQ ID NO: 4, SEQ ID NO: 8, SEQ ID NO: 10, SEQ ID NO: 12, SEQ ID NO: 14, SEQ ID NO: 16, or SEQ ID NO: 18, wherein the ability of the candidate substance to bind to the serotonin transporter, but not the serotonin transporter having an amino acid sequence of SEQ ID NO: 2 or SEQ ID NO: 6, indicates that the candidate substance is a serotonin transporter blocking molecule.

In further particular embodiments, the present invention provides a method of measuring the transport of a candidate substance and comparing transport of the candidate substance by the serotonin transporter of SEQ ID NO: 4, SEQ ID NO: 8, SEQ ID NO: 10, SEQ ID NO: 12, SEQ ID NO: 14, SEQ ID NO: 16, or SEQ ID NO: 18 to transport of the candidate substance by a serotonin transporter having an amino acid sequence of SEQ ID NO: 4, SEQ ID NO: 8, SEQ ID NO: 10, SEQ ID NO: 12, SEQ ID NO: 14, SEQ ID NO: 16, or SEQ ID NO: 18 wherein the ability of the candidate substance to be transported by the serotonin transporter having the amino acid sequence of SEQ ID NO: 4, SEQ ID NO: 8, SEQ ID NO: 10, SEQ ID NO: 12, SEQ ID NO: 14, SEQ ID NO: 16, or SEQ ID NO: 18, but not the serotonin transporter having an amino acid sequence of SEQ ID NO: 2 or SEQ ID NO: 6, indicates that the candidate substance blocks serotonin transporter activity.

The cell or cell extract expressing a serotonin transporter having an amino acid sequence of SEQ ID NO: 4, SEQ ID NO: 8, SEQ ID NO: 10, SEQ ID NO: 12, SEQ ID NO: 14, SEQ ID NO: 16 or SEQ ID NO: 18, may be obtained from a mammalian cell or cell extract. The cell or cell extract may be a neuronal cell or cell extract.

Measuring the binding of the candidate substance to the serotonin transporter protein may comprise a radiolabeled substance such as but not limited to parotoxtine. It is further contemplated in the present invention that high-throughput screening of candidate substances may further comprise the use of a fluorescent plate reader. Candidate substances contemplated by the present invention include but are not limited to antidepressants, nucleic acid molecules, organic or inorganic small molecules, or organo-pharmaceuticals. The candidate substance may further comprise novel targets responsible for side-effects of specific serotonin re-uptake inhibitors (SSRI) and may be safer and more effective.

In particular embodiments of the invention, the candidate substance does not depend on isoleucine at position 172 of the amino acid sequence of SEQ ID NO: 4, SEQ ID NO: 8, SEQ ID NO: 10, SEQ ID NO: 12, SEQ ID NO: 14, SEQ ID NO: 16, or SEQ ID NO: 18.

In other particular embodiments, the present invention provides a method for treating a neurologic or psychiatric condition comprising administering to a subject in need thereof a therapeutically effective amount of a serotonin transporter blocker identified by the methods described above. Neurologic or psychiatric conditions that may be treated using a candidate substance of the invention include, but are not limited to, obsessive compulsive disorders (OCDs), autism, generalized anxiety disorders, pathological aggression, schizophrenia, schizotypal personality disorder, psychosis, a schizoaffective disorder, manic type disorder, a bipolar affective disorder, a bipolar affective (mood) disorder with hypomania and major depression (BP-II), a unipolar affective disorder, unipolar major depressive disorder, dysthymic disorder, a phobia, a panic disorder, a somatization disorder, hypochondriasis, or an attention deficit disorder. Administration of a candidate substance to a subject or patient may be done intravenously, intradermally, intramuscularly, precutaneously, subcutaneously, intraarterially, or by aerosol. The subject may be a mammal such as a human.

In still a further embodiment, the present invention provides a method of preparing a transgenic animal comprising introducing into the genome of an animal a transgene comprising a nucleic acid sequence encoding an amino acid sequence of SEQ ID NO: 4 or SEQ ID NO: 8 and a selectable marker under the control of a serotonin transporter promoter. The transgenic animal may be a rat, monkey, chicken, dog, cat, horse, pig, cow, sheep, goat, or hamster, but is not limited to such. In particular embodiments, the transgenic animal may be a transgenic mouse. The transgene may encode the nucleic acid sequence of SEQ ID NO: 3, SEQ ID NO: 7, SEQ ID NO: 9, SEQ ID NO: 11, SEQ ID NO: 13, SEQ ID NO: 15, or SEQ ID NO: 17. The transgenic animal of the present invention may express the amino acid sequence of SEQ ID NO: 4, SEQ ID NO: 8, SEQ ID NO: 10, SEQ ID NO: 12, SEQ ID NO: 14, SEQ ID NO: 16, or SEQ ID NO: 18.

It is contemplated that any method or composition described herein can be implemented with respect to any other method or composition described herein.

The use of the word, "a" or "an" when used with the term "comprising" in the specification and/or claims may mean "one", "one or more", "at least one", or "one or more than one".

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 3—I172M mouse serotonin transporter (SEQ ID NOS:3-4).

DESCRIPTION OF ILLUSTRATIVE EMBODIMENTS

I. The Present Invention

Figure 1:
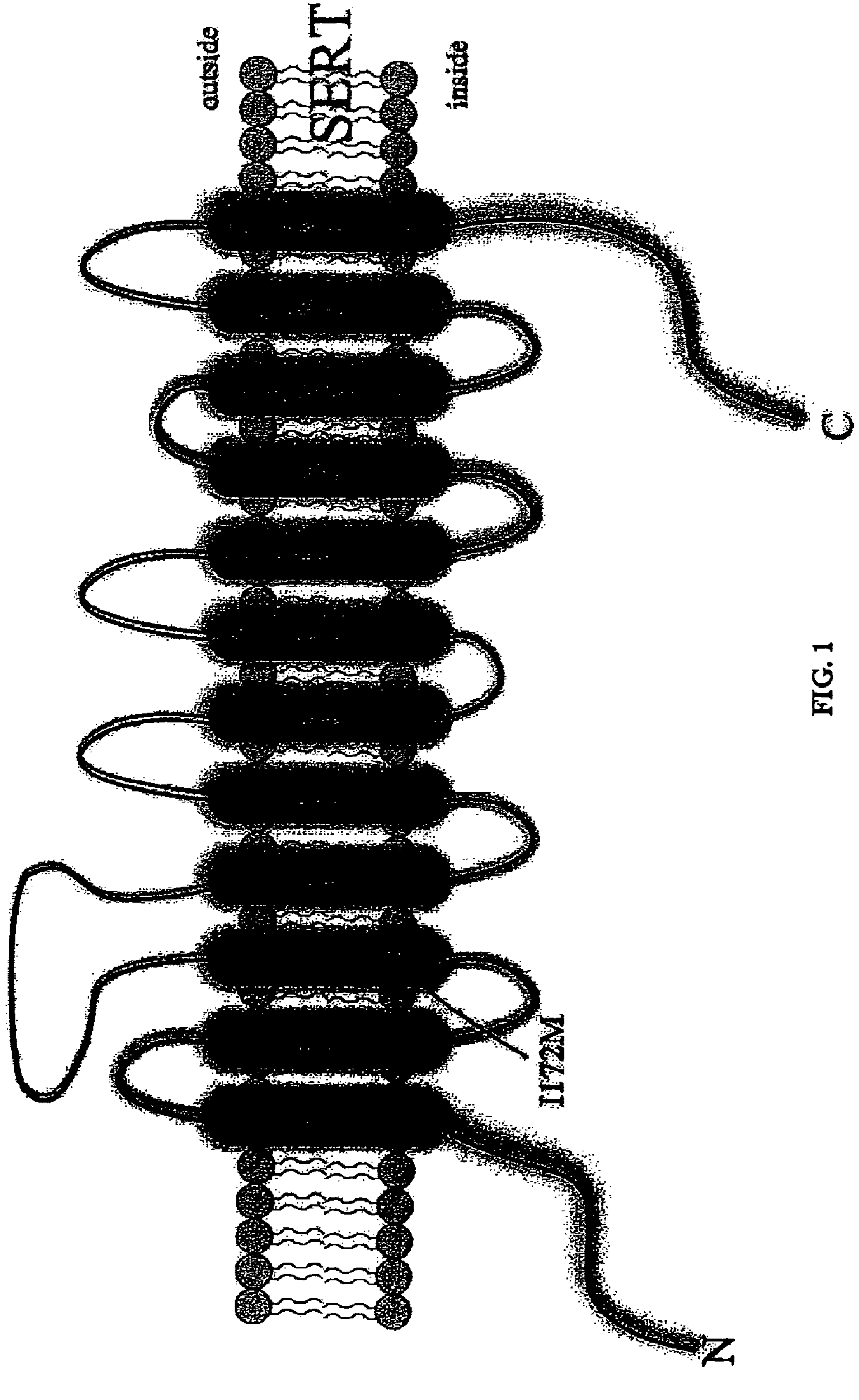
FIG. 1—Model of the serotonin transporter showing the mutation of isoleucine at position 172 to a methionine.

Serotonin and the serotonin transporter mediate diverse aspects of neuronal signaling and are involved in the pathology of a number of nervous system related disorders. The serotonin transporter is a target of various therapeutic agents used in the treatment of neurological and neurodegenerative disorders. Given the diverse uses of the serotonin transporter, identification of novel therapeutic agents is limited by the repeated use of the same protein or DNA as a target. Therefore, there is a need for improved target molecules that permit recognition of novel contact sites of the serotonin transporter, and allow cost effective and rapid screening methods to identify modulators of the serotonin transporter that may be useful as therapeutic agents in the treatment of neurological and neurodegenerative disorders.

Thus, the present invention provides novel serotonin transporters for high throughput screening of therapeutic agents. Screening method provides a mutant serotonin transporter for identifying substances that block or inhibit the serotonin transporter. Provided in the present invention are nucleic acid sequences encoding the amino acid sequences of the human and mouse serotonin transporters (SERT) that controls a significant fraction of antidepressant potency. Antidepressants are known in the art to interact with several targets. Such targets may include, but are not limited to, neurokinins, nicotinic acetylcholine receptors (nAChR) and 5HT2A receptors. Other targets may include serine/threonine kinases such as $Ca^{2+}$/calmodulin-dependent protein kinase II and cyclic AMP-dependent protein kinase, which have been shown to be activated in the brain following antidepressant treatment.

The present invention provides a mutation of isoleucine (I) at position 172 of the serotonin transporter that influences the interactions of antidepressants. The specific I172M mutant contributes to the selectivity for and potency of SERT inhibitors and thus, is beneficial in screening for antidepressants that lack a conventional mode of antagonism. To date, none of the known SERT polymorphisms have been characterized to have altered antidepressant potency. The present invention provides an artifical SERT molecule that has the ability to alter antidepressant potency. This mutation has been demonstrated to render the mouse and human SERT less sensitive to subclasses of antidepressants and also diminishes cocaine potency. Futhermore, a Y95F substitution in transmembrane domain I showed about 4-order magnitude potency shift for the SSRI citalopram whereas serotonin (5HT) recognition appeared normal. An even greater loss of SSRI recognition was observed using the combination of the Y95F/I172M double mutant.

Thus, present invention provides a method of screening for therapeutic agents that block the serotonin transporter by precluding the isolation of agents that depend largely on the isoleucine at position 172 of the serotonin transporter. These mutant SERTs are provided in the present invention as a novel platform for high-throughput screening of SERT blockers or inhibitors that utilize the novel site. The present invention provides for the identification of novel modes of antidepressant recognition and for generating in vivo models (transgenic animals) to test theories of actions of psychostimulant and antidepressants.

II. Serotonin Transporter (SERT)

Selective antagonism of serotonin (5-hydroxytryptamine, 5HT) and noradrenaline (NA) transport by antidepressants is a key element to our current understanding of human behavioral disorders (Ashton, 1987). The serotoninergic system modulates numerous behavioral and physiological functions and has been associated with control of mood, emotion, sleep and appetite. Synaptic serotonin (SE), also called 5-hydroxytryptamine or 5HT, concentration is controlled by the serotonin transporter (SERT) which is involved in reuptake of serotonin into the pre-synaptic terminal. In several studies, 5HT uptake and/or transport sites have been found to be reduced in platelets of patients suffering from depression and reduced in post-mortem brain samples of depressed patients and suicide victims (Meltzer et al., 1981; Suranyi-Cadotte et al., 1985; Briley et al., 1993; Paul et al., 1981; Perry et al., 1983; Stanley et al., 1982). The cloning of the human SERT protein by Ramamoorthy et al. (1993), shows that human SERT is encoded by a single gene that is localized to chromosome 17q11.1-17q12 and encodes for a 630-amino acid protein. The hSERT is a $Na^+$- and $Cl^-$-coupled serotonin transporter and has been found to be expressed on human neuronal, platelet, placental, and pulmonary membranes (Ramamoorthy et al., 1993).

The SERT has been associated with depression and anxiety (Soubrie, 1988; Barnes, 1988); obesity (Blundell, 1986; Silverstone et al., 1986); alcoholism (Gill et al., 1987; Naranjo et al., 1987); postanoxic intention myoclonus (Van Woert et al., 1976); acute and chronic pain (Le Bars, 1988); as well as sleep disorders (Koella, 1988). SERT has also been shown to mediate behavioral and/or toxic effects of cocaine and amphetamines (Ramamoorthy et al., 1993). A variety of specific serotonin reuptake inhibitors (SSRIs) such as fluoxetine and paroxetine have been developed for the treatment of depression (reviewed in Scholss, 1998). However, as Schloss points out, the art lacks a detailed understanding of the mode of action of these antidepressant drugs on their target, the SERT protein. Furthermore, although several drugs that target the SERT have been identified the art still lacks effective drugs for the treatment and alleviation of depression and other neurological disorders. A better understanding of these transporter proteins would provide a better understanding of these behavioral disorders.

Recent research has shown that polymorphisms in the promoters of SERT's are a risk factor for susceptibility to depression (Neumeister et al., 2002). Other studies have also shown the association of variants of SERT's to other disorders. For example, association for allele 12 of the variable number tandem repeat (VNTR) in the second intron of the SERT gene and schizophrenic disorders has been shown (Tsai et al., 2002).

III. Nucleic Acid Molecules

A. Nucleic Acids Encoding Serotonin Transporter

The present invention provides nucleic acids encoding the amino acid sequences of the serotonin transporter. Nucleic acids of the present invention may be derived from genomic DNA, complementary DNA (cDNA). More particularly, the present invention provides synthetic nucleic acid sequences comprising the amino acid sequences of the human and mouse serotonin transporter. Nucleic acids of the present invention also concern isolated DNA segments encoding wild-type, polymorphic or mutant serotonin transporter proteins, polypeptides or peptides, comprising the sequence of SEQ ID NO: 1, SEQ ID NO: 3, SEQ ID NO: 7, SEQ ID NO: 9, SEQ ID NO: 11, SEQ ID NO: 13, SEQ ID NO: 15, or SEQ ID NO: 17 and biologically functional equivalents thereof.

A "nucleic acid" as used herein includes single-stranded and double-stranded molecules, as well as DNA, RNA, chemically modified nucleic acids and nucleic acid analogs. It is contemplated that a nucleic acid within the scope of the present invention may be of about 20, of about 50 to about 90, of about 100 to about 200, of about 210 to about 300, of about 310 to about 350, of about 360, to about 400, of about 410 to about 450, of about 460 to about 500, of about 510 to about 550, of about 560 to about 600, of about 610 to about 650, of about 660 to about 700, of about 710 to about 750, of about 760 to about 800, of about 810 to about 850, of about 860 to about 900, about 1000, about 1100, about 1200, about 1300, about 1400, about 1500, about 1600, about 1700, about 1800, about 1900 or greater nucleotide residues in length. Those of skill will recognize that in cases where the nucleic acid region encodes a serotonin transporter peptide, polypeptide or protein, the nucleic acid region can be quite long, depending upon the number of amino acids in the serotonin transporter molecule.

It is contemplated that the serotonin transporter may be encoded by any nucleic acid sequence that encodes the appropriate amino acid sequence. The design and production of nucleic acids encoding a desired amino acid sequence is well known to those of skill in the art, using standardized codon tables (Table 1). In preferred embodiments, the codons selected for encoding each amino acid may be modified to optimize expression of the nucleic acid in the host cell of interest. The term "functionally equivalent codon" is used herein to refer to codons that encode the same amino acid, such as the six codons for arginine or serine, and also refers to codons that encode biologically equivalent amino acids. Codon preferences for various species of host cell are well known in the art. Codons preferred for use in humans, are well known to those of skill in the art (Wada et al., 1990). Codon preferences for other organisms also are well known to those of skill in the art (Wada et al., 1990, included herein in its entirety by reference) and can be found on the internet at the Codon Usage Database website.

TABLE 1

| Amino Acid | | | Codons |
|---|---|---|---|
| Alanine | Ala | A | GCA GCC GCG GCU |
| Cysteine | Cys | C | UGC UGU |
| Aspartic acid | Asp | D | GAC GAU |
| Glutamic acid | Glu | B | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | AGC AGU UCA UCC UCG UCU |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |

In certain embodiments, the invention concerns isolated DNA segments and recombinant vectors that include within their sequence a contiguous nucleic acid sequence encoding the amino acid sequences shown in SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, or SEQ ID NO: 18. As used herein, the term "DNA segment" refers to a DNA molecule that has been isolated free of total genomic DNA of a particular species. Therefore, a DNA segment encoding serotonin transporter refers to a DNA segment that contains wild-type, polymorphic or mutant serotonin transporter coding sequences yet is isolated away from, or purified free from, total mammalian genomic DNA. Included within the term "DNA segment," are DNA segments and smaller fragments of such segments, and also recombinant vectors, including, for example, plasmids, cosmids, phage, viruses, and the like.

Similarly, a DNA segment comprising an isolated or purified serotonin transporter gene refers to a DNA segment including serotonin transporter protein, polypeptide or peptide coding sequences and, in certain aspects, regulatory sequences, isolated substantially away from other naturally occurring genes or protein encoding sequences. In this respect, the term "gene" is used for simplicity to refer to a functional protein, polypeptide or peptide encoding unit. As will be understood by those in the art, this functional term includes both genomic sequences, cDNA sequences and engineered segments that express, or may be adapted to express, proteins, polypeptides, domains, peptides, fusion proteins and mutants of serotonin transporter encoded sequences. "Isolated substantially away from other coding sequences" means that the gene of interest, in this case the serotonin transporter gene, forms the significant part of the coding region of the DNA segment, and that the DNA segment does not contain large portions of naturally-occurring coding DNA, such as large chromosomal fragments or other functional genes or cDNA coding regions. Of course, this refers to the DNA segment as originally isolated, and does not exclude genes or coding regions later added to the segment by the hand of man.

In particular embodiments, the invention concerns isolated DNA segments that encode a serotonin transporter protein, polypeptide or peptide that includes within its amino acid sequence a contiguous amino acid sequence in accordance with, or essentially as set forth in, SEQ ID NO: 2, SEQ ID NO: 4, SEQ ID NO: 6 or SEQ ID NO: 8.

The term "a sequence essentially as set forth in SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, or SEQ ID NO: 18" means that the sequence substantially corresponds to a portion of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, or SEQ ID NO: 18 and has relatively few amino acids that are not identical to, or a biologically functional equivalent of, the amino acids of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, or SEQ ID NO: 18.

The term "biologically functional equivalent" is well understood in the art and is further defined in detail herein. Accordingly, sequences that have about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99%, and any range derivable therein, such as, for example, about 70% to about 80%, and more preferably about 81% and about 90%; or even more preferably, between about 91% and about 99%; of amino acids that are identical or functionally equivalent to the amino acids of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, or SEQ ID NO: 18 will be sequences that are "essentially as set forth in SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16 or SEQ ID NO: 18", provided the biological activity of the protein is maintained.

In certain other embodiments, the invention concerns isolated DNA segments that include within their sequence a nucleic acid sequence essentially as set forth in SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, or SEQ ID NO: 17. The term "essentially as set forth in SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, or SEQ ID NO: 17" is used in the same sense as described above and means that the nucleic acid sequence substantially corresponds to a portion of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, or SEQ ID NO: 17 and has relatively few codons that are not identical, or functionally equivalent, to the codons of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, or SEQ ID NO: 17. Again, DNA segments that encode proteins, polypeptide or peptides exhibiting serotonin transporter activity will be most preferred.

It will also be understood that amino acid and nucleic acid sequences may include additional residues, such as additional N- or C-terminal amino acids or 5' or 3' sequences, and yet still be essentially as set forth in one of the sequences disclosed herein, so long as the sequence meets the criteria set forth above, including the maintenance of biological protein, polypeptide or peptide activity where an amino acid sequence expression is concerned. The addition of terminal sequences particularly applies to nucleic acid sequences that may, for example, include various non-coding sequences flanking either of the 5' or 3' portions of the coding region or may include various internal sequences, i.e., introns, which are known to occur within genes.

Excepting intronic or flanking regions, and allowing for the degeneracy of the genetic code, sequences that have about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99%, and any range derivable therein, such as, for example, about 70% to about 80%, and more preferably about 81% and about 90%; or even more preferably, between about 91% and about 99%; of nucleotides that are identical to the nucleotides of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, or SEQ ID NO: 17 will be sequences that are "essentially as set forth in SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, or SEQ ID NO: 17".

If desired, one also may prepare fusion proteins and peptides, e.g., where the nucleic acid encoding a serotonin transporter are aligned within the same expression unit with other proteins or peptides having desired functions, such as for purification or immunodetection purposes (e.g., proteins that may be purified by affinity chromatography and enzyme label coding regions, respectively).

In addition to the "standard" DNA and RNA nucleotide bases, modified bases are also contemplated for use in particular applications of the present invention. A table of exemplary, but not limiting, modified bases is provided herein (Table 2).

TABLE 2

Modified and Unusual Amino Acids

| Abbr. | Amino Acid | Abbr. | Amino Acid |
|---|---|---|---|
| Aad | 2-Aminoadipic acid | EtAsn | N-Ethylasparagine |
| Baad | 3-Aminoadipic acid | Hyl | Hydroxylysine |
| Bala | -alanine, -Amino-propionic acid | AHyl | allo-Hydroxylysine |
| Abu | 2-Aminobutyric acid | 3Hyp | 3-Hydroxyproline |
| 4Abu | 4-Aminobutyric acid, piperidinic acid | 4Hyp | 4-Hydroxyproline |
| Acp | 6-Aminocaproic acid | Ide | Isodesmosine |
| Ahe | 2-Aminoheptanoic acid | AIle | allo-Isoleucine |
| Aib | 2-Aminoisobutyric acid | MeGly | N-Methylglycine, sarcosine |
| Baib | 3-Aminoisobutyric acid | MeIle | N-Methylisoleucine |
| Apm | 2-Aminopimelic acid | MeLys | 6-N-Methyllysine |
| Dbu | 2,4-Diaminobutyric acid | MeVal | N-Methylvaline |
| Des | Desmosine | Nva | Norvaline |
| Dpm | 2,2'-Diaminopimelic acid | Nle | Norleucine |
| Dpr | 2,3-Diaminopropionic acid | Orn | Ornithine |
| EtGly | N-Ethylglycine | | |

In addition to nucleic acids encoding the serotonin transporter the present invention encompasses complementary nucleic acids that hybridize under high stringency conditions with such coding nucleic acid sequences. High stringency conditions for nucleic acid hybridization are well known in the art. For example, conditions may comprise low salt and/or high temperature conditions, such as provided by about 0.02 M to about 0.15 M NaCl at temperatures of about 50° C. to about 70° C. It is understood that the temperature and ionic strength of a desired stringency are determined in part by the length of the particular nucleic acid(s), the length and nucleotide content of the target sequence(s), the charge composition of the nucleic acid(s), and to the presence or concentration of formamide, tetramethylammonium chloride or other solvent(s) in a hybridization mixture.

B. Site-Specific Mutagenesis

It is further contemplated by the present invention, that nucleic acids encoding a serotonin transporter may encompass biologically functional equivalent modified polypeptides and peptides through site-directed or site-specific mutagenesis of the underlying DNA. Techniques for site-directed mutagenesis are known to those of ordinary skill in the art, and can be practiced without undue experimentation in the context of the present invention.

The technique provides a ready ability to prepare and test sequence variants, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

The technique typically employs a bacteriophage vector that exists in both a single-stranded and double-stranded form. Typical vectors useful in site-directed mutagenesis include vectors such as the M13 phage. These phage vectors are commercially available and their use is generally well known to those skilled in the art. Double stranded plasmids are also routinely employed in site directed mutagenesis, which eliminates the step of transferring the gene of interest from a phage to a plasmid.

In general, site-directed mutagenesis is performed by first obtaining a single-stranded vector, or melting of two strands of a double-stranded vector which includes within its sequence a DNA sequence encoding the desired protein. An oligonucleotide primer bearing the desired mutated sequence is synthetically prepared. This primer is then annealed with the single-stranded DNA preparation, and subjected to DNA polymerizing enzymes such as *E. coli* polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as *E. coli* cells, and clones are selected that include recombinant vectors bearing the mutated sequence arrangement.

The preparation of sequence variants of the selected gene using site-directed mutagenesis is provided as a means of producing potentially useful species and is not meant to be limiting, as there are other ways in which sequence variants of genes may be obtained. For example, recombinant vectors encoding the desired gene may be treated with mutagenic agents, such as hydroxylamine, to obtain sequence variants.

IV. Proteins, Polypeptides, and Peptides Encoding a Serotonin Transporter

The present invention provides amino acid sequences of the serotonin transporter. More particularly, the present invention provides synthetic amino acid sequences of the human and mouse serotonin transporter as in SEQ ID NO: 4, SEQ ID NO: 8, SEQ ID NO: 10, SEQ ID NO: 12, SEQ ID NO: 14, SEQ ID NO: 16, or SEQ ID NO: 18. As used herein, an "amino molecule" refers to any amino acid, amino acid derivative or amino acid mimic as would be known to one of ordinary skill in the art. In certain embodiments, the residues of the protein, polypeptide or peptide molecule are sequential, without any non-amino molecule interrupting the sequence of amino molecule residues. In other embodiments, the sequence may comprise one or more non-amino molecule moieties. In particular embodiments, the sequence of residues of the protein, polypeptide, or peptide molecule may be interrupted by one or more non-amino molecule moieties.

Accordingly, the term "amino acid composition" encompasses amino molecule sequences comprising at least one of the 20 common amino acids in naturally synthesized proteins, or at least one modified or unusual amino acid, including but not limited to those shown on Table 2. It is also well understood that where certain residues are shown to be particularly important to the biological or structural properties of a protein, polypeptide or peptide, e.g., residues in binding regions or active sites, such residues may not generally be exchanged. In this manner, functional equivalents are defined herein as those peptides which maintain a substantial amount of their native biological activity.

In certain embodiments the amino acid composition of the present invention comprises at least one protein, polypeptide or peptide. In further embodiments the amino acid composition comprises a biocompatible protein, polypeptide or peptide. As used herein, the term "biocompatible" refers to a substance which produces no significant untoward effects when applied to, or administered to, a given organism according to the methods and amounts described herein. Such untoward or undesirable effects are those such as significant toxicity or adverse immunological reactions. In preferred embodiments, biocompatible protein, polypeptide or peptide containing compositions will generally be mammalian proteins or peptides or synthetic proteins or peptides each essentially free from toxins, pathogens and harmful immunogens.

In certain embodiments, amino acid sequence variants of the protein, polypeptide, or peptide may be prepared. Such variants may can be substitutional, insertional or deletion variants are methods of preparing these variants are well known in the art. These variants include polymorphisms and mutants that affect the function and activity of the serotonin transporter. Deletion variants lack one or more residues of the native protein which are not essential for function or immuogenic activity. Insertional variants typically involve the addition of material at a non-terminal point in the polypeptide. Insertional variants include fusion proteins, or hybrid proteins containing sequences from other proteins and polypeptides which are homologues of the polypeptide.

Substitutional variants typically contain the exchange of one amino acid for another at one or more sites within the protein, and may be designed to modulate one or more properties of the polypeptide such as stability against proteolytic cleavage. Substitutions preferably are conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine.

Amino acid substitutions are generally based on the relative similarity of the amino acid side-chain substituents, for example, their hydrophobicity, hydrophilicity, charge, size, and the like. An analysis of the size, shape and type of the amino acid side-chain substituents reveals that arginine, lysine and histidine are all positively charged residues; that alanine, glycine and serine are all a similar size; and that phenylalanine, tryptophan and tyrosine all have a generally similar shape. Therefore, based upon these considerations, arginine, lysine and histidine; alanine, glycine and serine; and phenylalanine, tryptophan and tyrosine; are defined herein as biologically functional equivalents.

To effect more quantitative changes, the hydropathic index of amino acids may be considered. Each amino acid has been assigned a hydropathic index on the basis of their hydrophobicity and charge characteristics, these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a proteinaceous molecule is generally understood in the art (Kyte and Doolittle, 1982). It is known that certain amino acids may be substituted for other amino acids having a similar hydropathic index or score and still retain a similar biological activity. In making changes based upon the hydropathic index, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity, particularly where the biological functional equivalent protein, polypeptide or peptide thereby created is intended for use in immunological embodiments, as in certain embodiments of the present invention. U.S. Pat. No. 4,554,101, states that the greatest local average hydrophilicity of a proteinaceous molecule, as governed by the hydrophilicity of its adjacent amino acids, correlates with its immunogenicity and antigenicity, i.e., with a biological property of the proteinaceous molecule.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

In making changes based upon similar hydrophilicity values, the substitution of amino acids whose hydrophilicity values are within ±2 is preferred, those which are within ±1 are particularly preferred, and those within ±0.5 are even more particularly preferred.

V. Screening For Serotonin Transporter Blockers/Inhibitors

Defects in serotonin transporter are associated with various nervous system disorders including depression, stress disorders, attention deficit disorder, anxiety, obesity, several sleep related disorders and certain neurodegenerative diseases (Edwards, 1993). For example, the biogenic amine transporter which is responsible for inactivation of serotonin is a major target for multiple psychoactive substances including cocaine, amphetamines, methylphenidate (Ritalin™), tricyclic antidepressants and the SSRIs such as fluoxetine (Prozac™). However, there is still a need in the art to identify other modulators of the serotonin transporter given the large number of neurological and psychiatric diseases that are associated with transporter defects. The available SSRIs are known to have side-effects such as, but not limited to, anxiety, impotency, sleep disorders. New therapeutic agents are needed that are safer and more effective since SSRIs take about 6-8 weeks for the effects to develop. Thus, additional classes of drugs that act on the same target but in a different manner would generate better, more beneficial drugs.

The present invention therefore provides methods for identifying blockers or inhibitors of the function or activity of serotonin transporter. These methods may comprise random screening of large libraries of candidate substances. Alternatively, the methods may be used to focus on particular classes of compounds selected with an eye towards structural attributes that are believed to make them more likely to modulate the function or activity of the serotonin transporter.

By function or activity, it is meant that one may assay for uptake, accumulation, or clearance of the neurotransmitter, its analog or derivative or for some biological aspect of neurotransmitter release, uptake or clearance. Micro-dialysis and amperometry may be used to assay transporter function in vivo (Giros et al., 1996; Galli et al., 1998).

The present invention therefore provides a method of screening for candidate substances that block serotonin transporter activity comprising:

a) providing a cell or cell extract expressing a serotonin transporter protein having an amino acid sequence of SEQ ID NO: 4, SEQ ID NO: 8, SEQ ID NO: 10, SEQ ID NO: 12, SEQ ID NO: 14, SEQ ID NO: 16, or SEQ ID NO: 18;
b) exposing the cell or cell extract to a candidate substance;
c) measuring binding of the candidate substance to the serotonin transporter in step (a); and
d) comparing binding of the candidate substance by the serotonin transporter of step (a) to binding of the candidate substance by a serotonin transporter having an amino acid sequence of SEQ ID NO: 2 or SEQ ID NO: 6, wherein the ability of the candidate substance to bind to the serotonin transporter having the amino acid sequence of SEQ ID NO: 4, SEQ ID NO: 8, SEQ ID NO: 10, SEQ ID NO: 12, SEQ ID NO: 14, SEQ ID NO: 16, or SEQ ID NO: 18 but not the serotonin transporter having an amino acid sequence of SEQ ID NO: 2 or SEQ ID NO: 6 indicates that the candidate substance blocks serotonin transporter activity. Such screening method may further comprise measuring transport of the candidate substance by the serotonin transporter as in step (a); and a comparing step as in (d) above to further identify a candidate substance.

Assays may be conducted in cell free systems such as cellular extracts, cell membrane preparations which may be prepared by lysing cells, in isolated cells, in cells that express endogenous serotonin transporter, in cells that are genetically engineered to express the serotonin transporter, in cells that exogenously or endogenously express mutant or functionally deficient transporters, or in organisms including transgenic animals or animal models of diseases wherein the disease is associated with neurotransmitter transporters.

It will, of course, be understood that all the screening methods of the present invention are useful in themselves notwithstanding the fact that effective candidates may not be found. The invention provides methods for screening for such candidates, not solely methods of finding them.

A. Inhibitors/Blockers

As used herein the term "candidate substance" refers to any molecule that may potentially inhibit or block the serotonin transporter function or activity. The candidate substance may be a protein or fragment thereof, a small molecule, or even a nucleic acid molecule. It may prove to be the case that the most useful pharmacological compounds will be compounds that are structurally related to known neurotransmitter transporter modulators, agonists and antagonists such as cocaine, amphetamines, monoamine oxidase inhibitors, imipramine and the like. Using lead compounds to help develop improved compounds is know as "rational drug design" and includes not only comparisons with know inhibitors and activators, but predictions relating to the structure of target molecules.

The goal of rational drug design is to produce structural analogs of biologically active polypeptides or target compounds. By creating such analogs, it is possible to fashion drugs, which are more active or stable than the natural molecules, which have different susceptibility to alteration or which may affect the function of various other molecules. In one approach, one would generate a three-dimensional structure for a target molecule, or a fragment thereof. This could be accomplished by x-ray crystallography, computer modeling or by a combination of both approaches.

It also is possible to use antibodies to ascertain the structure of a target compound activator or inhibitor. In principle, this approach yields a pharmacore upon which subsequent drug design can be based. It is possible to bypass protein crystallography altogether by generating anti-idiotypic antibodies to a functional, pharmacologically active antibody. As a mirror image of a mirror image, the binding site of anti-idiotype would be expected to be an analog of the original antigen. The anti-idiotype could then be used to identify and isolate peptides from banks of chemically- or biologically-produced peptides. Selected peptides would then serve as the pharmacore.

On the other hand, one may simply acquire, from various commercial sources, small molecule libraries that are believed to meet the basic criteria for useful drugs in an effort to "brute force" the identification of useful compounds. Screening of such libraries, including combinatorially generated libraries (e.g., peptide libraries), is a rapid and efficient way to screen large number of related (and unrelated) compounds for activity. Combinatorial approaches also lend themselves to rapid evolution of potential drugs by the creation of second, third and fourth generation compounds modeled of active, but otherwise undesirable compounds.

Candidate substances may include fragments or parts of naturally-occurring compounds, or may be found as active combinations of known compounds, which are otherwise inactive. It is proposed that compounds isolated from natural sources, such as animals, bacteria, fungi, plant sources, including leaves and bark, and marine samples may be assayed as candidates for the presence of potentially useful pharmaceutical agents. It will be understood that the pharmaceutical agents to be screened could also be derived or synthesized from chemical compositions or man-made compounds. Thus, it is understood that the candidate substance identified by the present invention may be peptide, polypeptide, polynucleotide, small molecule inhibitors or any other compounds that may be designed through rational drug design starting from known inhibitors or stimulators.

In addition to the modulating compounds initially identified, the inventors also contemplate that other sterically similar compounds may be formulated to mimic the key portions of the structure of the modulators. Such compounds, which may include peptidomimetics of peptide modulators, may be used in the same manner as the initial modulators.

An inhibitor or blocker according to the present invention may be one which exerts its inhibitory or blocking effect upstream, downstream or directly on the serotonin transporter. Regardless of the type of inhibitor or blocker identified by the present screening methods, the effect of the inhibition or blocker by such a compound results in a difference as compared to that observed in the absence of the added candidate substance.

B. In vitro Assays

In particular embodiments, the present invention provides a method for high throughput screening for blockers or inhibitors of the serotonin transporter. To accomplish this, a quick, inexpensive and easy assay to run is an in vitro assay. Such assays generally use isolated molecules, can be run quickly and in large numbers, thereby increasing the amount of information obtainable in a short period of time. A variety of vessels may be used to run the assays, including test tubes, plates, dishes and other surfaces such as dipsticks or beads.

One example of a cell free assay in this invention is the use of cellular extracts that comprise a neurotransmitter. These may be cell membrane preparations that comprise a neurotransmitter transporter, particularly a serotonin transporter.

Another example is a cell-binding assay. While not directly addressing function, the ability of an inhibitor or blocker to bind to a target molecule (in this case the serotonin transporter) in a specific fashion is strong evidence of a related biological effect. For example, binding of a molecule to a serotonin transporter may, in and of itself, be inhibitory, due to steric, allosteric or charge-charge interactions. The serotonin transporter protein may be either free in solution, fixed to a support, expressed in or on the surface of a cell. Either the serotonin transporter or the compound may be labeled, thereby permitting determining of binding. Usually, the target will be the labeled species, decreasing the chance that the labeling will interfere with or enhance binding. Competitive binding formats can be performed in which one of the agents is labeled, and one may measure the amount of free label versus bound label to determine the effect on binding.

A technique for high throughput screening of compounds is described in WO 84/03564. Large numbers of small peptide test compounds are synthesized on a solid substrate, such as plastic pins or some other surface. Bound polypeptide is detected by various methods.

1. Measurement of Transport

In some embodiments, the present invention provides a novel and rapid method for analysis of transport by a serotonin transporter that comprises the measurement of uptake and/or accumulation of serotonin and analogues thereof that are specifically taken up by the transporter. Typically, this is accomplished by measuring the uptake or binding of radiolabeled serotonin (e.g. [$^3$H]serotonin) or a radiolabeled antagonist such as [$^3$H]citalopram, [$^3$H]paroxetine, or [$^{125}$I] RTI-55. Conventional assays involves the uptake of radiolabeled 5HT where antagonist sensitivity is measured for inhibition of serotonin accumulation or the inhibition of labeled antagonist binding to intact cells expressing SERT or to membranes from intact cells expressing SERT. Basically, cells transfected with a SERT construct are washed in assay buffer followed by a preincubation in 37° C. assay buffer containing 1.8 g/L glucose. This is followed by an incubation period, about 10 minutes, at 37° C. in the presence of [$^3$H]-5-HT, or a radiolabeled antagonist such as [$^3$H]citalopram, [$^3$H]paroxetine, or [$^{125}I$]RTI-55. Details of this assay are provided in the Examples.

a. Scintillation Proximity Assays

Measurement of transport may also be involve scintillation proximity assays, which is used to count the accumulated radiolabel on plates having scintillant embedded in them. Basically, cells are plated at 50% confluence on 0.4-μm pore size 6.5-mm Transwell cell culture filter inserts and grown for 7 days. A cell monolayer growing on the porous membrane of the cell culture filter insert effectively separates each well in the cell culture plate into two chambers. The apical membranes of epithelial cells plated on these filters faces the chamber above the cells and the basolateral membranes face the lower chamber through the filter. After one wash each of the apical (upper chamber) and basolateral (lower chamber) sides of the monolayer with PBS/Ca/Mg, the cells are incubated in PBS/Ca/Mg containing $^3$H-labeled substrate either in the upper or the lower chamber at 22° C. At the end of the incubation cells are washed either three times from the apical side and once from the basolateral side (when $^3$H-labeled substrate was present in the upper chamber) or once from the apical side and three times from the basolateral side (when substrate was present in the lower chamber). The apical side of the cells are washed by adding 0.2 ml of ice-cold PBS to the upper chamber and aspirating. The basolateral side of the cells are washed by pipetting ice-cold PBS over the bottoms of the filter inserts. After the washes, the filters with cells attached are excised from the insert cups, submerged in 3 ml of Optifluor scintillation fluid (Packard Instrument Co., Downers Grove, Ill.), and counted in a Beckman LS-3801 liquid scintillation counter. Transport assays on 48-well plates were described previously (Gu et al., 1994).

b. Voltage and Patch Clamp

The present invention also employs a means of determining the serotonin transporter activity or function by measuring the change in movement across a membrane, when the transporter is active. This may be accomplished using the voltage clamp technique, as is well known in the art, this allows the gating properties of the voltage-gated channels to be analyzed.

In short, the voltage clamp technique is a procedure whereby the transmembrane voltage of a membrane segment is rapidly set and maintained at a desired level. Once the membrane potential is controlled, the current flowing through the channels in that segment can be measured.

The patch clamp technique allows the voltage clamp technique to be applied to a small patch of membrane containing a single voltage-sensitive channel. The basic idea behind a patch clamp experiment is to isolate a patch of membrane so small that it contains a single voltage-gated channel. Once this patch of membrane is isolated, the single channel can be voltage clamped. Using this technique, the gating properties of the serotonin transporter can be characterized.

2. Other Methods of Measurement of Transport

Other methods of measurement contemplated in the present invention may involve fluorescence microscopy. This may involve the use of fluorescent substrates, some of which are contemplated to be analogs of other native neurotransmitters.

a. Microscopy

Fluorescent microscopy is used to measure transport using serotonin or analogues thereof which are fluorescent substrates for the serotonin transporter. Cells that either endogenously or exogenously express a serotonin transporter are isolated and plated on glass bottom Petri-dishes or multi-well plates that may typically be coated with poly-L-lysine or any other cell adhesive agent. Cells are typically cultured for three or more days. The culture medium is then aspirated and the cells are mounted on a Zeiss 410 confocal microscope. During the confocal measurement cells remain without buffer for approximately thirty seconds. Background autofluorescence is established by collecting images for ten seconds prior to the addition of the buffer and serotonin or analogues thereof. As serotonin or an analogue thereof has a large Stoke shift between excitation ($l_{max}$=488 nm) and emission maxima ($l_{max}$=610 mn), the argon laser is tuned to 488 mn and the emitted light filtered with a 580-630 nm band pass filter (Imax =610nm). The substantial red shift can be exploited to reduce background auto-fluorescence produced in the absence of substrate. The gain (contrast) and offset (brightness) for the photomultiplier tube (PMT) may be set to avoid detector saturation at the higher serotonin concentrations that may be used in certain experiments. The effects of photobleaching on serotonin accumulation may also be determined by examining the rate of serotonin accumulation and decay at various acquisition rates. In a constant pool of serotonin, rates as high as 20 Hz (50 msec/image) can be set.

b. Fluorescence Anisotropy Measurements

To evaluate serotonin or analogues thereof binding to the surface membranes, cells expressing a serotonin transporter may be exposed to serotonin or analogues thereof with horizontal polarizer, with the polarizer rapidly switching to the vertical position. Cells may be imaged with alternating polarizations for 3 minutes to measure light intensity in the horizontal ($I_h$) and vertical ($I_v$) positions in order to calculate the anisotropy ratio, $r=(I_v-gI_h)/(I_v+2\ g\ I_h)$. The factor g may be determined by using a half wave plate as described by Blackman et al. (1996). In this formulation, r=0.4 implies an immobile light source. Surface anisotropy can be measured at the cell circumference over 1 pixel width (0.625 mm). Cytosolic anisotropy can be measured near the center of the cell, approximately 5 pixel widths from the membrane.

c. Image Analysis

The fluorescent images may be processed using suitable software. For example, fluorescent images may be processed using MetaMorph imaging software (Universal Imaging Corporation, Downington Pa.). Fluorescent accumulation may be established by measuring the average pixel intensity of time resolved fluorescent images within a specified region identified by the DIC image. Average pixel intensity is used to normalize among cells.

d. Single Cell Fluorescence Microscopy

In some embodiments, the invention provides measurement of transporter characteristics at the single-cell level. Single-cell fluorescence microscopy provides a powerful assay to study rapid serotonin uptake kinetics from single cells.

e. Automation

The inventors further contemplate that all these methods are adaptable to high-throughput formats using robotic fluid dispensers, multi-well formats and fluorescent plate readers for the identification of serotonin transport modulators.

3. Behavioral Testing

Several tests (behavioral test) may be conducted to assess the efficacy of an antidepressant of the present invention. Such test may include but are not limited to elevated plus-maze test, chronic mild stress test, forced swimming test, social defeat stress-induced anxiety test, or the light/dark test.

a. Elevated Plus-Maze Test in Mice

The apparatus may be based on that described by Pellow et al. (1985). In this procedure, the apparatus is elevated and contains two open and two enclosed arms, arranged so that the arms of the same type are opposite to each other. The apparatus is equipped with infrared beams and sensors capable of measuring arm activity for a given period of time. In addition, mice may be observed via video link by an observer located in an adjacent room. This arrangement allowed the recording of attempts at entry into open arms followed by avoidance responses, including stretched attend posture (the mouse stretches forward and retracts to original position). Tests may be performed 60 min after p.o. administration of the drugs.

b. Light/Dark Test in Mice

For this test, the apparatus may be based on that described by Misslin et al. (1989). For example, the apparatus may consist of two poly(vinyl chloride) boxes (20×20×14 cm), one of which is darkened. A desk lamp may be placed 20 cm above the lit box provided the room illumination. An opaque plastic tunnel (5×7×10 cm) may be used to separated the dark box from the illuminated one. The apparatus may be equipped with infrared beams capable of recording during a specific time period: (i) time spent by mice in the lit box, and (ii) number of tunnel crossings. Tests may be performed 30 min after i.p. administration of the drugs.

c. Forced Swimming Test in Mice

The forced swim test (FST) is widely used in the art for screening substances with a potential antidepressant effect. This procedure was originally described by Porsolt et al. (1977) however, modification may be made. Basically, the duration of immobility of the mice is measured for a given time period. The immobility observed by the FST is interpreted as 'behavioral despair'.

C. In cyto Assays

The present invention also contemplates the screening of candidate substances for their ability to inhibit or block the serotonin transporter in cells. Various cells and cell lines can be utilized for such screening assays as long as the cell expresses a serotonin transporter. This includes cells specifically engineered to expresses a neurotransmitter transporter. Such cells and nucleic acid vectors are described in several sections infra as well as U.S. Pat. Nos. 5,312,734, 5,418,162, and 5,424,185, the contents of which are all incorporated herein by reference. Cells contemplated in the present invention include, but are not limited to, neuronal cells. Depending on the assay, culture may be required. The cell is examined using any of a number of different physiologic assays. Alternatively, molecular analysis may be performed, for example, looking at protein expression, mRNA expression (including differential display of whole cell or polyA RNA) and others.

D. In vivo Assays

In vivo assays are also contemplated in the present invention for screening for candidate substances that block or inhibit the serotonin transporter. Such assays involve the use of various animal models, including transgenic animals that have been engineered to have specific defects, or carry markers that can be used to measure the ability of a candidate substance to reach and effect expression of a serotonin transporter in different cells within the organism. Due to their size, ease of handling, and information on their physiology and genetic make-up, mice are a preferred embodiment, especially for transgenics. However, other animals are suitable as well, including rats, rabbits, hamsters, guinea pigs, gerbils, woodchucks, cats, dogs, sheep, goats, pigs, cows, horses and monkeys (including chimps, gibbons and baboons). Assays for inhibitors or blockers of the serotonin transporter may be conducted using an animal model derived from any of these species.

In such assays, one or more candidate substance is administered to an animal, and the ability of the candidate substance(s) to alter one or more characteristics that are a result of serotonin function or activity, as compared to a similar animal not treated with the candidate substance(s), identifies an inhibitor or blocker. The characteristics may be any of those discussed above with regard to the function or activity of the serotonin neurotransmitter such as change in neurotransmission, change in the activity of some other downstream protein due to a change in neurotransmission, or instead a broader indication such as behavior of an animal, etc.

The present invention provides methods of screening for candidate substance that block or inhibit the serotonin transporter function or activity. In these embodiments, the present invention is directed to a method for determining the ability of a candidate substance to inhibit or block the serotonin transporter function, generally including the steps of: administering a candidate substance to the animal; and determining the ability of the candidate substance to change one or more characteristics of the serotonin transporter.

Treatment of these animals with candidate substance(s) will involve the administration of the substance, in an appropriate form, to the animal. Administration will be by any route that could be utilized for clinical or non-clinical purposes, including but not limited to oral, nasal, buccal, or even topical. Alternatively, administration may be by parenteral methods such as intratracheal instillation, bronchial instillation, intradermal, subcutaneous, intramuscular, intraperitoneal or intravenous injection. Specifically contemplated routes are systemic intravenous injection, regional administration via blood or lymph supply, or directly to an affected site.

Determining the effectiveness of a compound in vivo may involve a variety of different criteria. Also, measuring toxicity and dose response can be performed in animals in a more meaningful fashion than in in vitro or in cyto assays.

1. In vivo Microdialysis

Microdialysis may be used in the present invention to monitor interstitial fluid in various body organs with respect to local metabolic changes. This technique may also be experimentally applied in humans for measurements in adipose tissue. In the present invention, the release of serotonin in the mouse brain, in response to stimuli may be analyzed using this technique.

Microdialysis procedure involves the insertion through the guide cannula of a thin, needle-like perfusable probe (CMA/12.3 mm×0.5 mm) to a depth of 3 mm in striatum beyond the end of the guide. The probe is connected beforehand with tubing to a microinjection pump (CMA-/100). The probe may be perfused at 2 μl/min with Ringer's buffer (NaCl 147 mM; KCl 3.0 mM; $CaCl_2$ 1.2 mM; $MgCl_2$ 1.0 mM) containing 5.5 mM glucose, 0.2 mM L-ascorbate, and 1 μM neostigmine bromide at pH 7.4). To achieve stable baseline readings, microdialysis may be allowed to proceed for 90 minutes prior to the collection of fractions. Fractions (20 μl) may be obtained at 10 minute intervals over a 3 hour period using a refrigerated collector (CMA170 or 200). Baseline fractions may be collected, following the drug or combination of drugs to be tested, been administered to the animal. Upon completion of the collection, each mouse may be autopsied to determine accuracy of probe placement.

2. Transgenic Animals

A transgenic animal of the present invention may involve an animal in which a serotonin transporter molecule such as a mutant serotonin transporter is expressed temporally or spatially in a manner different than a non-transgenic animal. It is contemplated that the transgene, such as a gene encoding a serotonin transporter, may be expressed in a different tissue type or in a different amount or at a different time than the endogenously expressed version of the transgene.

In a general aspect, a transgenic animal is produced by the integration of a given transgene into the genome in a manner that permits the expression of the transgene, or by disrupting the wild-type gene, leading to a knockout of the wild-type gene. Methods for producing transgenic animals are generally described by Wagner and Hoppe (U.S. Pat. No. 4,873,191; which is incorporated herein by reference; Brinster et al.

1985; which is incorporated herein by reference in its entirety; and in Hogan, 1994; which is incorporated herein by reference in its entirety).

U.S. Pat. No. 5,639,457 is also incorporated herein by reference to supplement the present teaching regarding transgenic pig and rabbit production. U.S. Pat. Nos. 5,175,384; 5,175,385; 5,530,179, 5,625,125, 5,612,486 and 5,565,186 are also each incorporated herein by reference to similarly supplement the present teaching regarding transgenic mouse and rat production. Transgenic animals may be crossed with other transgenic animals or knockout animals to evaluate phenotype based on compound alterations in the genome.

As used herein, the term "transgene" means an exogenous gene introduced into a mouse through human intervention, e.g., by microinjection into a fertilized egg or by other methods known to those of average skill in the art. The term includes copies of the exogenous gene present in descendants of the mouse into which the exogenous gene was originally introduced. Likewise, the term "transgenic mouse" includes the original mouse into which the exogenous gene was introduced, as well as descendants of the original mouse so long as such descendants carry the transgene.

The transgenic animal of the invention may be produced by introducing transgenes into the germline of the animal. Embryonal target cells at various developmental stages can be used to introduce transgenes. Different methods are used depending on the stage of development of the embryonal target cell. The specific line(s) of any animal used to practice this invention are selected for general good health, good embryo yields, good pronuclear visibility in the embryo, and good reproductive fitness. In addition, the haplotype is a significant factor.

Introduction of the transgene into the embryo can be accomplished by any means known in the art such as, for example, microinjection, electroporation, or lipofection. For example, the serotonin transporter transgene can be introduced into a mammal by microinjection of the construct into the pronuclei of the fertilized mammalian egg(s) to cause one or more copies of the construct to be retained in the cells of the developing mammal(s). Following introduction of the transgene construct into the fertilized egg, the egg may be incubated in vitro for varying amounts of time, or reimplanted into the surrogate host, or both. In vitro incubation to maturity is within the scope of this invention. One common method is to incubate the embryos in vitro for about 1-7 days, depending on the species, and then reimplant them into the surrogate host.

Retroviral infection can also be used to introduce transgene into a non-human animal. The developing non-human embryo can be cultured in vitro to the blastocyst stage. During this time, the blastomeres can be targets for retroviral infection (Jaenich, 1976). Efficient infection of the blastomeres is obtained by enzymatic treatment to remove the zona pellucida (Manipulating the Mouse Embryo, Hogan eds. (Cold Spring Harbor Laboratory Press, Cold Spring Harbor, 1986). The viral vector system used to introduce the transgene is typically a replication-defective retrovirus carrying the transgene (Jahner et al., 1985; Van der Putten et al., 1985). Transfection is easily and efficiently obtained by culturing the blastomeres on a monolayer of virus-producing cells (Van der Putten, et al., 1985; Stewart et al., 1987). Alternatively, infection can be performed at a later stage. Virus or virus-producing cells can be injected into the blastocoele (Jahner et al., 1982). Most of the founders will be mosaic for the transgene since incorporation occurs only in a subset of the cells which formed the transgenic non-human animal. Further, the founder may contain various retroviral insertions of the transgene at different positions in the genome which generally will segregate in the offspring. In addition, it is also possible to introduce transgenes into the germ line by intrauterine retroviral infection of the midgestation embryo (Jahner et al., 1982).

Embryonal stem cells (ES) may also be used for introducing transgenes. ES cells are obtained from pre-implantation embryos cultured in vitro and fused with embryos (Evans et al., 1981; Bradley et al., 1984; Gossler et al., 1986; and Robertson et al., 1986). Transgenes can be efficiently introduced into the ES cells by DNA transfection or by retrovirus-mediated transduction. Such transformed ES cells can thereafter be combined with blastocysts from a animal. The ES cells thereafter colonize the embryo and contribute to the germ line of the resulting chimeric animal (Jaenisch, 1988).

The number of copies of the transgene constructs which are added to the zygote is dependent upon the total amount of exogenous genetic material added and will be the amount which enables the genetic transformation to occur. Theoretically only one copy is required; however, generally, numerous copies are utilized, for example, 1,000-20,000 copies of the transgene construct, in order to insure that one copy is functional. There is often an advantage to having more than one functioning copy of each of the inserted exogenous DNA sequences to enhance the phenotypic expression of the exogenous DNA sequences. For the purposes of this invention a zygote is essentially the formation of a diploid cell which is capable of developing into a complete organism. Generally, the zygote will be comprised of an egg containing a nucleus formed, either naturally or artificially, by the fusion of two haploid nuclei from a gamete or gametes. Thus, the gamete nuclei must be ones which are naturally compatible, i.e., ones which result in a viable zygote capable of undergoing differentiation and developing into a functioning organism. Generally, a euploid zygote is preferred. If an aneuploid zygote is obtained, then the number of chromosomes should not vary by more than one with respect to the euploid number of the organism from which either gamete originated.

In addition to similar biological considerations, physical ones also govern the amount (e.g., volume) of exogenous genetic material which can be added to the nucleus of the zygote or to the genetic material which forms a part of the zygote nucleus. If no genetic material is removed, then the amount of exogenous genetic material which can be added is limited by the amount which will be absorbed without being physically disruptive. Generally, the volume of exogenous genetic material inserted will not exceed about 10 picoliters. The physical effects of addition must not be so great as to physically destroy the viability of the zygote. The biological limit of the number and variety of DNA sequences will vary depending upon the particular zygote and functions of the exogenous genetic material and will be readily apparent to one skilled in the art, because the genetic material, including the exogenous genetic material, of the resulting zygote must be biologically capable of initiating and maintaining the differentiation and development of the zygote into a functional organism.

Transgenic offspring of the surrogate host may be screened for the presence and/or expression of the transgene by any suitable method. Screening is often accomplished by Southern blot or Northern blot analysis, using a probe that is complementary to at least a portion of the transgene. Western blot analysis using an antibody against the protein encoded by the transgene may be employed as an alternative or additional method for screening for the presence of the transgene product. Typically, DNA is prepared from tail tissue and analyzed by Southern analysis or PCR for the transgene. Alternatively, the tissues or cells believed to express the transgene at the highest levels are tested for the presence and expression of the transgene using Southern analysis or PCR, although any tissues or cell types may be used for this analysis.

Alternative or additional methods for evaluating the presence of the transgene include, without limitation, suitable biochemical assays such as enzyme and/or immunological assays, histological stains for particular marker or enzyme activities, flow cytometric analysis, and the like. Analysis of the blood may also be useful to detect the presence of the transgene product in the blood, as well as to evaluate the effect of the transgene on the levels of various types of blood cells and other blood constituents.

Progeny of the transgenic animals may be obtained by mating the transgenic animal with a suitable partner, or by in vitro fertilization of eggs and/or sperm obtained from the transgenic animal. Where mating with a partner is to be performed, the partner may or may not be transgenic and/or a knockout; where it is transgenic, it may contain the same or a different transgene, or both. Alternatively, the partner may be a parental line. Where in vitro fertilization is used, the fertilized embryo may be implanted into a surrogate host or incubated in vitro, or both. Using either method, the progeny may be evaluated for the presence of the transgene using methods described above, or other appropriate methods.

VI. Vectors

It is contemplated in the present invention, that virtually any type of vector may be employed in any known or later discovered method to deliver nucleic acids encoding an amino acid, or constructs of nucleic acids encoding a serotonin transporter. Such vectors may be viral or non-viral vectors as described herein, and as known to those skilled in the art. U.S. Pat. Nos. 5,312,734, 5,418,162, and 5,424,185, all incorporated herein by reference, describe nucleic acids, vectors, and host cells used to express various neurotransmitter transporters in cells.

A. Expression Constructs

A vector in the context of the present invention refers to a carrier nucleic acid molecule into which a nucleic acid sequence encoding a serotonin transporter can be inserted for introduction into a cell and thereby replicated. A nucleic acid sequence can be exogenous, in that it is foreign to the cell into which the vector is being introduced; or that the sequence is homologous to a sequence in the cell but positioned within the host cell nucleic acid in which the sequence is ordinarily not found. One of skill in the art would be well equipped to construct a vector through standard recombinant techniques as described in Sambrook et al., 2001; Maniatis et al., 1990; and Ausubel et al., 1994 (each incorporated herein by reference).

It is contemplated in the present invention, that virtually any type of vector may be employed in any known or later discovered method to deliver nucleic acids encoding a serotonin transporter peptide, polypeptide or protein, or constructs thereof. Such vectors may be viral or non-viral vectors as described herein, and as known to those skilled in the art.

An expression vector of the present invention refers to any type of genetic construct comprising a nucleic acid coding for a RNA capable of being transcribed. In some cases, RNA molecules are translated into a protein, polypeptide, or peptide. An expression construct comprising a nucleic acid encoding a serotonin transporter peptide, polypeptide, or protein may comprise a virus or engineered construct derived from a viral genome and may also comprise a natural intron or an intron derived from another gene. In other cases, these sequences are not translated as in the case of antisense molecules or ribozymes production. Expression vectors can contain a variety of control sequences, which refer to nucleic acid sequences necessary for the transcription and possibly translation of an operably linked coding sequence in a particular host cell. In addition to control sequences that govern transcription and translation, vectors and expression vectors may contain nucleic acid sequences that serve other functions as well, and are described herein. Additionally, as set forth above one may also use mutant versions, isoforms, and other variants of any neurotransmitter transporter in the methods of the invention. The foregoing section provides a general description of how exogenous expression may be achieved.

Expression requires that appropriate signals be provided in the vectors, which include various regulatory elements, such as enhancers/promoters from both viral and mammalian sources that drive expression of the genes of interest in host cells. Elements designed to optimize messenger RNA stability and translatability in host cells also are defined. The conditions for the use of a number of dominant drug selection markers for establishing permanent, stable cell clones expressing the products are also provided, as is an element that links expression of the drug selection markers to expression of the polypeptide.

1. Promoters and Enhancers

Expression requires that appropriate signals be provided in the vectors, and which include various regulatory elements, such as enhancers/promoters from both viral and mammalian sources that drive expression of the genes of interest in host cells.

Throughout this application, the term "expression construct" is meant to include any type of genetic construct containing a nucleic acid coding for a gene product in which part or all of the nucleic acid encoding sequence is capable of being transcribed and translated into a polypeptide product. An "expression cassette" is defined as a nucleic acid encoding a gene product under transcriptional control of a promoter. A "promoter" refers to a DNA sequence recognized by the synthetic machinery of the cell, or introduced synthetic machinery, required to initiate the specific transcription of a gene. The phrase "under transcriptional control" means that the promoter is in the correct location and orientation in relation to the nucleic acid to control RNA polymerase initiation and expression of the gene.

The term promoter will be used here to refer to a group of transcriptional control modules that are clustered around the initiation site for RNA polymerase II. Much of the thinking about how promoters are organized derives from analyses of several viral promoters, including those for the HSV thymidine kinase (tk) and SV40 early transcription units. These studies, augmented by more recent work, have shown that promoters are composed of discrete functional modules, each consisting of approximately 7-20 bp of DNA, and containing one or more recognition sites for transcriptional activator or repressor proteins.

At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either co-operatively or independently to activate transcription.

By attaching a tissue-specific or cell-specific promoter region of a nucleic acid to a reporter or a detectable marker, one can obtain tissue-specific or cell-specific expression. The present invention particularly contemplates the use of the serotonin promoter to drive expression of the nucleic acid of interest.

By employing a promoter with well-known properties, the level and pattern of expression of the protein of interest following transfection or transformation can be optimized. Further, selection of a promoter that is regulated in response to specific physiologic signals can permit inducible expression of the gene product. Tables 3 and 4 list several regulatory elements that may be employed, in the context of the present invention, to regulate the expression of the gene of interest.

Additionally, any promoter/enhancer combination (as per the Eukaryotic Promoter Data Base EPDB) may be used to drive expression of the gene. Eukaryotic cells can support cytoplasmic transcription from certain bacterial promoters if the appropriate bacterial polymerase is provided, either as part of the delivery complex or as an additional genetic expression construct.

Enhancers are genetic elements that increase transcription from a promoter located at a distant position on the same molecule of DNA. Enhancers are organized much like promoters. That is, they are composed of many individual elements, each of which binds to one or more transcriptional proteins.

The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization.

TABLE 3

Promoter and/or Enhancer

| Promoter/Enhancer | References |
|---|---|
| Immunoglobulin Heavy Chain | Banerji et al., 1983; Gilles et al., 1983; Grosschedl et al., 1985; Atchinson et al., 1986, 1987; Imler et al., 1987; Weinberger et al., 1984; Kiledjian et al., 1988; Porton et al.; 1990 |
| Immunoglobulin Light Chain | Queen et al., 1983; Picard et al., 1984 |
| T-Cell Receptor | Luria et al., 1987; Winoto et al., 1989; Redondo et al.; 1990 |
| HLA DQ a and/or DQ β | Sullivan et al., 1987 |
| β-Interferon | Goodbourn et al., 1986; Fujita et al., 1987; Goodbourn et al., 1988 |
| Interleukin-2 | Greene et al., 1989 |
| Interleukin-2 Receptor | Greene et al., 1989; Lin et al., 1990 |
| MHC Class II 5 | Koch et al., 1989 |
| MHC Class II HLA-Dra | Sherman et al., 1989 |
| β-Actin | Kawamoto et al., 1988; Ng et al.; 1989 |
| Muscle Creatine Kinase (MCK) | Jaynes et al., 1988; Horlick et al., 1989; Johnson et al., 1989 |
| Prealbumin (Transthyretin) | Costa et al., 1988 |
| Elastase I | Ornitz et al., 1987 |
| Metallothionein (MTII) | Karin et al., 1987; Culotta et al., 1989 |
| Collagenase | Pinkert et al., 1987; Angel et al., 1987 |
| Albumin | Pinkert et al., 1987; Tronche et al., 1989, 1990 |
| α-Fetoprotein | Godbout et al., 1988; Campere et al., 1989 |
| γ-Globin | Bodine et al., 1987; Perez-Stable et al., 1990 |
| β-Globin | Trudel et al., 1987 |
| c-fos | Cohen et al., 1987 |
| c-HA-ras | Triesman, 1986; Deschamps et al., 1985 |
| Insulin | Edlund et al., 1985 |
| Neural Cell Adhesion Molecule (NCAM) | Hirsch et al., 1990 |
| $\alpha_1$-Antitrypsin | Latimer et al., 1990 |
| H2B (TH2B) Histone | Hwang et al., 1990 |
| Mouse and/or Type I Collagen | Ripe et al., 1989 |
| Glucose-Regulated Proteins (GRP94 and GRP78) | Chang et al., 1989 |
| Rat Growth Hormone | Larsen et al., 1986 |
| Human Serum Amyloid A (SAA) | Edbrooke et al., 1989 |
| Troponin I (TN I) | Yutzey et al., 1989 |
| Platelet-Derived Growth Factor (PDGF) | Pech et al., 1989 |
| Duchenne Muscular Dystrophy | Klamut et al., 1990 |
| SV40 | Banerji et al., 1981; Moreau et al., 1981; Sleigh et al., 1985; Firak et al., 1986; Herr et al., 1986; Imbra et al., 1986; Kadesch et al., 1986; Wang et al., 1986; Ondek et al., 1987; Kuhl et al., 1987; Schaffner et al., 1988 |

TABLE 3-continued

Promoter and/or Enhancer

| Promoter/Enhancer | References |
| --- | --- |
| Polyoma | Swartzendruber et al., 1975; Vasseur et al., 1980; Katinka et al., 1980, 1981; Tyndell et al., 1981; Dandolo et al., 1983; de Villiers et al., 1984; Hen et al., 1986; Satake et al., 1988; Campbell and/or Villarreal, 1988 |
| Retroviruses | Kriegler et al., 1982, 1983; Levinson et al., 1982; Kriegler et al., 1983, 1984a, b, 1988; Bosze et al., 1986; Miksicek et al., 1986; Celander et al., 1987; Thiesen et al., 1988; Celander et al., 1988; Choi et al., 1988; Reisman et al., 1989 |
| Papilloma Virus | Campo et al., 1983; Lusky et al., 1983; Spandidos and/or Wilkie, 1983; Spalholz et al., 1985; Lusky et al., 1986; Cripe et al., 1987; Gloss et al., 1987; Hirochika et al., 1987; Stephens et al., 1987 |
| Hepatitis B Virus | Bulla et al., 1986; Jameel et al., 1986; Shaul et al., 1987; Spandau et al., 1988; Vannice et al., 1988 |
| Human Immunodeficiency Virus | Muesing et al., 1987; Hauber et al., 1988; Jakobovits et al., 1988; Feng et al., 1988; Takebe et al., 1988; Rosen et al., 1988; Berkhout et al., 1989; Laspia et al., 1989; Sharp et al., 1989; Braddock et al., 1989 |
| Cytomegalovirus (CMV) | Weber et al., 1984; Boshart et al., 1985; Foecking et al., 1986 |
| Gibbon Ape Leukemia Virus | Holbrook et al., 1987; Quinn et al., 1989 |

TABLE 4

Inducible Elements

| Element | Inducer | References |
| --- | --- | --- |
| MT II | Phorbol Ester (TFA) Heavy metals | Palmiter et al., 1982; Haslinger et al., 1985; Searle et al., 1985; Stuart et al., 1985; Imagawa et al., 1987, Karin et al., 1987; Angel et al., 1987b; McNeall et al., 1989 |
| MMTV (mouse mammary tumor virus) | Glucocorticoids | Huang et al., 1981; Lee et al., 1981; Majors et al., 1983; Chandler et al., 1983; Lee et al., 1984; Ponta et al., 1985; Sakai et al., 1988 |
| β-Interferon | Poly(rI)x Poly(rc) | Tavernier et al., 1983 |
| Adenovirus 5 E2 | E1A | Imperiale et al., 1984 |
| Collagenase | Phorbol Ester (TPA) | Angel et al., 1987a |
| Stromelysin | Phorbol Ester (TPA) | Angel et al., 1987b |
| SV40 | Phorbol Ester (TPA) | Angel et al., 1987b |
| Murine MX Gene | Interferon, Newcastle Disease Virus | Hug et al., 1988 |
| GRP78 Gene | A23187 | Resendez et al., 1988 |
| α-2-Macroglobulin | IL-6 | Kunz et al., 1989 |
| Vimentin | Serum | Rittling et al., 1989 |
| MHC Class I Gene H-2κb | Interferon | Blanar et al., 1989 |
| HSP70 | E1A, SV40 Large T Antigen | Taylor et al., 1989, 1990a, 1990b |
| Proliferin | Phorbol Ester-TPA | Mordacq et al., 1989 |
| Tumor Necrosis Factor α | PMA | Hensel et al., 1989 |
| Thyroid Stimulating Hormone α Gene | Thyroid Hormone | Chatterjee et al., 1989 |

2. Initiation Signals and Internal Ribosome Binding Sites

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

The use of internal ribosome entry sites (IRES) elements may be used to create multigene, or polycistronic, messages. IRES elements are able to bypass the ribosome scanning model of 5' methylated Cap dependent translation and begin translation at internal sites (Pelletier and Sonenberg, 1988). IRES elements from two members of the picornavirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (see U.S. Pat. Nos. 5,925,565 and 5,935,819, herein incorporated by reference).

3. Polyadenylation and Termination Signals

In expression, one will typically include a polyadenylation signal to effect proper polyadenylation of the transcript. The nature of the polyadenylation signal is not believed to be crucial to the successful practice of the invention, and/or any such sequence may be employed. Preferred embodiments include the SV40 polyadenylation signal and/or the bovine growth hormone polyadenylation signal, convenient and/or known to function well in various target cells.

Where a cDNA insert is employed, one will typically desire to include a polyadenylation signal to effect proper polyadenylation of the gene transcript. The nature of the polyadenylation signal is not believed to be crucial to the successful practice of the invention, and any such sequence may be employed such as human growth hormone and SV40 polyadenylation signals.

Also contemplated as an element of the expression cassette is a transcriptional termination site. The vectors or constructs of the present invention will generally comprise at least one termination signal. A "termination signal" or "terminator" is comprised of the DNA sequences involved in specific termination of an RNA transcript by an RNA polymerase. Thus, in certain embodiments a termination signal that ends the production of an RNA transcript is contemplated. A terminator may be necessary in vivo to achieve desirable message levels.

In eukaryotic systems, the terminator region may also comprise specific DNA sequences that permit site-specific cleavage of the new transcript so as to expose a polyadenylation site. This signals a specialized endogenous polymerase to add a stretch of about 200 A residues (polyA) to the 3' end of the transcript. RNA molecules modified with this polyA tail appear to more stable and are translated more efficiently. Thus, in other embodiments involving eukaryotes, it is preferred that that terminator comprises a signal for the cleavage of the RNA, and it is more preferred that the terminator signal promotes polyadenylation of the message. The terminator and/or polyadenylation site elements can serve to enhance message levels and/or to minimize read through from the cassette into other sequences.

Terminators contemplated for use in the invention include any known terminator of transcription described herein or known to one of ordinary skill in the art, including but not limited to, for example, the termination sequences of genes, such as for example the bovine growth hormone terminator or viral termination sequences, such as for example the SV40 terminator. In certain embodiments, the termination signal may be a lack of transcribable or translatable sequence, such as due to a sequence truncation.

These elements can serve to enhance message levels and/or to minimize read through from the cassette into other sequences.

4. Splicing Sites and Origins of Replication

Most transcribed eukaryotic RNA molecules will undergo RNA splicing to remove introns from the primary transcripts. Vectors containing genomic eukaryotic sequences may require donor and/or acceptor splicing sites to ensure proper processing of the transcript for protein expression. (See Chandler et al., 1997), incorporated herein by reference).

In order to propagate a vector in a host cell, it may contain one or more origins of replication sites (often termed "ori"), which is a specific nucleic acid sequence at which replication is initiated. Alternatively an autonomously replicating sequence (ARS) can be employed if the host cell is yeast.

5. Multiple Cloning Sites

Vectors can include a multiple cloning site (MCS), which is a nucleic acid region that contains multiple restriction enzyme sites, any of which can be used in conjunction with standard recombinant technology to digest the vector (see Carbonelli et al., 1999; Levenson et al., 1998; and Cocea, 1997; incorporated herein by reference.) "Restriction enzyme digestion" refers to catalytic cleavage of a nucleic acid molecule with an enzyme that functions only at specific locations in a nucleic acid molecule. Many of these restriction enzymes are commercially available. Use of such enzymes is widely understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

B. Selectable Markers

In certain embodiments of the invention, the cells contain nucleic acid constructs encoding a neurotransmitter transporter may be identified in vitro or in vivo by including a marker in the expression construct. Such markers would confer an identifiable change to the cell permitting easy identification of cells containing the expression construct. Usually the inclusion of a drug selection marker aids in cloning and in the selection of transformants, for example, genes that confer resistance to neomycin, puromycin, hygromycin, DHFR, GPT, zeocin and histidinol are useful selectable markers. Alternatively, enzymes such as herpes simplex virus thymidine kinase (tk) or chloramphenicol acetyltransferase (CAT) may be employed. Immunologic markers also can be employed. The selectable marker employed is not believed to be important, so long as it is capable of being expressed simultaneously with the nucleic acid encoding a gene product. Further examples of selectable markers are well known to one of skill in the art.

C. Host Cells

As used herein, the terms "cell," "cell line," and "cell culture" may be used interchangeably. All of these terms also include their progeny, which is any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organisms that is capable of replicating a vector and/or expressing a heterologous gene encoded by a vector. A host cell can, and has been, used as a recipient for vectors. A host cell may be "transfected" or "transformed," which refers to a process by which exogenous nucleic acid, such as a modified protein-encoding sequence, is transferred or introduced into the host cell. A transformed cell includes the primary subject cell and its progeny.

Host cells may be derived from prokaryotes or eukaryotes, including yeast cells, insect cells, and mammalian cells, depending upon whether the desired result is replication of the vector or expression of part or all of the vector-encoded nucleic acid sequences. Numerous cell lines and cultures are available for use as a host cell, and they can be obtained through the American Type Culture Collection (ATCC), which is an organization that serves as an archive for living cultures and genetic materials (see the atcc website on the internet). An appropriate host can be determined by one of skill in the art based on the vector backbone and the desired result. A plasmid or cosmid, for example, can be introduced into a prokaryote host cell for replication of many vectors. Bacterial cells used as host cells for vector replication and/or expression include DH5, JM109, and KC8, as well as a number of commercially available bacterial hosts such as SURE® Competent Cells and SOLOPACK Gold Cells (STRATAGENE®, La Jolla, Calif.). Alternatively, bacterial cells such as *E. coli* LE392 could be used as host cells for phage viruses. Appropriate yeast cells include *Saccharomyces cerevisiae, Saccharomyces pombe,* and *Pichia pastoris.*

Examples of eukaryotic host cells for replication and/or expression of a vector include HeLa, NIH3T3, Jurkat, 293, Cos, CHO, Saos, and PC12. Many host cells from various cell types and organisms are available and would be known to one of skill in the art. Similarly, a viral vector may be used in conjunction with either a eukaryotic or prokaryotic host cell, particularly one that is permissive for replication or expression of the vector.

D. Viral Vectors

There are a number of ways in which expression vectors may be introduced into cells. In certain embodiments of the invention, the expression vector comprises a virus or engineered vector derived from a viral genome. The ability of certain viruses to enter cells via receptor-mediated endocytosis, to integrate into host cell genome and express viral genes stably and efficiently have made them attractive candidates for the transfer of foreign genes into mammalian cells (Ridgeway, 1988; Nicolas and Rubenstein, 1988; Baichwal and Sugden, 1986; Temin, 1986). The first viruses used as gene vectors were DNA viruses including the papovaviruses (simian virus 40, bovine papilloma virus, and polyoma) (Ridgeway, 1988; Baichwal and Sugden, 1986) and adenoviruses (Ridgeway, 1988; Baichwal and Sugden, 1986). These have a relatively low capacity for foreign DNA sequences and have a restricted host spectrum. Furthermore, their oncogenic potential and cytopathic effects in permissive cells raise safety concerns. They can accommodate only up to 8 kb of foreign genetic material but can be readily introduced in a variety of cell lines and laboratory animals (Nicolas and Rubenstein, 1988; Temin, 1986).

The retroviruses are a group of single-stranded RNA viruses characterized by an ability to convert their RNA to double-stranded DNA in infected cells; they can also be used as vectors. Adenoviruses are also typically used as vectors due to their mid-sized genome, ease of manipulation, high titer, wide target cell range and high infectivity. The use of retroviral and adenoviral vectors in eukaryotic gene expression and gene therapy are well known in the art.

Other viral vectors may also be employed as expression constructs in the present invention. Vectors derived from viruses such as vaccinia virus (Ridgeway, 1988; Baichwal and Sugden, 1986; Coupar et al., 1988) adeno-associated virus (AAV) (Ridgeway, 1988; Baichwal and Sugden, 1986; Hermonat and Muzycska, 1984) and herpesviruses may be employed. These vectors offer several attractive features for various mammalian cells (Friedmann, 1989; Ridgeway, 1988; Baichwal and Sugden, 1986; Coupar et al., 1988; Horwich et al., 1990).

VII. Methods of Transfer of Nucleic Acids Encoding a Serotonin Transporter

There are a number of suitable methods by which nucleic acids encoding amino acid sequences of the serotonin transporter may be introduced or delivered to cells. Virtually any method by which nucleic acids (e.g., DNA, including viral and nonviral vectors) can be introduced into a cell, or an organism may be employed with the current invention, as described herein or as would be known to one of ordinary skill in the art. Several methods for the transfer of expression constructs into mammalian cells include, but are not limited to: direct delivery of DNA by injection (U.S. Pat. Nos. 5,994,624, 5,981,274, 5,945,100, 5,780,448, 5,736,524, 5,702,932, 5,656,610, 5,589,466 and 5,580,859, each incorporated herein by reference), including microinjection (Harlan and Weintraub, 1985; U.S. Pat. No. 5,789,215, incorporated herein by reference); by electroporation (U.S. Pat. No. 5,384,253, incorporated herein by reference; Tur-Kaspa et al., 1986; Potter et al., 1984); by calcium phosphate precipitation (Graham and Van Der Eb, 1973; Chen and Okayama, 1987; Rippe et al., 1990); by using DEAE-dextran followed by polyethylene glycol (Gopal, 1985); by direct sonic loading (Fechheimer et al., 1987); by liposome mediated transfection (Nicolau and Sene, 1982; Fraley et al., 1979; Nicolau et al., 1987; Wong et al., 1980; Kaneda et al., 1989; Kato et al., 1991) and receptor-mediated transfection (Wu and Wu, 1987; Wu and Wu, 1988); by microprojectile bombardment (PCT Application WO 94/09699 and 95/06128; U.S. Pat. Nos. 5,610,042; 5,322,783 5,563,055, 5,550,318, 5,538,877 and 5,538,880, and each incorporated herein by reference); by agitation with silicon carbide fibers (Kaeppler et al., 1990; U.S. Pat. Nos. 5,302,523 and 5,464,765, each incorporated herein by reference); or by PEG-mediated transformation of protoplasts (Omirulleh et al., 1993; U.S. Pat. Nos. 4,684,611 and 4,952,500, each incorporated herein by reference); by desiccation/inhibition-mediated DNA uptake (Potrykus et al., 1985), and any combination of such methods.

VIII. Pharmaceutical Formulations

The present invention also contemplates the use of the candidate substance(s) identified by the screening method as therapeutic agents for the treatment of neurological diseases. The therapeutic candidate substance(s) of the serotonin transporter identified by the screening methods of the invention, may be prepared in pharmaceutical compositions. Generally, this will entail preparing compositions that are essentially free of pyrogens, as well as other impurities that could be harmful to humans or animals.

One will generally desire to employ appropriate salts and buffers. Aqueous compositions of the present invention comprise an effective amount of the neurotransmitter transporter modulator dissolved or dispersed in a pharmaceutically acceptable carrier or aqueous medium. The phrase "pharmaceutically or pharmacologically acceptable" refer to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well know in the art. Supplementary active ingredients also can be incorporated into the compositions.

Administration of these compositions according to the present invention will be via any common route so long as the target tissue is available via that route. This includes administration may be by systemic or parenteral methods including intravenous injection, intracerebral, intradermal, subcutaneous, intramuscular, intraperitoneal methods. Direct administration by local injection into the site of disease is also contemplated. Depending on the nature of the modulator administration may also be via oral, nasal, buccal, rectal, vaginal or topical. Such compositions would normally be administered as pharmaceutically acceptable compositions, described supra.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial an antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The compositions of the present invention may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The composition may be formulated as a "unit dose." For example, one unit dose could be dissolved in 1 ml of isotonic NaCl solution and either added to 1000 ml of hypodermoclysis fluid or injected at the proposed site of infusion, (see for example, "Remington's Pharmaceutical Sciences" $15^{th}$ Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

IX. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Site-Directed Mutagenesis and Construction of Mutant Plasmids

Mutation of hSERT and mSERT in pcDNA3 was performed using the Stratagene QuikChange kit. Subsequent sequencing (Center for Molecular Neuroscience Neurogenomics and Sequencing Core Facility) confirmed the presence of only the intended mutation. hSERT I172M mutant cDNA was also subcloned into the pBABE to generate stable transformants in HEK-293 cells, achieved following selection in 2 μg/mL puromycin.

Example 2

5-HT Transport Measurements

HeLa and HEK-293 cells, maintained at 37° C. in a 5% $CO_2$ humidified incubator, were grown in complete medium (DMEM, 10% FBS, 2 mM L-glutamine, 100 units/ml penicillin, and 100 μg/ml streptomycin). For initial evaluation of mutant transporter activity, cells were plated at a density of 100,000 cells per well in 24 well culture plates. Cells were infected with a vaccinia virus carrying the T7 RNA polymerase in OptiMEM plus 55 mM β-mercaptoethanol for 30 minutes at 37° C., after which SERT constructs were transfected with 3 μl of Fugene 6 per μg of DNA, also in OptiMEM medium. Following transfection (16 hours), cells were washed with KRH assay buffer (120 mM NaCl, 4.7 mM KCl, 2.2 mM $CaCl_2$, 1.2 mM $MgSO_4$, 1.2 mM $KH_2PO_4$, 10 mM HEPES, pH 7.4) and assayed for $[^3H]$-5-HT (5-hydroxy$[^3H]$ tryptamine trifluoroacetate, Amersham Pharmacia Biotech) transport. The cells were washed in assay buffer followed by a preincubation in 37° C. assay buffer containing 1.8 g/L glucose. Cells were incubated for 10 minutes at 37° C. with 20 nM $[^3H]$-5-HT, 100 μM pargyline, and 100 μM L-ascorbate. Assays maintained linearity under these conditions for up to 15 minutes. Saturation kinetics for derivation of 5-HT KM and $V_{MAX}$ were established in 24 well plates as described above except serial dilutions (5 to 0.035 μM) of a hot/cold mix of 5HT with constant specific activity was used. Transport assays were terminated by washing 3 times with ice-cold assay buffer and cells were dissolved in Microscint 20 (Packard) scintillation fluid or 1% SDS. Transport assays on stable cells were performed as described above for transient transfectants 1 day after plating of 20,000 cells in 96 well microwell plates or 100,000 cells in 24 well plates coated with 1 mg/ml poly D-lysine. The extent of $[^3H]$-5-HT accumulated was determined by liquid scintillation counting on a Packard TopCount System or a Beckman liquid scintillation counter. Uptake in mock-transfected cells was subtracted from SERT-transfected cells to determine specific uptake. Non-transfected cells exhibited comparable uptake to assays performed in the presence of 1 μM paroxetine or 1 μM RTI-55. For competitive uptake assays, cells were processed as above except prior to addition of 20 nM $[^3H]$5HT cells were incubated for 10 minutes with various concentrations of inhibitor compounds. The resulting data was normalized to percent uptake of wildtype control and analyzed by a non-linear competition binding equation (Prism 3 or Prism 4 for Mac, Graphpad Software). Ki values were determined by application of the Cheng and Prusoff equation. All experiments were performed in triplicate and repeated in 3 or more separate assays.

Figure 2:
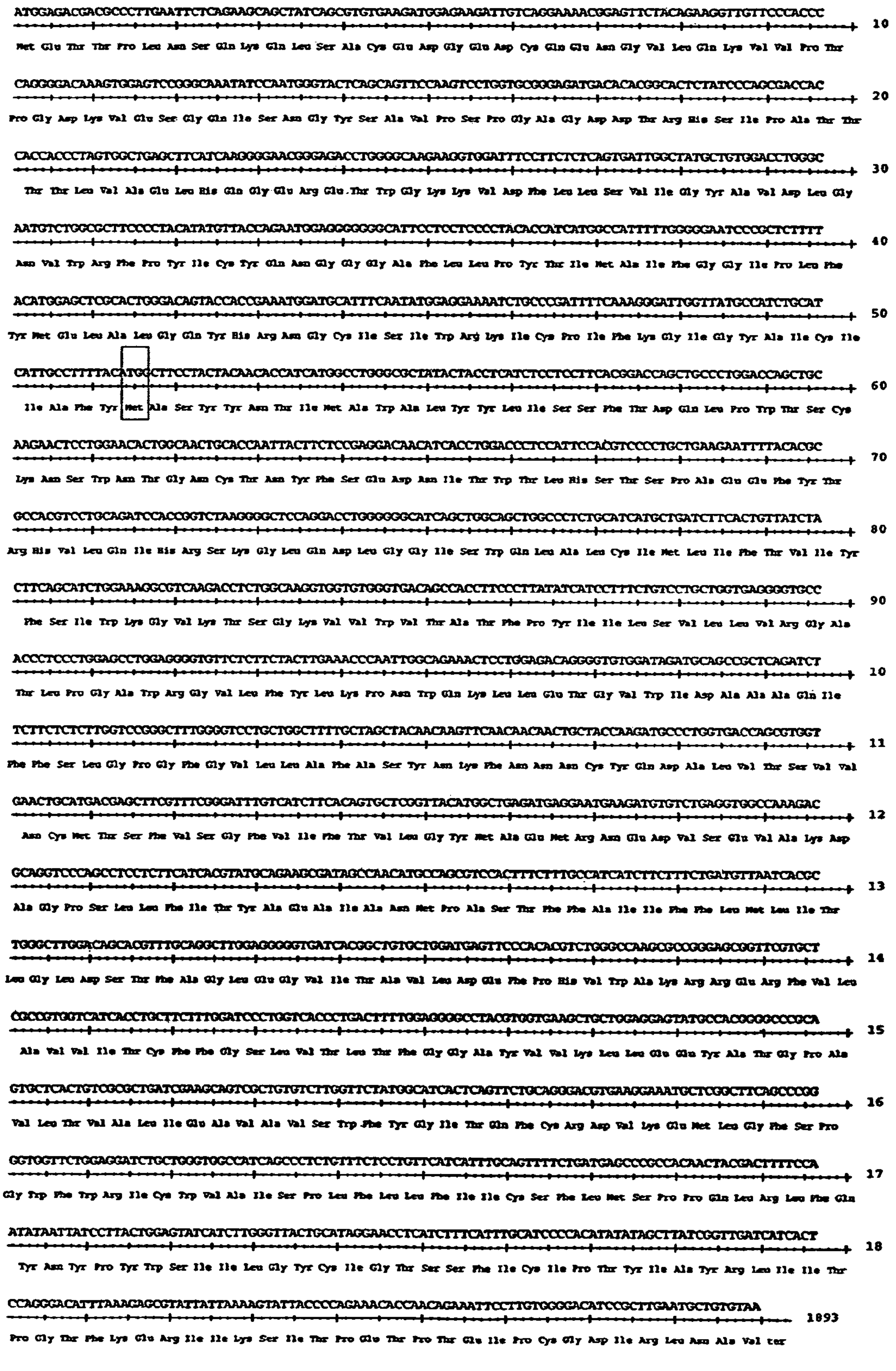
FIG. 2—I172M human serotonin transporter (SEQ ID NOS:1-2).

Residue (I172) has been identified in transmembrane segment 3 (TM3) in hSERT as a determinant for binding of many SERT inhibitors. Mutation of this isoleucine to methionine, the homologous residue in dSERT, has no obvious detrimental effect on 5HT transport (FIGS. 1-3). However, the mutant displays a dramatic loss in recognition of several SERT inhibitors with marked increases evident in the $IC_{50}$ values for citalopram, RTI-55, cocaine, nisoxetine, mazindol, and nomifensene (Table 5). In contrast, no effect is observed on the $IC_{50}$ of all SERT substrates tested including 5HT, tryptamine and MDMA. Two inhibitors, paroxetine and tianeptine also exhibited little if any change in uptake inhibitory potency in the I172M mutant. The effect of this residue on inhibitor binding does not appear to be specific to hSERT as the homologous mutation (I172M) constructed in mouse SERT displays similar changes in inhibitor potency (FIGS. 2 and 3). Importantly, cysteine mutagenesis studies on TM3 of hSERT suggested that I172 was involved in binding of 5HT and cocaine. Other mutants have also been identified as demonstrated in Table 5 as serotonin transporter mutants.

TABLE 5

| | $EC_{50}$(μM) | | |
|---|---|---|---|
| Compound | WT | I172M | Fold Δ |
| | Human | | |
| Substrate | | | |
| 5HT | 2.7 | 3.7 | 1 |
| Tryptamine | 0.2 | 0.2 | 0 |
| MDMA | 0.7 | 0.8 | 1 |
| Alpha-methylserotonin maleate | 2.2 | 2.3 | 1 |
| 7-hydroxytryptamine | 1.4 | 1.1 | 1 |
| 5,6,7 trihydroxytryptamine | 14.3 | 2.7 | .2 |
| Inhibitor | | | |
| Mazindol | 2.9 | 36 | 12 |
| Nomifensene | 2.7 | 32 | 12 |
| Fluoxetine | 0.007 | 0.96 | 137 |
| Cocaine | 0.56 | 80 | 143 |
| Nisoxetine | 1.36 | 197 | 145 |
| RTI-55 | 0.0007 | 0.12 | 176 |
| Clomipramine | .0029 | 0.69 | 238 |
| Citalopram | .013 | 7.9 | 607 |
| Paroxetine | 0.00038 | 0.001 | 2.6 |
| Tianeptine | 3.8 | 3.1 | 1 |
| Amytryptyline | .095 | .06 | 1 |
| | Mouse | | |
| Substrate | | | |
| 5HT | 0.6 | 1 | 1 |
| Inhibitor | | | |
| Tianeptine | 3.8 | 3.1 | 1 |
| Clomipramine | 0.024 | 1.9 | 79 |
| Citalopram | 0.0074 | 13 | 1756 |

| HseRT Mutant | | | $IC_{50}$ | Citalopram |
|---|---|---|---|---|
| | Nucleic Acid | Amino Acid | 5HT (μM) | (nM) |
| WT | SEQ ID NO: 1 | SEQ ID NO: 2 | 0.3 | 2.1 |
| I172M | SEQ ID NO: 3 | SEQ ID NO: 4 | 3.7 | 7900 |
| I172A | SEQ ID NO: 9 | SEQ ID NO: 10 | 1 | 3.7 |
| I172F | SEQ ID NO: 11 | SEQ ID NO: 12 | 3.3 | 4600 |
| I172Q | SEQ ID NO: 13 | SEQ ID NO: 14 | 7.6 | 160 |
| I172V | SEQ ID NO: 15 | SEQ ID NO: 16 | 0.6 | 56 |

| mSERT Mutant | Nucleic Acid | Amino Acid |
|---|---|---|
| WT | SEQ ID NO: 5 | SEQ ID NO: 6 |
| I172M | SEQ ID NO: 7 | SEQ ID NO: 8 |

Example 3

Generating Transgenic Mice

The present invention also provides a method of producing a transgenic mouse having a serotonin transporter containing a mutation at position 172 from an isoleucine to a methionine. The wild-type SERT sequence may be isolated by genomic library screening or by whole genome PCR. Initially, a DNA construct containing a targeting segment which consists essentially of the nucleotide sequence of the mouse serotonin transporter is made. A portion of the targeting fragment may be modified by integrating or replacing it with a marker sequence not normally found in the serotonin transporter gene. The mutant is engineered into the genomic DNA and verify by DNA sequencing.

The construct will then be introduced into a mouse embryonic stem cells for the purpose of integrating the fragment into the mouse genome. The recombinant stem cells produced are selected and incorporated into a mouse blastocyst to form a chimeric embryo. This is implanted into a pseudopregnant mouse and allowed to develop into a viable offspring. The offspring produced are screened to identify heterozygous mice containing the I172M serotonin transporter. These mice are then bred to develop homozygous transgenic mice having a phenotype characterized by the nucleic acid sequence encoding a I172M serotonin transporter as in SEQ ID NO: 3, SEQ ID NO: 7, SEQ ID NO: 9, SEQ ID NO: 11, SEQ ID NO: 13, SEQ ID NO: 15, or SEQ ID NO: 17.

Example 4

Testing of the SERT Transporter In Vivo

As described in the present invention, transgenic mice may be used to test agents that block serotonin transport. The sensitivity of the mice to the serotonin transporter blocker or antidepressant would be predictive to the efficacy of these drugs or agents in humans. These tests may employ the Porsolt forced swim test which will determine mobility or immobility, in a mouse after administration of the serotonin transporter blocker. Other tests that may be employed include the light/dark test and the elevated plus-maze test which would test for whether the drug or agent diminishes anxiety in mice. It is also contemplated that in vivo microdialysis may be used to measure release of serotonin in the mouse brain in response to a stimuli such as the novel serotonin transporter blockers of the invention. The effect of specific serotonin reuptake inhibitors (SSRI) may also be assessed by measuring the metabolic changes in the serotonin transporter.

Example 5

Inhibition of 5HT Transport

Site-directed mutagenesis and construction of mutant plasmids. Mutation of hSERT I172M in pcDNA3 was performed using the Stratagene QuikChange kit. Subsequent sequencing (Center for Molecular Neuroscience Neurogenomics and Sequencing Core Facility) confirmed the presence of the intended Y95F mutation in the I172M mutant background. The nucleic acid sequence encoding a Y95F/I172M serotonin transporter as described herein is represented as SEQ ID NO: 17 and the amino acid sequence as SEQ ID NO: 18. The nucleic acid sequence encoding a Y95F mutant is represented as SEQ ID NO: 19 and the amino acid sequence as SEQ ID NO: 20.

5-HT transport measurements. HeLa cells maintained at 37° C. in a 5% $CO_2$ humidified incubator, were grown in complete medium (DMEM, 10% FBS, 2 mM L-glutamine, 100 units/ml penicillin, and 100 μg/ml streptomycin). For initial evaluation of mutant transporter activity, cells were plated at a density of 100,000 cells per well in 24 well culture plates. Cells were transfected with SERT mutant or wild-type constructs with 3 μl of Fugene 6 per μg of DNA pre-mixed in OptiMEM medium. Following transfection (16 hours), cells were washed with KRH assay buffer (120 mM NaCl, 4.7 mM KCl, 2.2 mM $CaCl_2$, 1.2 mM $MgSO_4$, 1.2 mM $KH_2PO_4$, 10 mM HEPES, pH 7.4) and assayed by competitive uptake assays where cells were preincubated for 10 min at 37° C. in assay buffer containing 1.8 g/L glucose and various concentrations of inhibitor compounds. This was followed by a 10 min incubation with 20 nM $[^3H]$-5-HT (5-hydroxy$[^3H]$ tryptamine trifluoroacetate, Amersham Pharmacia Biotech), 100 μM pargyline, and 100 μM L-ascorbate to measure transport. Competitive uptake assays were terminated by washing 3 times with ice-cold assay buffer and cells were dissolved in Microscint 20 (Packard) scintillation fluid. The extent of $[^3H]$-5-HT accumulated was determined by liquid scintillation counting on a Packard TopCount System.

The resulting data was normalized to percent uptake of wild-type control and analyzed by a non-linear competition binding equation (Prism 4 for Mac, Graphpad Software) for $[^3H]$-5-HT (5-hydroxy$[^3H]$tryptamine trifluoroacetate, Amersham Pharmacia Biotech). Uptake in mock-transfected cells was subtracted from SERT-transfected cells to determine specific uptake. For Ki values were determined by application of the Cheng and Prusoff equation. All experiments were performed in triplicate and repeated in 3 or more separate assays.

FIGS. 4A-4D show that, when combined with another mutant (a Y95F substitution in transmembrane domain; Barker et al., 1998), about a 4-order of magnitude potency shift was observed for the SSRI citalopram whereas serotonin (5HT) recognition appeared normal. FIGS. 4A-4D show the potency of either 5HT, citalopram, R-citalopram, or S-citalopram for inhibition of $[^3H]$-5-HT transport in cells transfected with the respective wild-type or mutant hSERT cDNA.

Figure 4A:
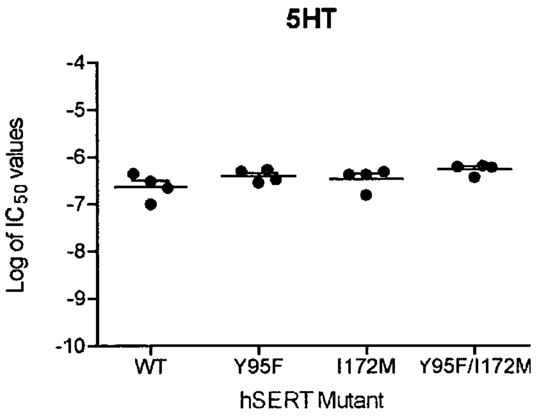
FIGS. 4A-4D—hSERT I172M and Y95F synergize to diminish antidepressant recognition. Inhibitor potency of racemic citalopram (FIG. 4A); R-citalopram (R-CIT; also known as Celexa), (FIG. 4B); S-citalpram (S-CIT; also known as Lexapro), (FIG. 4C); and 5HT (FIG. 4D) on tritiated 5HT uptake when tested with wildtype and mutant hSERT expressing HeLa cells. $IC_{50}$ values from individual experiments are plotted on each graph vs hSERT construct with error bars representing the SEM.
Figure 4B:
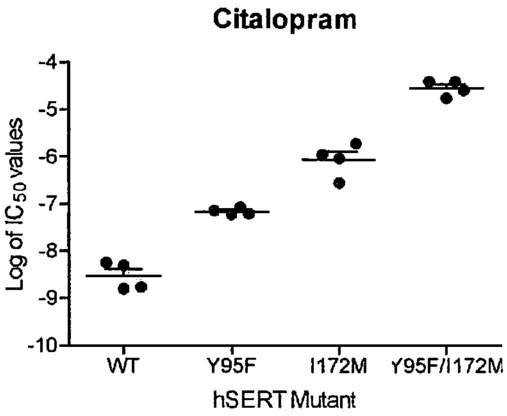
Figure 4C:
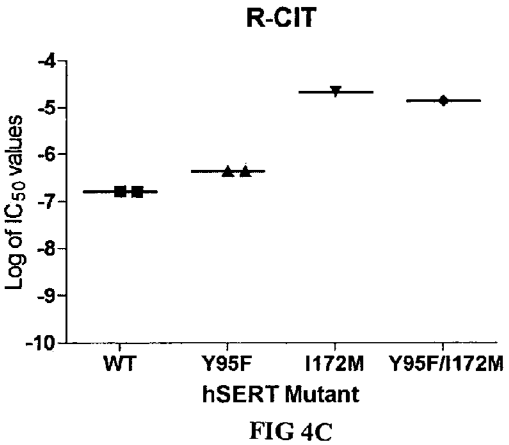
Figure 4D:
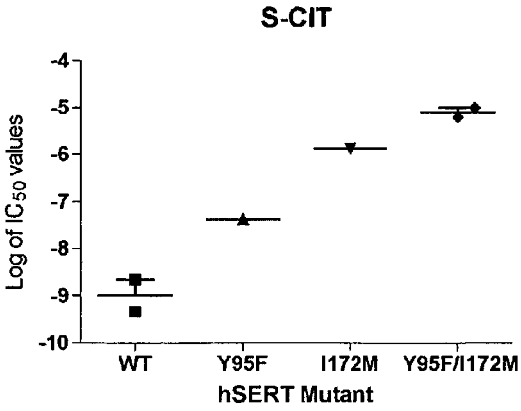

Inhibitor potency of racemic citalopram (FIG. 4A); R-citalopram (R-CIT; also known as Celexa), (FIG. 4B); S-citalpram (S-CIT; also known as Lexapro), (FIG. 4C); and 5HT (FIG. 4D) was observed on tritiated 5HT uptake when tested with wildtype and mutant hSERT expressing HeLa cells. $IC_{50}$ values from individual experiments are plotted on each graph vs hSERT construct with error bars representing the SEM.

Thus, the data demonstrate that added selectivity can be gained when the I172M mutation is used in the context of other mutations to further impact traditional antidepressant action. For example, a greater loss of SSRI recognition was observed when the double mutant I172M/Y95F is made. This implies that the mutation can be used on its own or in the context of other mutants to identify novel SERT blockers and/or non-SERT targets of existing drugs. This therefore provides one of ordinary skill in the art, the choice of screening I172M/Y95F double mutants for novel SERT blockers (using all existing technologies).

Example 6

Testing of Novel Agents In Vivo

Traditional assays have made use of either native SERT or cloned SERT expressed in cells. The present invention on the other hand provides a novel form of SERT that lacks high affinity recognition of SSRIs. This novel SERT is utilized for the discovery of novel drugs that block SERT in a distinct way, and to identify novel modes of action of SSRIs in vivo. These assays may be accomplished by using mouse models as discussed herein.

In one instance, the generation of a "knock-in" animal carrying the I172M mutation, may be utilized in the present invention for testing drugs using native preparations that carry the mutant transporter and also investigate novel pathways for SSRI action that cannot be detected otherwise.

In another instance, a mouse generated with the I172M mutation, may be utilized in the present invention by providing an SSRI to the mouse and then investigating non-SERT actions of the drug, which may be important in side-effects or even therapeutic effects that have so far been attributed to SERT blockade but which may be due to something else.

Therefore, the present invention provides one of ordinary skill in the art, the ability to screen a mouse carrying the I172MJY95F double mutants for non-SERT targets of known drugs.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 4,554,101
U.S. Pat. No. 4,873,191
U.S. Pat. No. 5,175,384
U.S. Pat. No. 5,175,385
U.S. Pat. No. 5,252,479
U.S. Pat. No. 5,312,734
U.S. Pat. No. 5,418,162
U.S. Pat. No. 5,424,185
U.S. Pat. No. 5,530,179
U.S. Pat. No. 5,565,186
U.S. Pat. No. 5,612,486
U.S. Pat. No. 5,625,125
U.S. Pat. No. 5,639,457
U.S. Pat. No. 5,925,565
U.S. Pat. No. 5,935,819
Angel et al., *Mol. Cell. Biol.,* 7:2256, 1987a.
Angel et al., *Cell,* 49:729, 1987b.
Apparsundaram et al., *J. Neurosci.,* 17(8):2691-2702, 1997.
Ashton, In: *Brain Systems, Disorders, and Psychotropic Drugs,* 283-330, Oxford University Press, NY, 1987.
Aston-Jones et al., *Biol. Psychiatry,* 46:1309-1320, 1999.
Atchison and Perry, *Cell,* 46:253, 1986.
Atchison and Perry, *Cell,* 48:121, 1987.

Ausubel et al., In: *Current Protocols in Molecular Biology,* John, Wiley and Sons, Inc, New York, 1994.
Axelrod and Kopin, *Prog. Brain Res.,* 31, 21-32, 1969.
Baichwal and Sugden, In: *Gene Transfer,* Kucherlapati (ed.), NY, Plenum Press, 117-148, 1986.
Banerji et al., *Cell,* 27(2 Pt 1):299-308, 1981.
Banerji et al., *Cell,* 33(3):729-740, 1983.
Bannon, *Eur. Neuropsychopharmacol.,* 11(6):449-55, 2001.
Barker and Blakely, *Mol. Pharmacol.,* 50(4):957-65, 1996.
Barker et al., *J. Biol. Chem.,* 273(31):19459-19468, 1998.
Barnes, *Science,* 241:1029-1030, 1988.
Benvenisty and Neshif, *Proc. Natl. Acad. Sci. USA,* 83(24): 9551-9555, 1986.
Berkhout et al., *Cell,* 59:273-282, 1989.
Biederman and Spencer, *Biol. Psychiatry,* 46:1234-1242, 1999.
Blakely and Apparsundaram, *Adv. Pharmacol.,* 42:206-210, 1998.
Blakely et al., *Nature,* 354:66-70, 1991.
Blanar et al., *EMBO J.,* 8:1139, 1989.
Blundell, *Appetite,* 7(1):39-56 1986.
Bodine and Ley, *EMBO J.,* 6:2997, 1987.
Bonisch and Harder, *Naunyn Schmiedebergs Arch. Pharmacol.,* 334:403-411, 1986.
Bonisch, *Naunyn Schmiedebergs Arch. Pharmacol.,* 327:267-272, 1984.
Boshart et al., *Cell,* 41:521, 1985.
Bosze et al., *EMBO J.,* 5(7):1615-1623, 1986.
Braddock et al., *Cell,* 58:269, 1989.
Bradley et al., *Nature,* 309:255-258, 1984.
Briley et al., *Science,* 209(4453)303-305, 1980.
Briley et al., *Trends Pharmacol Sci.,* 14(11)396-397, 1993.
Brinster et al., *Proc. Natl. Acad. Sci. USA,* 82(13):4438-4442, 1985.
Bruns, *Methods Enzymol.,* 296:593-607, 1998.
Bulla and Siddiqui, *J. Virol.,* 62:1437, 1986.
Campbell and Villarreal, *Mol. Cell. Biol.,* 8:1993, 1988.
Campere and Tilghman, *Genes and Dev.,* 3:537, 1989.
Campo et al., *Nature,* 303:77, 1983.
Carbonelli et al, *FEMS Microbiol. Lett.,* 177(1):75-82, 1999.
Celander and Haseltine, *J. Virology,* 61:269, 1987.
Celander et al., *J. Virology,* 62:1314, 1988.
Chandler et al., *Cell,* 33:489, 1983.
Chandler et al., *Proc. Natl. Acad. Sci. USA,* 94(8):3596-601, 1997.
Chang et al., *Hepatology,* 14:134A, 1991.
Chang et al., *Mol. Cell. Biol.,* 9:2153, 1989.
Chatterjee et al., *Proc Natl. Acad Sci. USA,* 86:9114, 1989.
Choi et al., *Cell,* 53:519, 1988.
Clarkson, et al., *Circulation,* 87:950-962, 1993.
Cocea, *Biotechniques,* 23(5):814-816, 1997.
Coffin, In: *Virology,* Fields et al. (Eds.), Raven Press, NY, 1437-1500, 1990.
Cohen et al., *J. Cell. Physiol.,* 5:75, 1987.
Corey et al., *Proc. Natl. Acad. Sci. USA,* 91:1188-1192, 1994.
Costa et al., *Mol. Cell. Biol.,* 8:81, 1988.
Couch et al., *Am. Rev. Resp. Dis.,* 88:394-403, 1963.
Coull et al., *Neuroimage,* 10:705-715, 1999.
Coupar et al., *Gene,* 68:1-10, 1988.
Cripe et al., *EMBO J.,* 6:3745, 1987.
Culotta and Harrer, *Mol. Cell. Biol.,* 9:1376, 1989.
Dandolo et al., *J. Virology,* 47:55-64, 1983.
De Oliveira et al., *Neuropharmacology,* 28:823-828, 1989.
De Villiers et al., *Nature,* 312(5991):242-246, 1984.
DeFelice and Galli, *Adv. Pharmacol.,* 42:186-190, 1998.
Deschamps et al., *Science,* 230:1174-1177, 1985.
Dow and Kline, *Ann. Clin. Psychiatry,* 9:1-5, 1997.
Dubensky et al., *Proc. Natl. Acad. Sci. USA,* 81:7529-7533, 1984.
Edbrooke et al., *Mol. Cell. Biol.,* 9:1908, 1989.
Edlund et al., *Science,* 230:912-916, 1985.
Edwards, *Ann Neurol.,* November;34(5):638-45, 1993.
European Appl. EPO 0 273 085
Evans et al., *Nature,* 292:154-156, 1981.
Fechheimer et al., *Proc. Natl. Acad. Sci. USA,* 84:8463-8467, 1987.
Feng and Holland, *Nature,* 334:6178, 1988.
Ferkol et al, *FASEB J.,* 7:1081-1091, 1993.
Firak and Subramanian, *Mol. Cell. Biol.,* 6:3667, 1986.
Fleckenstein et al., *Eur. J. Pharmacol.,* 382:45-49, 1999.
Foecking and Hofstetter, *Gene,* 45(1):101-105, 1986.
Friedmann, *Science,* 244:1275-1281, 1989.
Fujita et al., *Cell,* 49:357, 1987.
Gainetdinov et al., *J. Neurochem.,* 69:1322-1325, 1997.
Galli et al., *J. Exp. Biol.,* 198(10):2197-2212, 1995.
Galli et al., *PNAS,* 93:8671-8676, 1998.
Ghosh and Bachhawat, In: *Liver Diseases, Targeted Diagnosis and Therapy Using Specific Receptors and Ligands.* Wu et al. (Eds.), Marcel Dekker, NY, 87-104, 1991.
Ghosh-Choudhury et al., *EMBO J.,* 6:1733-1739, 1987.
Gill et al., *Alcoholism II,* 444-449, 1987.
Gilles et al., *Cell,* 33:717, 1983.
Giros et al., *Mol. Pharmacol.,* 42(3):383-390, 1992.
Giros et al., *Nature,* 379(6566):606-612, 1996.
Glassman et al., *J. Nerv. Ment. Dis.,* 173:573-576, 1985.
Gloss et al, *EMBO J.,* 6:3735, 1987.
Godbout et al., *Mol. Cell. Biol.,* 8:1169, 1988.
Gomez-Foix et al., *J. Biol. Chem.,* 267:25129-25134, 1992.
Goodboum and Maniatis, *Proc. Natl. Acad. Sci. USA,* 85:1447, 1988.
Goodboum et al., *Cell,* 45:601, 1986.
Gopal, *Mol. Cell Biol.,* 5:1188-1190, 1985.
Gossler et al., *Proc. Natl. Acad. Sci. USA,* 83: 9065-9069, 1986.
Graham and Prevec, In: *Methods in Molecular Biology: Gene Transfer and Expression Protocol,* Murray (Ed.), Humana Press, Clifton, N.J., 7:109-128, 1991.
Graham et al., *J. Gen. Virl.,* 36(1):59-74, 1977.
Greene et al., *Immunology Today,* 10:272, 1989
Grosschedl and Baltimore, *Cell,* 41:885, 1985.
Grunhaus et al., *Seminar in Virology,* 200(2):535-546, 1992.
Gu et al., *J. Biol. Chem.,* 269:7124-7130, 1994.
Hadrich et al., *J. Med. Chem.,* 42:3101-3108, 1999.
Harland and Weintraub, *J. Cell Biol.,* 101:1094-1099, 1985.
Hartzell, *J. Cell Biol.,* 86:6-20, 1980.
Haslinger and Karin, *Proc. Natl. Acad. Sci. USA,* 82:8572, 1985.
Hatfield and McGaugh, *Neurobiol. Learn. Mem.,* 71:232-239, 1999.
Hauber and Cullen, *J. Virology,* 62:673, 1988.
Hen et al., *Nature,* 321:249, 1986.
Hensel et al., *Lymphokine Res.,* 8:347, 1989.
Hermonat and Muzycska, *Proc. Natl. Acad. Sci. USA,* 81:6466-6470, 1984.
Herr and Clarke, *Cell,* 45:461, 1986.
Herrera and Banner, *J. Neurocytol.,* 19:67-83, 1990.
Herrera et al., *J. Neurocytol.,* 19:85-99, 1990.
Hersdorffer et al., *DNA Cell Biol.,* 9:713-723, 1990.
Herz and Gerard, *Proc. Natl. Acad. Sci. USA,* 90:2812-2816, 1993.
Hirochika et al., *J. Virology,* 61:2599, 1987.
Hirsch et al., *Mol. Cell. Biol.,* 10: 1959, 1990.

Hogan et al., In: *Manipulating the Mouse Embryo:* A Laboratory Manual, $2^{nd}$ ed., Cold Spring Harbor Laboratory Press, 1994.
Hogan et al., In: Manipulating the Mouse Embryo: A Laboratory Manual, 2nd ed., Cold Spring Harbor Laboratory Press, 1996.
Hohage et al., *J. Pharmacol. Exp. Ther.,* 286:305-310, 1998.
Holbrook et al., *J. Virology,* 157:211, 1987.
Horlick and Benfield, *Mol. Cell. Biol.,* 9:2396, 1989.
Horwich et al., *J. Virology,* 64:642-650, 1990.
Huang et al., *Cell,* 27:245, 1981.
Hug et al., *Mol. Cell. Biol.,* 8:3065, 1988.
Hwang et al., *Mol. Cell. Biol.,* 10:585, 1990.
Imagawa et al., *Cell,* 51:251, 1987.
Imbra and Karin, *Nature,* 323:555, 1986.
Imler et al., *Mol. Cell. Biol,* 7:2558, 1987.
Imperiale and Nevins, *Mol. Cell. Biol.,* 4:875, 1984.
Iversen et al., *J. Pharmacol. Exp. Ther.,* 157:509-516, 1967.
Jacob et al., *Circulation,* 99:1706-1712, 1999.
Jaenich, *Proc. Natl. Acad. Sci. USA,* 73:1260-1264, 1986.
Jaenisch, *Science* 240:1468-1474, 1988.
Jahner et al.,*Nature,* 298:623-628, 1982.
Jahner et al., *Proc. Natl. Acad. Sci. USA,* 82:6927-6931, 1985.
Jakobovits et al., *Mol. Cell. Biol.,* 8:2555, 1988.
Jameel and Siddiqui, *Mol. Cell. Biol.,* 6:710, 1986.
Jaynes et al., *Mol. Cell. Biol.,* 8:62, 1988.
Johnson et al., *Mol. Cell. Biol.,* 9:3393, 1989.
Jones and Shenk, *Cell,* 13:181-188, 1978.
Jones, Prog. *Brain Res.,* 88:381-394, 1991.
Kadesch and Berg, *Mol. Cell. Biol.,* 6:2593, 1986.
Kaneda et al., *Science,* 243:375-378, 1989.
Karin et al., *Mol. Cell. Biol.,* 7:606, 1987.
Karlsson et al., *EMBO J.,* 5:2377-2385, 1986.
Katinka et al., *Cell,* 20:393, 1980.
Kato et al, *J. Biol. Chem.,* 266:3361-3364, 1991.
Kawamoto et al., *Mol. Cell. Biol.,* 8:267, 1988.
Kawarai et al., *Gene,* August 11;195(1):11-8 1997.
Kiledjian et al., *Mol Cell. Biol.,* 8:145, 1988.
Kitayama et al., *Neurosci. Lett.,* 312(2):108-112, 2001.
Klamut et al., *Mol. Cell. Biol.,* 10:193, 1990.
Koch et al., *Mol. Cell. Biol.,* 9:303, 1989.
Koella, *Neuronal Serotonin,* Osborne et al. (eds.), 153-170, 1988.
Kriegler and Botchan, In: *Eukaryotic Viral Vectors,* Gluzman, ed., Cold Spring Harbor: Cold Spring Harbor Laboratory, NY, 1982.
Kriegler and Botchan, *Mol. Cell. Biol.,* 3:325, 1983.
Kriegler et al., *Cell,* 38:483, 1984.
Kriegler et al., *Cell,* 53:45, 1988.
Kuhar et al., *Trends Neurosci.,* 14(7):299-302, 1991.
Kuhl et al., *Cell,* 50:1057, 1987.
Kunz et al., *Nuc. Acids Res.,* 17:1121, 1989.
Kyte and Doolittle, *J. Mol. Biol.,* 157(1):105-132, 1982.
Larsen et al., *Proc. Natl. Acad. Sci. USA,* 83:8283, 1986.
Laspia et al., *Cell,* 59:283, 1989.
Latimer et al., *Mol. Cell. Biol.,* 10:760, 1990.
Le Bars, *Neuronal Serotonin,* Osborne and Hamin (Eds), 171-229, 1988.
Le Gal La Salle et al., *Science,* 259:988-990, 1993.
Lee et al., *Nature,* 294:228, 1981.
Lee et al., *Nucleic Acids Res.,* 12:4191-206, 1984.
Levenson et al., *Hum. Gene Ther.,* 9(8):1233-6, 1998.
Levinson et al., *Nature,* 295:79, 1982.
Levrero et al., *Gene,* 101: 195-202, 1991.
Lin et al., *Mol. Cell. Biol.,* 10:850, 1990.
Luria et al., *EMBO J.,* 6:3307, 1987.
Lusky and Botchan, *Proc. Natl. Acad. Sci. USA,* 83:3609, 1986.
Lusky et al., *Mol. Cell. Biol.* 3:1108, 1983.
Macejak and Sarnow, *Nature,* 353:90-94, 1991.
Majors and Varmus, *Proc. Natl. Acad. Sci. USA,* 80:5866, 1983.
Maniatis, et al., Molecular Cloning, A Laboratory Manual, Cold Spring Harbor Press, Cold Spring Harbor, N.Y., 1990.
Mann et al., *Cell,* 33:153-159, 1983.
Markowitz et al., *J. Virol.,* 62:1120-1124, 1988.
Masson et al., *Pharmacol. Rev.,* 51:439-464, 1999.
McNeall et al., *Gene,* 76:81, 1989.
Meltzer, et al., *Arch. Gen. Psychiat.,* 38:1322-1326, 1981.
Miksicek et al., *Cell,* 46:203, 1986.
Mordacq and Linzer, *Genes and Dev.,* 3:760, 1989.
Moreau et al., *Nucl. Acids Res.,* 9:6047, 1981.
Morozova et al., *Tsitologiia,* 23(8):916-923, 1981.
Muesing et al., *Cell,* 48:691, 1987.
Mulligan, *Science,* 260:926-932, 1993.
Naranjo et al., *Clin. Pharmacol. Ther.,* 41:266-274, 1987.
Neumeister et al., *Arch. Gen. Psychiatry,* 59(7):613-620, 2002.
Ng et al., *Nuc. Acids Res.,* 17:601, 1989.
Nicolas and Rubenstein, In: *Vectors: A survey of molecular cloning vectors and their uses,* Rodriguez and Denhardt (Eds.), Stoneham: Butterworth, 493-513, 1988.
Nicolau et al., *Methods Enzymol.,* 149:157-176, 1987.
Ondeket al.,*EMBO J.,* 6:1017,1987.
Ornitz et al., *Mol. Cell. Biol.,* 7:3466, 1987.
Pacholczyk et al., *Nature,* March 28;350(6316):350-4, 1991.
Palmiter et al., *Nature,* 300:611, 1982.
Paskind et al., *Virology,* 67:242-248, 1975.
Paul et al., *Arch. Gen. Psych.,* 38:1315-1317, 1981.
Pech et al., *Mol. Cell. Biol.,* 9:396, 1989.
Pelham, *Nature,* 389(6646):17, 19, 1997.
Pelletier and Sonenberg, *Nature,* 334:320-325, 1988.
Perales et al., *Proc. Natl. Acad. Sci. USA,* 91:4086-4090, 1994.
Perez-Stable and Constantini, *Mol. Cell. Biol.,* 10: 1116, 1990.
Perry et al., *Brit. J. Psych.,* 142:188-192, 1983.
Picard and Schaffner, *Nature,* 307:83, 1984.
Pietruck and Ullrich, *Kidney Int.,* 47(6):1647-1657, 1995.
Pinkert et al., *Genes and Dev.,* 1:268, 1987.
Ponta et al., *Proc. Natl. Acad. Sci. USA,* 82:1020, 1985.
Porton et al., *Mol. Cell. Biol.,* 10:1076, 1990.
Porzgen et al., *Biochem Biophys Res Commun.,* 227(2):642-643, 1996.
Potter et al.,*Proc. Natl. Acad. Sci. USA,* 81:7161-7165, 1984.
Prasad and Amara, *J. Neurosci.,* 21:7561-7567, 2001.
Queen and Baltimore, *Cell,* 35:741, 1983.
Quinn et al., *Mol. Cell. Biol.,* 9:4713, 1989.
Racher et al., *Biotechnology Techniques,* 9:169-174, 1995.
Ragot et al., *Nature,* 361:647-650, 1993.
Ramamoorthy et al., *Am. J. Obstet. Gynecol.,* 173:1782-1787, 1995.
Ramamoorthy et al., *Biochemistry,* 32:1346-1353, 1993.
Ramamoorthy et al., *J. Biol. Chem.,* 273:2458-2466, 1998.
Ramamoorthy et al., *Proc. Natl. Acad. Sci., USA,* 90(6):2542-2546, 1993.
Redondo et al., *Science,* 247:1225, 1990.
Reisman and Rotter, *Mol. Cell. Biol.,* 9:3571, 1989.
Remington's Pharmaceutical Sciences, $15^{th}$ ed., pages 1035-1038 and 1570-1580, Mack Publishing Company, Easton, Pa., 1980.
Renan, *Radiother. Oncol.,* 19:197-218, 1990.
Resendez Jr. et al., *Mol. Cell. Biol.,* 8:4579, 1988.

Ressler and Nemeroff, *Biol. Psychiatry,* 46:1219-1233, 1999.
Rich et al., *Hum. Gene Ther.,* 4:461-476, 1993.
Ridgeway, In: *Vectors: A survey of molecular cloning vectors and their uses,* Stoneham: Butterworth, 467-492, 1988.
Ripe et al., *Mol. Cell. Biol.,* 9:2224, 1989.
Rittling et al., *Nuc. Acids Res.,* 17:1619, 1989.
Robertson et al., *Nature* 322:445-448, 1986
Rohlicek and Ullrich, *Ren. Physiol. Biochem.,* 17(2):57-61, 1994.
Rosen et al., *Cell,* 41:813, 1988.
Rosenfeld et al., *Cell,* 68:143-155, 1992.
Rosenfeld et al., *Science,* 252:431-434, 1991.
Roux et al., *Proc. Natl. Acad. Sci. USA,* 86:9079-9083, 1989.
Rudnick and Clark, *Biochim. Biophys. Acta,* 1144(3):249-63, 1993.
Sakai et al., *Genes and Dev.,* 2:1144, 1988.
Sambrook et al., In: *Molecular Cloning: A Laboratory Manual,* 2nd Ed., Cold Spring Harbor Press, Cold Spring Harbor, N.Y., 2001.
Samochowiec et al., *Neuropsychobiology,* 43(4):248-253, 2001.
Samulski et al., *J. Virol.,* 61(10):3096-3101, 1987.
Satake et al., *J. Virol.,* 62:970, 1988.
Schaffher et al., *J. Mol. Biol.,* 201:81, 1988.
Schloss, *Psychopharmacol.,* 12(2):115-21, 1998.
Schroeter et al., *J. Comp. Neurol.,* 420:211-232, 2000.
Searle et al., *Mol. Cell. Biol.,* 5:1480, 1985.
Sharp and Marciniak, *Cell,* 59:229, 1989.
Shaul and Ben-Levy, *EMBO J.,* 6:1913, 1987.
Sherman et al., *Mol. Cell. Biol.,* 9:50, 1989.
Silverstone et al., *Appetite,* 7(Suppl)85-97, 1986.
Skrebitsky and Chepkova, *Rev. Neurosci.,* 9:243-264, 1998.
Sleigh and Lockett, *J. EMBO,* 4:3831, 1985.
Smith and Levi, *J. Pharmacol. Exp. Ther.,* 291:456-463, 1999.
Sora et al., *Proc Natl Acad Sci USA., April* 24;98(9):5300-5, 2001.
Soubrie, In: *Neuronal Serotonin,* Osborne and Hamon (eds.), 255-270 1988.
Southwick et al., *Biol. Psychiatry,* 46:1192-1204, 1999.
Spalholz et al., *Cell,* 42:183, 1985.
Spandau and Lee, *J. Virology,* 62:427, 1988.
Spandidos and Wilkie, *EMBO J.,* 2:1193, 1983.
Stachon et al., *Cellular Physiol. Biochem.,* 6:72-91, 1996.
Stanley et al., *Science,* 216:1337-1339, 1982.
Stephens and Hentschel, *Biochem. J.,* 248:1, 1987.
Stewart et al., *EMBO J.,* 6:383-388, 1987.
Stober et al., *Lancet.,* 347(9011):1340-1341, 1996.
Stratford-Perricaudet and Perricaudet, In: *Human Gene Transfer,* Cohen-Haguenauer and Boiron (Eds.), John Libbey Eurotext, France, 51-61, 1991.
Stratford-Perricaudet et al., *Hum. Gene. Ther.,* 1:241-256, 1990.
Stuart et al., *Nature,* 317:828, 1985.
Sullivan and Peterlin, *Mol. Cell. Biol.,* 7:3315, 1987.
Suranyi-Cadotte et al., *Life Sci.,* 36(8):795-799, 1985.
Suranyi-Cadotte et al., *Life Sci.,* 37(24):2305-23119, 1985.
Swartzendruber and Lehman, *J. Cell. Physiology,* 85:179, 1975.
Takebe et al., *Mol. Cell. Biol.,* 8:466, 1988.
Tavernier et al., *Nature,* 301:634, 1983.
Taylor and Kingston, *Mol. Cell. Biol.,* 10:165, 1990a.
Taylor and Kingston, *Mol. Cell. Biol.,* 10:176, 1990b.
Taylor et al., *J. Biol. Chem.,* 264:15160, 1989.
Temin, *In: Gene Transfer,* Kucherlapati (ed.), NY, Plenum Press, 149-188, 1986.
Thiesen et al., *J. Virol.,* 62:614, 1988.
Top et al., *J. Infect. Dis.,* 124:155-160, 1971.
Treisman, *Cell,* 42:889, 1985.
Tronche et al., *Mol. Biol. Med.,* 7:173, 1990.
Trudel and Constantini, *Genes and Dev.,* 6:954, 1987.
Tsai et al., *Neuropsychobiology,* 45(3):131-133, 2002.
Tur-Kaspa et al., *Mol. Cell Biol.,* 6:716-718, 1986.
Tyndell et al., *Nuc. Acids. Res.,* 9:6231, 1981.
Van Woert, M. H. et al., *Monogr. Neural. Sci.,* 3:71-80, 1976.
Vannice and Levinson, *J. Virology,* 62:1305, 1988.
Varmus et al., *Cell,* 25:23-36, 1981.
Vasseur et al., *Proc. Natl. Acad. Sci. USA,* 77:1068, 1980.
Wada et al., *Nucleic Acids Res.,* 18(Suppl):2367-411, 1990.
Wagner et al., *Proc. Natl. Acad. Sci. USA* 87(9):3410-3414, 1990.
Wang and Calame, *Cell,* 47:241, 1986.
Watanabe et al., *Jpn. Heart J.,* 22:977-985, 1981.
Weber et al., *Cell,* 36:983, 1984.
Weinberger et al., *Mol. Cell. Biol.,* 8:988, 1984.
Winoto and Baltimore, *Cell,* 59:649, 1989.
WO 84/03564
Wong et al., *Gene,* 10:87-94, 1980.
Wu and Wu, *Adv. Drug Delivery Rev.,* 12:159-167, 1993.
Wu and Wu, *Biochemistry,* 27:887-892,1988.
Wu and Wu, *J. Biol. Chem.,* 262:4429-4432,1987.
Wu et al., *Biochim. Biophys. Acta.,* 1466:315-327, 2000.
Yutzey et al., *Mol. Cell. Biol.,* 9:1397, 1989.

What is claimed is:

1. An isolated nucleic acid encoding a serotonin transporter comprising the amino acid sequence of SEQ ID NO: 4.

2. The isolated nucleic acid of claim 1, further defined as having the nucleic acid sequence of SEQ ID NO: 3.

3. A vector comprising the isolated nucleic acid encoding a serotonin transporter comprising the amino acid sequence of SEQ ID NO: 4.

4. The vector of claim 3, comprising the nucleic acid sequence of SEQ ID NO: 3.

5. The vector of claim 3, wherein the nucleic acid is operatively linked to a promoter that directs the expression of the nucleic acid in a cell.

6. The vector of claim 5, wherein the promoter is a serotonin transporter promoter.

7. The vector of claim 3, comprising a viral vector.

8. The vector of claim 7, wherein the viral vector is an adenoviral vector, an adeno-associated viral vector, a retroviral vector, a lentiviral vector, a herpes viral vector, polyoma viral vector or hepatitis B viral vector.

9. An isolated host cell containing a recombinant nucleic acid encoding a serotonin transporter comprising the amino acid sequence of SEQ ID NO: 4.

10. The host cell of claim 9, wherein the cell is a mammalian cell.

11. The host cell of claim 10, wherein the mammalian cell is a human, mouse, rat, monkey, chicken, dog, cat, horse, pig, cow, sheep, goat, or hamster cell.

12. The host cell of claim 10, wherein the cell is a neuronal cell.

13. The host cell of claim 9, wherein the cell is an insect cell.

14. The host cell of claim 9, further comprising a vector.

15. A method of screening for a candidate substance that blocks serotonin transporter (SERT) activity of a SERT having the amino acid sequence of SEQ ID NO:4 comprising:

a) providing a cell or cell extract comprising a SERT having the amino acid sequence of SEQ ID NO: 4;

b) exposing the cell or cell extract to a candidate substance;

c) measuring binding of the candidate substance to the SERT in step (a);

d) providing a cell or cell extract comprising a SERT having the amino acid sequence of SEQ ID NO: 2 and a cell or cell extract comprising a SERT having the amino acid sequence of SEQ ID NO: 6;

e) measuring the binding of the candidate substance to the SERTs of step (d); and f) comparing binding of the candidate substance by the SERT of step (a) to binding of the candidate substance by a SERT having the amino acid sequence of SEQ ID NO: 2 or SEQ ID NO: 6, wherein the ability of the candidate substance to bind to the SERT having the amino acid sequence of SEQ ID NO: 4, but not the SERT having the amino acid sequence of SEQ ID NO: 2 or SEQ ID NO: 6, indicates that the candidate substance blocks SERT activity of a SERT having the amino acid sequence of SEQ ID NO:4.

16. The method of claim 15, further comprising measuring transport of the candidate substance by the SERT in the cell in step (a) and the SERTs of step (d).

17. The method of claim 16, further comprising comparing transport of the candidate substance by the SERT in the cell of step (a) to transport of the candidate substance by a SERT having the amino acid sequence of SEQ ID NO: 2 or SEQ ID NO: 6, wherein transport of the candidate substance by the serotonin transporter having the amino acid sequence of SEQ ID NO: 4, but not the serotonin transporter having the amino acid sequence of SEQ ID NO: 2 or SEQ ID NO: 6, indicates that the candidate substance blocks serotonin transporter activity

18. The method of claim 15, wherein the cell or cell extract is obtained from a mammal.

19. The method of claim 15, wherein the cell or cell extract is neuronal in origin.

20. The method of claim 15, wherein the candidate substance comprises a radiolabel.

21. The method of claim 15, further comprising the use of a fluorescent plate reader in step c) to provide high-throughput screening of candidate substances.

22. The method of claim 15, wherein the candidate substance is an antidepressant.

23. The method of claim 15, wherein the candidate substance is an organic small molecule.

24. The method of claim 15, wherein the candidate substance is an inorganic small molecule.

25. The method of claim 15, wherein the candidate substance is pharmaceutical drug.

* * * * *

SEQUENCE LISTING

```
<160> NUMBER OF SEQ ID NOS: 20

<210> SEQ ID NO 1
<211> LENGTH: 1893
<212> TYPE: DNA
<213> ORGANISM: Homo sapiens
<220> FEATURE:
<221> NAME/KEY: CDS
<222> LOCATION: (1)..(1890)

<400> SEQUENCE: 1

atg gag acg acg ccc ttg aat tct cag aag cag cta tca gcg tgt gaa       48
Met Glu Thr Thr Pro Leu Asn Ser Gln Lys Gln Leu Ser Ala Cys Glu
  1               5                  10                  15
```

-continued

```
gat gga gaa gat tgt cag gaa aac gga gtt cta cag aag gtt gtt ccc        96
Asp Gly Glu Asp Cys Gln Glu Asn Gly Val Leu Gln Lys Val Val Pro
             20                  25                  30

acc cca ggg gac aaa gtg gag tcc ggg caa ata tcc aat ggg tac tca       144
Thr Pro Gly Asp Lys Val Glu Ser Gly Gln Ile Ser Asn Gly Tyr Ser
         35                  40                  45

gca gtt cca agt cct ggt gcg gga gat gac aca cgg cac tct atc cca       192
Ala Val Pro Ser Pro Gly Ala Gly Asp Asp Thr Arg His Ser Ile Pro
     50                  55                  60

gcg acc acc acc acc cta gtg gct gag ctt cat caa ggg gaa cgg gag       240
Ala Thr Thr Thr Thr Leu Val Ala Glu Leu His Gln Gly Glu Arg Glu
 65                  70                  75                  80

acc tgg ggc aag aag gtg gat ttc ctt ctc tca gtg att ggc tat gct       288
Thr Trp Gly Lys Lys Val Asp Phe Leu Leu Ser Val Ile Gly Tyr Ala
                 85                  90                  95

gtg gac ctg ggc aat gtc tgg cgc ttc ccc tac ata tgt tac cag aat       336
Val Asp Leu Gly Asn Val Trp Arg Phe Pro Tyr Ile Cys Tyr Gln Asn
            100                 105                 110

gga ggg ggg gca ttc ctc ctc ccc tac acc atc atg gcc att ttt ggg       384
Gly Gly Gly Ala Phe Leu Leu Pro Tyr Thr Ile Met Ala Ile Phe Gly
        115                 120                 125

gga atc ccg ctc ttt tac atg gag ctc gca ctg gga cag tac cac cga       432
Gly Ile Pro Leu Phe Tyr Met Glu Leu Ala Leu Gly Gln Tyr His Arg
    130                 135                 140

aat gga tgc att tca ata tgg agg aaa atc tgc ccg att ttc aaa ggg       480
Asn Gly Cys Ile Ser Ile Trp Arg Lys Ile Cys Pro Ile Phe Lys Gly
145                 150                 155                 160

att ggt tat gcc atc tgc atc att gcc ttt tac att gct tcc tac tac       528
Ile Gly Tyr Ala Ile Cys Ile Ile Ala Phe Tyr Ile Ala Ser Tyr Tyr
                165                 170                 175

aac acc atc atg gcc tgg gcg cta tac tac ctc atc tcc tcc ttc acg       576
Asn Thr Ile Met Ala Trp Ala Leu Tyr Tyr Leu Ile Ser Ser Phe Thr
            180                 185                 190

gac cag ctg ccc tgg acc agc tgc aag aac tcc tgg aac act ggc aac       624
Asp Gln Leu Pro Trp Thr Ser Cys Lys Asn Ser Trp Asn Thr Gly Asn
        195                 200                 205

tgc acc aat tac ttc tcc gag gac aac atc acc tgg acc ctc cat tcc       672
Cys Thr Asn Tyr Phe Ser Glu Asp Asn Ile Thr Trp Thr Leu His Ser
    210                 215                 220

acg tcc cct gct gaa gaa ttt tac acg cgc cac gtc ctg cag atc cac       720
Thr Ser Pro Ala Glu Glu Phe Tyr Thr Arg His Val Leu Gln Ile His
225                 230                 235                 240

cgg tct aag ggg ctc cag gac ctg ggg ggc atc agc tgg cag ctg gcc       768
Arg Ser Lys Gly Leu Gln Asp Leu Gly Gly Ile Ser Trp Gln Leu Ala
                245                 250                 255

ctc tgc atc atg ctg atc ttc act gtt atc tac ttc agc atc tgg aaa       816
Leu Cys Ile Met Leu Ile Phe Thr Val Ile Tyr Phe Ser Ile Trp Lys
            260                 265                 270

ggc gtc aag acc tct ggc aag gtg gtg tgg gtg aca gcc acc ttc cct       864
Gly Val Lys Thr Ser Gly Lys Val Val Trp Val Thr Ala Thr Phe Pro
        275                 280                 285

tat atc atc ctt tct gtc ctg ctg gtg agg ggt gcc acc ctc cct gga       912
Tyr Ile Ile Leu Ser Val Leu Leu Val Arg Gly Ala Thr Leu Pro Gly
    290                 295                 300

gcc tgg agg ggt gtt ctc ttc tac ttg aaa ccc aat tgg cag aaa ctc       960
Ala Trp Arg Gly Val Leu Phe Tyr Leu Lys Pro Asn Trp Gln Lys Leu
305                 310                 315                 320

ctg gag aca ggg gtg tgg ata gat gca gcc gct cag atc ttc ttc tct      1008
Leu Glu Thr Gly Val Trp Ile Asp Ala Ala Ala Gln Ile Phe Phe Ser
                325                 330                 335
```

-continued

```
ctt ggt ccg ggc ttt ggg gtc ctg ctg gct ttt gct agc tac aac aag      1056
Leu Gly Pro Gly Phe Gly Val Leu Leu Ala Phe Ala Ser Tyr Asn Lys
            340                 345                 350

ttc aac aac aac tgc tac caa gat gcc ctg gtg acc agc gtg gtg aac      1104
Phe Asn Asn Asn Cys Tyr Gln Asp Ala Leu Val Thr Ser Val Val Asn
        355                 360                 365

tgc atg acg agc ttc gtt tcg gga ttt gtc atc ttc aca gtg ctc ggt      1152
Cys Met Thr Ser Phe Val Ser Gly Phe Val Ile Phe Thr Val Leu Gly
    370                 375                 380

tac atg gct gag atg agg aat gaa gat gtg tct gag gtg gcc aaa gac      1200
Tyr Met Ala Glu Met Arg Asn Glu Asp Val Ser Glu Val Ala Lys Asp
385                 390                 395                 400

gca ggt ccc agc ctc ctc ttc atc acg tat gca gaa gcg ata gcc aac      1248
Ala Gly Pro Ser Leu Leu Phe Ile Thr Tyr Ala Glu Ala Ile Ala Asn
                405                 410                 415

atg cca gcg tcc act ttc ttt gcc atc atc ttc ttt ctg atg tta atc      1296
Met Pro Ala Ser Thr Phe Phe Ala Ile Ile Phe Phe Leu Met Leu Ile
            420                 425                 430

acg ctg ggc ttg gac agc acg ttt gca ggc ttg gag ggg gtg atc acg      1344
Thr Leu Gly Leu Asp Ser Thr Phe Ala Gly Leu Glu Gly Val Ile Thr
        435                 440                 445

gct gtg ctg gat gag ttc cca cac gtc tgg gcc aag cgc cgg gag cgg      1392
Ala Val Leu Asp Glu Phe Pro His Val Trp Ala Lys Arg Arg Glu Arg
    450                 455                 460

ttc gtg ctc gcc gtg gtc atc acc tgc ttc ttt gga tcc ctg gtc acc      1440
Phe Val Leu Ala Val Val Ile Thr Cys Phe Phe Gly Ser Leu Val Thr
465                 470                 475                 480

ctg act ttt gga ggg gcc tac gtg gtg aag ctg ctg gag gag tat gcc      1488
Leu Thr Phe Gly Gly Ala Tyr Val Val Lys Leu Leu Glu Glu Tyr Ala
                485                 490                 495

acg ggg ccc gca gtg ctc act gtc gcg ctg atc gaa gca gtc gct gtg      1536
Thr Gly Pro Ala Val Leu Thr Val Ala Leu Ile Glu Ala Val Ala Val
            500                 505                 510

tct tgg ttc tat ggc atc act cag ttc tgc agg gac gtg aag gaa atg      1584
Ser Trp Phe Tyr Gly Ile Thr Gln Phe Cys Arg Asp Val Lys Glu Met
        515                 520                 525

ctc ggc ttc agc ccg ggg tgg ttc tgg agg atc tgc tgg gtg gcc atc      1632
Leu Gly Phe Ser Pro Gly Trp Phe Trp Arg Ile Cys Trp Val Ala Ile
    530                 535                 540

agc cct ctg ttt ctc ctg ttc atc att tgc agt ttt ctg atg agc ccg      1680
Ser Pro Leu Phe Leu Leu Phe Ile Ile Cys Ser Phe Leu Met Ser Pro
545                 550                 555                 560

cca caa cta cga ctt ttc caa tat aat tat cct tac tgg agt atc atc      1728
Pro Gln Leu Arg Leu Phe Gln Tyr Asn Tyr Pro Tyr Trp Ser Ile Ile
                565                 570                 575

ttg ggt tac tgc ata gga acc tca tct ttc att tgc atc ccc aca tat      1776
Leu Gly Tyr Cys Ile Gly Thr Ser Ser Phe Ile Cys Ile Pro Thr Tyr
            580                 585                 590

ata gct tat cgg ttg atc atc act cca ggg aca ttt aaa gag cgt att      1824
Ile Ala Tyr Arg Leu Ile Ile Thr Pro Gly Thr Phe Lys Glu Arg Ile
        595                 600                 605

att aaa agt att acc cca gaa aca cca aca gaa att cct tgt ggg gac      1872
Ile Lys Ser Ile Thr Pro Glu Thr Pro Thr Glu Ile Pro Cys Gly Asp
    610                 615                 620

atc cgc ttg aat gct gtg taa                                          1893
Ile Arg Leu Asn Ala Val
625                 630
```

<210> SEQ ID NO 2

```
<211> LENGTH: 630
<212> TYPE: PRT
<213> ORGANISM: Homo sapiens

<400> SEQUENCE: 2

Met Glu Thr Thr Pro Leu Asn Ser Gln Lys Gln Leu Ser Ala Cys Glu
 1               5                  10                  15

Asp Gly Glu Asp Cys Gln Glu Asn Gly Val Leu Gln Lys Val Val Pro
            20                  25                  30

Thr Pro Gly Asp Lys Val Glu Ser Gly Gln Ile Ser Asn Gly Tyr Ser
        35                  40                  45

Ala Val Pro Ser Pro Gly Ala Gly Asp Asp Thr Arg His Ser Ile Pro
 50                  55                  60

Ala Thr Thr Thr Thr Leu Val Ala Glu Leu His Gln Gly Glu Arg Glu
 65                  70                  75                  80

Thr Trp Gly Lys Lys Val Asp Phe Leu Leu Ser Val Ile Gly Tyr Ala
                85                  90                  95

Val Asp Leu Gly Asn Val Trp Arg Phe Pro Tyr Ile Cys Tyr Gln Asn
            100                 105                 110

Gly Gly Gly Ala Phe Leu Leu Pro Tyr Thr Ile Met Ala Ile Phe Gly
        115                 120                 125

Gly Ile Pro Leu Phe Tyr Met Glu Leu Ala Leu Gly Gln Tyr His Arg
130                 135                 140

Asn Gly Cys Ile Ser Ile Trp Arg Lys Ile Cys Pro Ile Phe Lys Gly
145                 150                 155                 160

Ile Gly Tyr Ala Ile Cys Ile Ile Ala Phe Tyr Ile Ala Ser Tyr Tyr
                165                 170                 175

Asn Thr Ile Met Ala Trp Ala Leu Tyr Tyr Leu Ile Ser Ser Phe Thr
            180                 185                 190

Asp Gln Leu Pro Trp Thr Ser Cys Lys Asn Ser Trp Asn Thr Gly Asn
        195                 200                 205

Cys Thr Asn Tyr Phe Ser Glu Asp Asn Ile Thr Trp Thr Leu His Ser
210                 215                 220

Thr Ser Pro Ala Glu Glu Phe Tyr Thr Arg His Val Leu Gln Ile His
225                 230                 235                 240

Arg Ser Lys Gly Leu Gln Asp Leu Gly Gly Ile Ser Trp Gln Leu Ala
                245                 250                 255

Leu Cys Ile Met Leu Ile Phe Thr Val Ile Tyr Phe Ser Ile Trp Lys
            260                 265                 270

Gly Val Lys Thr Ser Gly Lys Val Val Trp Val Thr Ala Thr Phe Pro
        275                 280                 285

Tyr Ile Ile Leu Ser Val Leu Leu Val Arg Gly Ala Thr Leu Pro Gly
290                 295                 300

Ala Trp Arg Gly Val Leu Phe Tyr Leu Lys Pro Asn Trp Gln Lys Leu
305                 310                 315                 320

Leu Glu Thr Gly Val Trp Ile Asp Ala Ala Ala Gln Ile Phe Phe Ser
                325                 330                 335

Leu Gly Pro Gly Phe Gly Val Leu Leu Ala Phe Ala Ser Tyr Asn Lys
            340                 345                 350

Phe Asn Asn Asn Cys Tyr Gln Asp Ala Leu Val Thr Ser Val Val Asn
        355                 360                 365

Cys Met Thr Ser Phe Val Ser Gly Phe Val Ile Phe Thr Val Leu Gly
370                 375                 380

Tyr Met Ala Glu Met Arg Asn Glu Asp Val Ser Glu Val Ala Lys Asp
```

-continued

```
385                 390                 395                 400

Ala Gly Pro Ser Leu Leu Phe Ile Thr Tyr Ala Glu Ala Ile Ala Asn
                405                 410                 415

Met Pro Ala Ser Thr Phe Phe Ala Ile Ile Phe Phe Leu Met Leu Ile
            420                 425                 430

Thr Leu Gly Leu Asp Ser Thr Phe Ala Gly Leu Glu Gly Val Ile Thr
        435                 440                 445

Ala Val Leu Asp Glu Phe Pro His Val Trp Ala Lys Arg Arg Glu Arg
    450                 455                 460

Phe Val Leu Ala Val Val Ile Thr Cys Phe Phe Gly Ser Leu Val Thr
465                 470                 475                 480

Leu Thr Phe Gly Gly Ala Tyr Val Val Lys Leu Leu Glu Glu Tyr Ala
                485                 490                 495

Thr Gly Pro Ala Val Leu Thr Val Ala Leu Ile Glu Ala Val Ala Val
            500                 505                 510

Ser Trp Phe Tyr Gly Ile Thr Gln Phe Cys Arg Asp Val Lys Glu Met
        515                 520                 525

Leu Gly Phe Ser Pro Gly Trp Phe Trp Arg Ile Cys Trp Val Ala Ile
    530                 535                 540

Ser Pro Leu Phe Leu Leu Phe Ile Ile Cys Ser Phe Leu Met Ser Pro
545                 550                 555                 560

Pro Gln Leu Arg Leu Phe Gln Tyr Asn Tyr Pro Tyr Trp Ser Ile Ile
                565                 570                 575

Leu Gly Tyr Cys Ile Gly Thr Ser Ser Phe Ile Cys Ile Pro Thr Tyr
            580                 585                 590

Ile Ala Tyr Arg Leu Ile Ile Thr Pro Gly Thr Phe Lys Glu Arg Ile
        595                 600                 605

Ile Lys Ser Ile Thr Pro Glu Thr Pro Thr Glu Ile Pro Cys Gly Asp
    610                 615                 620

Ile Arg Leu Asn Ala Val
625                 630


<210> SEQ ID NO 3
<211> LENGTH: 1893
<212> TYPE: DNA
<213> ORGANISM: Artificial Sequence
<220> FEATURE:
<223> OTHER INFORMATION: Description of Artificial Sequence:  Synthetic
      Primer
<220> FEATURE:
<221> NAME/KEY: CDS
<222> LOCATION: (1)..(1893)

<400> SEQUENCE: 3

atg gag acg acg ccc ttg aat tct cag aag cag cta tca gcg tgt gaa       48
Met Glu Thr Thr Pro Leu Asn Ser Gln Lys Gln Leu Ser Ala Cys Glu
  1               5                  10                  15

gat gga gaa gat tgt cag gaa aac gga gtt cta cag aag gtt gtt ccc       96
Asp Gly Glu Asp Cys Gln Glu Asn Gly Val Leu Gln Lys Val Val Pro
             20                  25                  30

acc cca ggg gac aaa gtg gag tcc ggg caa ata tcc aat ggg tac tca      144
Thr Pro Gly Asp Lys Val Glu Ser Gly Gln Ile Ser Asn Gly Tyr Ser
         35                  40                  45

gca gtt cca agt cct ggt gcg gga gat gac aca cgg cac tct atc cca      192
Ala Val Pro Ser Pro Gly Ala Gly Asp Asp Thr Arg His Ser Ile Pro
     50                  55                  60

gcg acc acc acc acc cta gtg gct gag ctt cat caa ggg gaa cgg gag      240
Ala Thr Thr Thr Thr Leu Val Ala Glu Leu His Gln Gly Glu Arg Glu
```

-continued

```
 65                  70                  75                  80

acc tgg ggc aag aag gtg gat ttc ctt ctc tca gtg att ggc tat gct      288
Thr Trp Gly Lys Lys Val Asp Phe Leu Leu Ser Val Ile Gly Tyr Ala
                 85                  90                  95

gtg gac ctg ggc aat gtc tgg cgc ttc ccc tac ata tgt tac cag aat      336
Val Asp Leu Gly Asn Val Trp Arg Phe Pro Tyr Ile Cys Tyr Gln Asn
            100                 105                 110

gga ggg ggg gca ttc ctc ctc ccc tac acc atc atg gcc att ttt ggg      384
Gly Gly Gly Ala Phe Leu Leu Pro Tyr Thr Ile Met Ala Ile Phe Gly
        115                 120                 125

gga atc ccg ctc ttt tac atg gag ctc gca ctg gga cag tac cac cga      432
Gly Ile Pro Leu Phe Tyr Met Glu Leu Ala Leu Gly Gln Tyr His Arg
    130                 135                 140

aat gga tgc att tca ata tgg agg aaa atc tgc ccg att ttc aaa ggg      480
Asn Gly Cys Ile Ser Ile Trp Arg Lys Ile Cys Pro Ile Phe Lys Gly
145                 150                 155                 160

att ggt tat gcc atc tgc atc att gcc ttt tac atg gct tcc tac tac      528
Ile Gly Tyr Ala Ile Cys Ile Ile Ala Phe Tyr Met Ala Ser Tyr Tyr
                165                 170                 175

aac acc atc atg gcc tgg gcg cta tac tac ctc atc tcc tcc ttc acg      576
Asn Thr Ile Met Ala Trp Ala Leu Tyr Tyr Leu Ile Ser Ser Phe Thr
            180                 185                 190

gac cag ctg ccc tgg acc agc tgc aag aac tcc tgg aac act ggc aac      624
Asp Gln Leu Pro Trp Thr Ser Cys Lys Asn Ser Trp Asn Thr Gly Asn
        195                 200                 205

tgc acc aat tac ttc tcc gag gac aac atc acc tgg acc ctc cat tcc      672
Cys Thr Asn Tyr Phe Ser Glu Asp Asn Ile Thr Trp Thr Leu His Ser
    210                 215                 220

acg tcc cct gct gaa gaa ttt tac acg cgc cac gtc ctg cag atc cac      720
Thr Ser Pro Ala Glu Glu Phe Tyr Thr Arg His Val Leu Gln Ile His
225                 230                 235                 240

cgg tct aag ggg ctc cag gac ctg ggg ggc atc agc tgg cag ctg gcc      768
Arg Ser Lys Gly Leu Gln Asp Leu Gly Gly Ile Ser Trp Gln Leu Ala
                245                 250                 255

ctc tgc atc atg ctg atc ttc act gtt atc tac ttc agc atc tgg aaa      816
Leu Cys Ile Met Leu Ile Phe Thr Val Ile Tyr Phe Ser Ile Trp Lys
            260                 265                 270

ggc gtc aag acc tct ggc aag gtg gtg tgg gtg aca gcc acc ttc cct      864
Gly Val Lys Thr Ser Gly Lys Val Val Trp Val Thr Ala Thr Phe Pro
        275                 280                 285

tat atc atc ctt tct gtc ctg ctg gtg agg ggt gcc acc ctc cct gga      912
Tyr Ile Ile Leu Ser Val Leu Leu Val Arg Gly Ala Thr Leu Pro Gly
    290                 295                 300

gcc tgg agg ggt gtt ctc ttc tac ttg aaa ccc aat tgg cag aaa ctc      960
Ala Trp Arg Gly Val Leu Phe Tyr Leu Lys Pro Asn Trp Gln Lys Leu
305                 310                 315                 320

ctg gag aca ggg gtg tgg ata gat gca gcc gct cag atc ttc ttc tct     1008
Leu Glu Thr Gly Val Trp Ile Asp Ala Ala Ala Gln Ile Phe Phe Ser
                325                 330                 335

ctt ggt ccg ggc ttt ggg gtc ctg ctg gct ttt gct agc tac aac aag     1056
Leu Gly Pro Gly Phe Gly Val Leu Leu Ala Phe Ala Ser Tyr Asn Lys
            340                 345                 350

ttc aac aac aac tgc tac caa gat gcc ctg gtg acc agc gtg gtg aac     1104
Phe Asn Asn Asn Cys Tyr Gln Asp Ala Leu Val Thr Ser Val Val Asn
        355                 360                 365

tgc atg acg agc ttc gtt tcg gga ttt gtc atc ttc aca gtg ctc ggt     1152
Cys Met Thr Ser Phe Val Ser Gly Phe Val Ile Phe Thr Val Leu Gly
    370                 375                 380

tac atg gct gag atg agg aat gaa gat gtg tct gag gtg gcc aaa gac     1200
```

-continued

```
Tyr Met Ala Glu Met Arg Asn Glu Asp Val Ser Glu Val Ala Lys Asp
385                 390                 395                 400

gca ggt ccc agc ctc ctc ttc atc acg tat gca gaa gcg ata gcc aac     1248
Ala Gly Pro Ser Leu Leu Phe Ile Thr Tyr Ala Glu Ala Ile Ala Asn
                405                 410                 415

atg cca gcg tcc act ttc ttt gcc atc atc ttc ttt ctg atg tta atc     1296
Met Pro Ala Ser Thr Phe Phe Ala Ile Ile Phe Phe Leu Met Leu Ile
            420                 425                 430

acg ctg ggc ttg gac agc acg ttt gca ggc ttg gag ggg gtg atc acg     1344
Thr Leu Gly Leu Asp Ser Thr Phe Ala Gly Leu Glu Gly Val Ile Thr
        435                 440                 445

gct gtg ctg gat gag ttc cca cac gtc tgg gcc aag cgc cgg gag cgg     1392
Ala Val Leu Asp Glu Phe Pro His Val Trp Ala Lys Arg Arg Glu Arg
    450                 455                 460

ttc gtg ctc gcc gtg gtc atc acc tgc ttc ttt gga tcc ctg gtc acc     1440
Phe Val Leu Ala Val Val Ile Thr Cys Phe Phe Gly Ser Leu Val Thr
465                 470                 475                 480

ctg act ttt gga ggg gcc tac gtg gtg aag ctg ctg gag gag tat gcc     1488
Leu Thr Phe Gly Gly Ala Tyr Val Val Lys Leu Leu Glu Glu Tyr Ala
                485                 490                 495

acg ggg ccc gca gtg ctc act gtc gcg ctg atc gaa gca gtc gct gtg     1536
Thr Gly Pro Ala Val Leu Thr Val Ala Leu Ile Glu Ala Val Ala Val
            500                 505                 510

tct tgg ttc tat ggc atc act cag ttc tgc agg gac gtg aag gaa atg     1584
Ser Trp Phe Tyr Gly Ile Thr Gln Phe Cys Arg Asp Val Lys Glu Met
        515                 520                 525

ctc ggc ttc agc ccg ggg tgg ttc tgg agg atc tgc tgg gtg gcc atc     1632
Leu Gly Phe Ser Pro Gly Trp Phe Trp Arg Ile Cys Trp Val Ala Ile
    530                 535                 540

agc cct ctg ttt ctc ctg ttc atc att tgc agt ttt ctg atg agc ccg     1680
Ser Pro Leu Phe Leu Leu Phe Ile Ile Cys Ser Phe Leu Met Ser Pro
545                 550                 555                 560

cca caa cta cga ctt ttc caa tat aat tat cct tac tgg agt atc atc     1728
Pro Gln Leu Arg Leu Phe Gln Tyr Asn Tyr Pro Tyr Trp Ser Ile Ile
                565                 570                 575

ttg ggt tac tgc ata gga acc tca tct ttc att tgc atc ccc aca tat     1776
Leu Gly Tyr Cys Ile Gly Thr Ser Ser Phe Ile Cys Ile Pro Thr Tyr
            580                 585                 590

ata gct tat cgg ttg atc atc act cca ggg aca ttt aaa gag cgt att     1824
Ile Ala Tyr Arg Leu Ile Ile Thr Pro Gly Thr Phe Lys Glu Arg Ile
        595                 600                 605

att aaa agt att acc cca gaa aca cca aca gaa att cct tgt ggg gac     1872
Ile Lys Ser Ile Thr Pro Glu Thr Pro Thr Glu Ile Pro Cys Gly Asp
    610                 615                 620

atc cgc ttg aat gct gtg taa                                         1893
Ile Arg Leu Asn Ala Val
625                 630


<210> SEQ ID NO 4
<211> LENGTH: 630
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 4

Met Glu Thr Thr Pro Leu Asn Ser Gln Lys Gln Leu Ser Ala Cys Glu
  1               5                  10                  15

Asp Gly Glu Asp Cys Gln Glu Asn Gly Val Leu Gln Lys Val Val Pro
             20                  25                  30
```

-continued

```
Thr Pro Gly Asp Lys Val Glu Ser Gly Gln Ile Ser Asn Gly Tyr Ser
        35                  40                  45

Ala Val Pro Ser Pro Gly Ala Gly Asp Asp Thr Arg His Ser Ile Pro
    50                  55                  60

Ala Thr Thr Thr Thr Leu Val Ala Glu Leu His Gln Gly Glu Arg Glu
 65                  70                  75                  80

Thr Trp Gly Lys Lys Val Asp Phe Leu Leu Ser Val Ile Gly Tyr Ala
                85                  90                  95

Val Asp Leu Gly Asn Val Trp Arg Phe Pro Tyr Ile Cys Tyr Gln Asn
            100                 105                 110

Gly Gly Gly Ala Phe Leu Leu Pro Tyr Thr Ile Met Ala Ile Phe Gly
        115                 120                 125

Gly Ile Pro Leu Phe Tyr Met Glu Leu Ala Leu Gly Gln Tyr His Arg
    130                 135                 140

Asn Gly Cys Ile Ser Ile Trp Arg Lys Ile Cys Pro Ile Phe Lys Gly
145                 150                 155                 160

Ile Gly Tyr Ala Ile Cys Ile Ile Ala Phe Tyr Met Ala Ser Tyr Tyr
                165                 170                 175

Asn Thr Ile Met Ala Trp Ala Leu Tyr Tyr Leu Ile Ser Ser Phe Thr
            180                 185                 190

Asp Gln Leu Pro Trp Thr Ser Cys Lys Asn Ser Trp Asn Thr Gly Asn
        195                 200                 205

Cys Thr Asn Tyr Phe Ser Glu Asp Asn Ile Thr Trp Thr Leu His Ser
    210                 215                 220

Thr Ser Pro Ala Glu Glu Phe Tyr Thr Arg His Val Leu Gln Ile His
225                 230                 235                 240

Arg Ser Lys Gly Leu Gln Asp Leu Gly Gly Ile Ser Trp Gln Leu Ala
                245                 250                 255

Leu Cys Ile Met Leu Ile Phe Thr Val Ile Tyr Phe Ser Ile Trp Lys
            260                 265                 270

Gly Val Lys Thr Ser Gly Lys Val Val Trp Val Thr Ala Thr Phe Pro
        275                 280                 285

Tyr Ile Ile Leu Ser Val Leu Leu Val Arg Gly Ala Thr Leu Pro Gly
    290                 295                 300

Ala Trp Arg Gly Val Leu Phe Tyr Leu Lys Pro Asn Trp Gln Lys Leu
305                 310                 315                 320

Leu Glu Thr Gly Val Trp Ile Asp Ala Ala Ala Gln Ile Phe Phe Ser
                325                 330                 335

Leu Gly Pro Gly Phe Gly Val Leu Leu Ala Phe Ala Ser Tyr Asn Lys
            340                 345                 350

Phe Asn Asn Asn Cys Tyr Gln Asp Ala Leu Val Thr Ser Val Val Asn
        355                 360                 365

Cys Met Thr Ser Phe Val Ser Gly Phe Val Ile Phe Thr Val Leu Gly
    370                 375                 380

Tyr Met Ala Glu Met Arg Asn Glu Asp Val Ser Glu Val Ala Lys Asp
385                 390                 395                 400

Ala Gly Pro Ser Leu Leu Phe Ile Thr Tyr Ala Glu Ala Ile Ala Asn
                405                 410                 415

Met Pro Ala Ser Thr Phe Phe Ala Ile Ile Phe Phe Leu Met Leu Ile
            420                 425                 430

Thr Leu Gly Leu Asp Ser Thr Phe Ala Gly Leu Glu Gly Val Ile Thr
        435                 440                 445
```

-continued

```
Ala Val Leu Asp Glu Phe Pro His Val Trp Ala Lys Arg Arg Glu Arg
    450                 455                 460

Phe Val Leu Ala Val Val Ile Thr Cys Phe Phe Gly Ser Leu Val Thr
465                 470                 475                 480

Leu Thr Phe Gly Gly Ala Tyr Val Val Lys Leu Leu Glu Glu Tyr Ala
                485                 490                 495

Thr Gly Pro Ala Val Leu Thr Val Ala Leu Ile Glu Ala Val Ala Val
            500                 505                 510

Ser Trp Phe Tyr Gly Ile Thr Gln Phe Cys Arg Asp Val Lys Glu Met
        515                 520                 525

Leu Gly Phe Ser Pro Gly Trp Phe Trp Arg Ile Cys Trp Val Ala Ile
    530                 535                 540

Ser Pro Leu Phe Leu Leu Phe Ile Ile Cys Ser Phe Leu Met Ser Pro
545                 550                 555                 560

Pro Gln Leu Arg Leu Phe Gln Tyr Asn Tyr Pro Tyr Trp Ser Ile Ile
                565                 570                 575

Leu Gly Tyr Cys Ile Gly Thr Ser Ser Phe Ile Cys Ile Pro Thr Tyr
            580                 585                 590

Ile Ala Tyr Arg Leu Ile Ile Thr Pro Gly Thr Phe Lys Glu Arg Ile
        595                 600                 605

Ile Lys Ser Ile Thr Pro Glu Thr Pro Thr Glu Ile Pro Cys Gly Asp
    610                 615                 620

Ile Arg Leu Asn Ala Val
625                 630


<210> SEQ ID NO 5
<211> LENGTH: 1893
<212> TYPE: DNA
<213> ORGANISM: Mus musculus
<220> FEATURE:
<221> NAME/KEY: CDS
<222> LOCATION: (1)..(1893)

<400> SEQUENCE: 5

atg gag acc aca cct ttg aat tct cag aaa gtg ctg tca gag tgt aag       48
Met Glu Thr Thr Pro Leu Asn Ser Gln Lys Val Leu Ser Glu Cys Lys
  1               5                  10                  15

gac aaa gag gac tgc caa gaa aat ggt gtt ctg cag aag ggt gtc ccc       96
Asp Lys Glu Asp Cys Gln Glu Asn Gly Val Leu Gln Lys Gly Val Pro
             20                  25                  30

aca cca gca gac aag gca gag cct gga caa ata tcc aat ggg tac tcc      144
Thr Pro Ala Asp Lys Ala Glu Pro Gly Gln Ile Ser Asn Gly Tyr Ser
         35                  40                  45

gca gtt ccc agt aca agc gct ggg gat gaa gcg cca cac tct acg cca      192
Ala Val Pro Ser Thr Ser Ala Gly Asp Glu Ala Pro His Ser Thr Pro
     50                  55                  60

gct gcc acc acc acc ctg gtg gct gag att cac caa ggg gaa cgg gag      240
Ala Ala Thr Thr Thr Leu Val Ala Glu Ile His Gln Gly Glu Arg Glu
 65                  70                  75                  80

acc tgg ggc aag aag atg gat ttc ctc ctg tct gtc att ggc tat gcc      288
Thr Trp Gly Lys Lys Met Asp Phe Leu Leu Ser Val Ile Gly Tyr Ala
                 85                  90                  95

gtg gac ctg ggc aac atc tgg cgt ttt ccc tac ata tgc tac cag aat      336
Val Asp Leu Gly Asn Ile Trp Arg Phe Pro Tyr Ile Cys Tyr Gln Asn
            100                 105                 110

ggt gga ggg gcc ttc ctc ctc cct tac acc atc atg gcc atc ttt ggg      384
Gly Gly Gly Ala Phe Leu Leu Pro Tyr Thr Ile Met Ala Ile Phe Gly
        115                 120                 125
```

-continued

```
ggg atc ccg ctc ttc tac atg gag ctc gcc ctg ggc cag tac cac cga      432
Gly Ile Pro Leu Phe Tyr Met Glu Leu Ala Leu Gly Gln Tyr His Arg
    130                 135                 140

aat ggg tgc att tct ata tgg agg aag atc tgc ccg att ttc aaa ggc      480
Asn Gly Cys Ile Ser Ile Trp Arg Lys Ile Cys Pro Ile Phe Lys Gly
145                 150                 155                 160

att ggc tat gcc atc tgc atc att gcc ttt tat atc gcc tcc tac tat      528
Ile Gly Tyr Ala Ile Cys Ile Ile Ala Phe Tyr Ile Ala Ser Tyr Tyr
                165                 170                 175

aac acc atc ata gcc tgg gcg ctc tac tac ctc atc tcc tcc ttc acg      576
Asn Thr Ile Ile Ala Trp Ala Leu Tyr Tyr Leu Ile Ser Ser Phe Thr
            180                 185                 190

gac cag ctg ccc tgg acc agc tgc aag aac tct tgg aac act ggc aac      624
Asp Gln Leu Pro Trp Thr Ser Cys Lys Asn Ser Trp Asn Thr Gly Asn
        195                 200                 205

tgc acc aac tac ttc gcc cag gac aac atc acc tgg aca ctc cat tcc      672
Cys Thr Asn Tyr Phe Ala Gln Asp Asn Ile Thr Trp Thr Leu His Ser
    210                 215                 220

acg tca cct gct gag gag ttt tac ttg cgc cat gtc ctg cag atc cat      720
Thr Ser Pro Ala Glu Glu Phe Tyr Leu Arg His Val Leu Gln Ile His
225                 230                 235                 240

cag tca aag gga ctc cag gac ctg ggg acc atc agc tgg cag ctg gct      768
Gln Ser Lys Gly Leu Gln Asp Leu Gly Thr Ile Ser Trp Gln Leu Ala
                245                 250                 255

ctc tgc atc atg ctc atc ttc acc att atc tac ttc agc atc tgg aaa      816
Leu Cys Ile Met Leu Ile Phe Thr Ile Ile Tyr Phe Ser Ile Trp Lys
            260                 265                 270

gga gtc aaa acg tct ggc aag gtg gtg tgg gtg aca gcc acc ttc cct      864
Gly Val Lys Thr Ser Gly Lys Val Val Trp Val Thr Ala Thr Phe Pro
        275                 280                 285

tac att gtc ctt tct gtc ctg ctg gtg agg gga gcc acc ctt cct gga      912
Tyr Ile Val Leu Ser Val Leu Leu Val Arg Gly Ala Thr Leu Pro Gly
    290                 295                 300

gcc tgg aga ggg gtt gtc ttt tac ttg aaa ccc aac tgg cag aaa ctc      960
Ala Trp Arg Gly Val Val Phe Tyr Leu Lys Pro Asn Trp Gln Lys Leu
305                 310                 315                 320

ttg gag aca ggg gtg tgg gtt gat gct gcg gct cag atc ttt ttc tct     1008
Leu Glu Thr Gly Val Trp Val Asp Ala Ala Ala Gln Ile Phe Phe Ser
                325                 330                 335

ctt ggc ccg ggg ttt ggg gtt ctc ctg gcg ttt gct agc tac aac aag     1056
Leu Gly Pro Gly Phe Gly Val Leu Leu Ala Phe Ala Ser Tyr Asn Lys
            340                 345                 350

ttc aac aac aac tgt tac caa gat gcc ctg gtg acc agt gtg gtg aac     1104
Phe Asn Asn Asn Cys Tyr Gln Asp Ala Leu Val Thr Ser Val Val Asn
        355                 360                 365

tgc atg acg agc ttc gtc tct ggc ttt gtc atc ttc acg gtg ctt ggc     1152
Cys Met Thr Ser Phe Val Ser Gly Phe Val Ile Phe Thr Val Leu Gly
    370                 375                 380

tac atg gct gag atg agg aac gaa gac gtg tcc gag gtg gcc aaa gac     1200
Tyr Met Ala Glu Met Arg Asn Glu Asp Val Ser Glu Val Ala Lys Asp
385                 390                 395                 400

gcg ggc ccc agc ctc ctt ttc atc aca tat gcg gag gca ata gct aac     1248
Ala Gly Pro Ser Leu Leu Phe Ile Thr Tyr Ala Glu Ala Ile Ala Asn
                405                 410                 415

atg cca gca tcc aca ttc ttt gcc atc atc ttc ttc ctc atg tta atc     1296
Met Pro Ala Ser Thr Phe Phe Ala Ile Ile Phe Phe Leu Met Leu Ile
            420                 425                 430

acg ctg ggt ttg gat agc acg ttt gca ggc ctg gaa ggt gtg atc aca     1344
Thr Leu Gly Leu Asp Ser Thr Phe Ala Gly Leu Glu Gly Val Ile Thr
        435                 440                 445
```

-continued

```
gct gtg ttg gat gag ttt cct cac atc tgg gcc aag cgc agg gaa tgg      1392
Ala Val Leu Asp Glu Phe Pro His Ile Trp Ala Lys Arg Arg Glu Trp
    450                 455                 460

ttt gtg ctc atc gtg gtc atc act tgc atc ttg gga tcc ctg ctc aca      1440
Phe Val Leu Ile Val Val Ile Thr Cys Ile Leu Gly Ser Leu Leu Thr
465                 470                 475                 480

ctg aca tca gga ggg gcg tat gtg gtg acc ctg ctg gag gag tac gcc      1488
Leu Thr Ser Gly Gly Ala Tyr Val Val Thr Leu Leu Glu Glu Tyr Ala
                485                 490                 495

acg ggg cca gca gtg ctc act gtg gct ctc atc gag gcc gtc gtc gtg      1536
Thr Gly Pro Ala Val Leu Thr Val Ala Leu Ile Glu Ala Val Val Val
            500                 505                 510

tct tgg ttc tat gga atc act cag ttc tgc agc gac gtg aag gaa atg      1584
Ser Trp Phe Tyr Gly Ile Thr Gln Phe Cys Ser Asp Val Lys Glu Met
        515                 520                 525

ctg ggc ttc agc ccc gga tgg ttt tgg agg atc tgc tgg gtg gcc atc      1632
Leu Gly Phe Ser Pro Gly Trp Phe Trp Arg Ile Cys Trp Val Ala Ile
    530                 535                 540

agt cct ctg ttt ctc ctg ttc atc att tgc agt ttt ttg atg agt cca      1680
Ser Pro Leu Phe Leu Leu Phe Ile Ile Cys Ser Phe Leu Met Ser Pro
545                 550                 555                 560

ccc caa ctc cgg ctt ttc caa tac aat tat ccc cac tgg agt atc atc      1728
Pro Gln Leu Arg Leu Phe Gln Tyr Asn Tyr Pro His Trp Ser Ile Ile
                565                 570                 575

ttg ggc tac tgc ata gga aca tcg tct gtc atc tgc atc cct ata tac      1776
Leu Gly Tyr Cys Ile Gly Thr Ser Ser Val Ile Cys Ile Pro Ile Tyr
            580                 585                 590

atc att tat cgg ctg atc agc act cca ggg aca ctt aag gag cgc att      1824
Ile Ile Tyr Arg Leu Ile Ser Thr Pro Gly Thr Leu Lys Glu Arg Ile
        595                 600                 605

att aaa agt atc act cct gaa aca cca acg gaa att ccg tgt ggg gac      1872
Ile Lys Ser Ile Thr Pro Glu Thr Pro Thr Glu Ile Pro Cys Gly Asp
    610                 615                 620

atc cgc atg aat gct gtg taa                                          1893
Ile Arg Met Asn Ala Val
625                 630


<210> SEQ ID NO 6
<211> LENGTH: 630
<212> TYPE: PRT
<213> ORGANISM: Mus musculus

<400> SEQUENCE: 6

Met Glu Thr Thr Pro Leu Asn Ser Gln Lys Val Leu Ser Glu Cys Lys
  1               5                  10                  15

Asp Lys Glu Asp Cys Gln Glu Asn Gly Val Leu Gln Lys Gly Val Pro
             20                  25                  30

Thr Pro Ala Asp Lys Ala Glu Pro Gly Gln Ile Ser Asn Gly Tyr Ser
         35                  40                  45

Ala Val Pro Ser Thr Ser Ala Gly Asp Glu Ala Pro His Ser Thr Pro
     50                  55                  60

Ala Ala Thr Thr Thr Leu Val Ala Glu Ile His Gln Gly Glu Arg Glu
 65                  70                  75                  80

Thr Trp Gly Lys Lys Met Asp Phe Leu Leu Ser Val Ile Gly Tyr Ala
                 85                  90                  95

Val Asp Leu Gly Asn Ile Trp Arg Phe Pro Tyr Ile Cys Tyr Gln Asn
            100                 105                 110

Gly Gly Gly Ala Phe Leu Leu Pro Tyr Thr Ile Met Ala Ile Phe Gly
```

-continued

```
        115                 120                 125

Gly Ile Pro Leu Phe Tyr Met Glu Leu Ala Leu Gly Gln Tyr His Arg
    130                 135                 140

Asn Gly Cys Ile Ser Ile Trp Arg Lys Ile Cys Pro Ile Phe Lys Gly
145                 150                 155                 160

Ile Gly Tyr Ala Ile Cys Ile Ile Ala Phe Tyr Ile Ala Ser Tyr Tyr
                165                 170                 175

Asn Thr Ile Ile Ala Trp Ala Leu Tyr Tyr Leu Ile Ser Ser Phe Thr
            180                 185                 190

Asp Gln Leu Pro Trp Thr Ser Cys Lys Asn Ser Trp Asn Thr Gly Asn
        195                 200                 205

Cys Thr Asn Tyr Phe Ala Gln Asp Asn Ile Thr Trp Thr Leu His Ser
    210                 215                 220

Thr Ser Pro Ala Glu Glu Phe Tyr Leu Arg His Val Leu Gln Ile His
225                 230                 235                 240

Gln Ser Lys Gly Leu Gln Asp Leu Gly Thr Ile Ser Trp Gln Leu Ala
                245                 250                 255

Leu Cys Ile Met Leu Ile Phe Thr Ile Ile Tyr Phe Ser Ile Trp Lys
            260                 265                 270

Gly Val Lys Thr Ser Gly Lys Val Val Trp Val Thr Ala Thr Phe Pro
        275                 280                 285

Tyr Ile Val Leu Ser Val Leu Leu Val Arg Gly Ala Thr Leu Pro Gly
    290                 295                 300

Ala Trp Arg Gly Val Val Phe Tyr Leu Lys Pro Asn Trp Gln Lys Leu
305                 310                 315                 320

Leu Glu Thr Gly Val Trp Val Asp Ala Ala Ala Gln Ile Phe Phe Ser
                325                 330                 335

Leu Gly Pro Gly Phe Gly Val Leu Leu Ala Phe Ala Ser Tyr Asn Lys
            340                 345                 350

Phe Asn Asn Asn Cys Tyr Gln Asp Ala Leu Val Thr Ser Val Val Asn
        355                 360                 365

Cys Met Thr Ser Phe Val Ser Gly Phe Val Ile Phe Thr Val Leu Gly
    370                 375                 380

Tyr Met Ala Glu Met Arg Asn Glu Asp Val Ser Glu Val Ala Lys Asp
385                 390                 395                 400

Ala Gly Pro Ser Leu Leu Phe Ile Thr Tyr Ala Glu Ala Ile Ala Asn
                405                 410                 415

Met Pro Ala Ser Thr Phe Phe Ala Ile Ile Phe Phe Leu Met Leu Ile
            420                 425                 430

Thr Leu Gly Leu Asp Ser Thr Phe Ala Gly Leu Glu Gly Val Ile Thr
        435                 440                 445

Ala Val Leu Asp Glu Phe Pro His Ile Trp Ala Lys Arg Arg Glu Trp
    450                 455                 460

Phe Val Leu Ile Val Val Ile Thr Cys Ile Leu Gly Ser Leu Leu Thr
465                 470                 475                 480

Leu Thr Ser Gly Gly Ala Tyr Val Val Thr Leu Leu Glu Glu Tyr Ala
                485                 490                 495

Thr Gly Pro Ala Val Leu Thr Val Ala Leu Ile Glu Ala Val Val Val
            500                 505                 510

Ser Trp Phe Tyr Gly Ile Thr Gln Phe Cys Ser Asp Val Lys Glu Met
        515                 520                 525

Leu Gly Phe Ser Pro Gly Trp Phe Trp Arg Ile Cys Trp Val Ala Ile
    530                 535                 540
```

-continued

```
Ser Pro Leu Phe Leu Leu Phe Ile Ile Cys Ser Phe Leu Met Ser Pro
545                 550                 555                 560

Pro Gln Leu Arg Leu Phe Gln Tyr Asn Tyr Pro His Trp Ser Ile Ile
                565                 570                 575

Leu Gly Tyr Cys Ile Gly Thr Ser Ser Val Ile Cys Ile Pro Ile Tyr
            580                 585                 590

Ile Ile Tyr Arg Leu Ile Ser Thr Pro Gly Thr Leu Lys Glu Arg Ile
        595                 600                 605

Ile Lys Ser Ile Thr Pro Glu Thr Pro Thr Glu Ile Pro Cys Gly Asp
    610                 615                 620

Ile Arg Met Asn Ala Val
625                 630


<210> SEQ ID NO 7
<211> LENGTH: 1893
<212> TYPE: DNA
<213> ORGANISM: Artificial Sequence
<220> FEATURE:
<223> OTHER INFORMATION: Description of Artificial Sequence:  Synthetic
      Primer
<220> FEATURE:
<221> NAME/KEY: CDS
<222> LOCATION: (1)..(1893)

<400> SEQUENCE: 7

atg gag acc aca cct ttg aat tct cag aaa gtg ctg tca gag tgt aag       48
Met Glu Thr Thr Pro Leu Asn Ser Gln Lys Val Leu Ser Glu Cys Lys
  1               5                  10                  15

gac aaa gag gac tgc caa gaa aat ggt gtt ctg cag aag ggt gtc ccc       96
Asp Lys Glu Asp Cys Gln Glu Asn Gly Val Leu Gln Lys Gly Val Pro
             20                  25                  30

aca cca gca gac aag gca gag cct gga caa ata tcc aat ggg tac tcc      144
Thr Pro Ala Asp Lys Ala Glu Pro Gly Gln Ile Ser Asn Gly Tyr Ser
         35                  40                  45

gca gtt ccc agt aca agc gct ggg gat gaa gcg cca cac tct acg cca      192
Ala Val Pro Ser Thr Ser Ala Gly Asp Glu Ala Pro His Ser Thr Pro
     50                  55                  60

gct gcc acc acc acc ctg gtg gct gag att cac caa ggg gaa cgg gag      240
Ala Ala Thr Thr Thr Leu Val Ala Glu Ile His Gln Gly Glu Arg Glu
 65                  70                  75                  80

acc tgg ggc aag aag atg gat ttc ctc ctg tct gtc att ggc tat gcc      288
Thr Trp Gly Lys Lys Met Asp Phe Leu Leu Ser Val Ile Gly Tyr Ala
                 85                  90                  95

gtg gac ctg ggc aac atc tgg cgt ttt ccc tac ata tgc tac cag aat      336
Val Asp Leu Gly Asn Ile Trp Arg Phe Pro Tyr Ile Cys Tyr Gln Asn
            100                 105                 110

ggt gga ggg gcc ttc ctc ctc cct tac acc atc atg gcc atc ttt ggg      384
Gly Gly Gly Ala Phe Leu Leu Pro Tyr Thr Ile Met Ala Ile Phe Gly
        115                 120                 125

ggg atc ccg ctc ttc tac atg gag ctc gcc ctg ggc cag tac cac cga      432
Gly Ile Pro Leu Phe Tyr Met Glu Leu Ala Leu Gly Gln Tyr His Arg
    130                 135                 140

aat ggg tgc att tct ata tgg agg aag atc tgc ccg att ttc aaa ggc      480
Asn Gly Cys Ile Ser Ile Trp Arg Lys Ile Cys Pro Ile Phe Lys Gly
145                 150                 155                 160

att ggc tat gcc atc tgc atc att gcc ttt tat atg gcc tcc tac tat      528
Ile Gly Tyr Ala Ile Cys Ile Ile Ala Phe Tyr Met Ala Ser Tyr Tyr
                165                 170                 175

aac acc atc ata gcc tgg gcg ctc tac tac ctc atc tcc tcc ttc acg      576
Asn Thr Ile Ile Ala Trp Ala Leu Tyr Tyr Leu Ile Ser Ser Phe Thr
```

-continued

```
            180                 185                 190

gac cag ctg ccc tgg acc agc tgc aag aac tct tgg aac act ggc aac      624
Asp Gln Leu Pro Trp Thr Ser Cys Lys Asn Ser Trp Asn Thr Gly Asn
        195                 200                 205

tgc acc aac tac ttc gcc cag gac aac atc acc tgg aca ctc cat tcc      672
Cys Thr Asn Tyr Phe Ala Gln Asp Asn Ile Thr Trp Thr Leu His Ser
    210                 215                 220

acg tca cct gct gag gag ttt tac ttg cgc cat gtc ctg cag atc cat      720
Thr Ser Pro Ala Glu Glu Phe Tyr Leu Arg His Val Leu Gln Ile His
225                 230                 235                 240

cag tca aag gga ctc cag gac ctg ggg acc atc agc tgg cag ctg gct      768
Gln Ser Lys Gly Leu Gln Asp Leu Gly Thr Ile Ser Trp Gln Leu Ala
                245                 250                 255

ctc tgc atc atg ctc atc ttc acc att atc tac ttc agc atc tgg aaa      816
Leu Cys Ile Met Leu Ile Phe Thr Ile Ile Tyr Phe Ser Ile Trp Lys
            260                 265                 270

gga gtc aaa acg tct ggc aag gtg gtg tgg gtg aca gcc acc ttc cct      864
Gly Val Lys Thr Ser Gly Lys Val Val Trp Val Thr Ala Thr Phe Pro
        275                 280                 285

tac att gtc ctt tct gtc ctg ctg gtg agg gga gcc acc ctt cct gga      912
Tyr Ile Val Leu Ser Val Leu Leu Val Arg Gly Ala Thr Leu Pro Gly
    290                 295                 300

gcc tgg aga ggg gtt gtc ttt tac ttg aaa ccc aac tgg cag aaa ctc      960
Ala Trp Arg Gly Val Val Phe Tyr Leu Lys Pro Asn Trp Gln Lys Leu
305                 310                 315                 320

ttg gag aca ggg gtg tgg gtt gat gct gcg gct cag atc ttt ttc tct     1008
Leu Glu Thr Gly Val Trp Val Asp Ala Ala Ala Gln Ile Phe Phe Ser
                325                 330                 335

ctt ggc ccg ggg ttt ggg gtt ctc ctg gcg ttt gct agc tac aac aag     1056
Leu Gly Pro Gly Phe Gly Val Leu Leu Ala Phe Ala Ser Tyr Asn Lys
            340                 345                 350

ttc aac aac aac tgt tac caa gat gcc ctg gtg acc agt gtg gtg aac     1104
Phe Asn Asn Asn Cys Tyr Gln Asp Ala Leu Val Thr Ser Val Val Asn
        355                 360                 365

tgc atg acg agc ttc gtc tct ggc ttt gtc atc ttc acg gtg ctt ggc     1152
Cys Met Thr Ser Phe Val Ser Gly Phe Val Ile Phe Thr Val Leu Gly
    370                 375                 380

tac atg gct gag atg agg aac gaa gac gtg tcc gag gtg gcc aaa gac     1200
Tyr Met Ala Glu Met Arg Asn Glu Asp Val Ser Glu Val Ala Lys Asp
385                 390                 395                 400

gcg ggc ccc agc ctc ctt ttc atc aca tat gcg gag gca ata gct aac     1248
Ala Gly Pro Ser Leu Leu Phe Ile Thr Tyr Ala Glu Ala Ile Ala Asn
                405                 410                 415

atg cca gca tcc aca ttc ttt gcc atc atc ttc ttc ctc atg tta atc     1296
Met Pro Ala Ser Thr Phe Phe Ala Ile Ile Phe Phe Leu Met Leu Ile
            420                 425                 430

acg ctg ggt ttg gat agc acg ttt gca ggc ctg gaa ggt gtg atc aca     1344
Thr Leu Gly Leu Asp Ser Thr Phe Ala Gly Leu Glu Gly Val Ile Thr
        435                 440                 445

gct gtg ttg gat gag ttt cct cac atc tgg gcc aag cgc agg gaa tgg     1392
Ala Val Leu Asp Glu Phe Pro His Ile Trp Ala Lys Arg Arg Glu Trp
    450                 455                 460

ttt gtg ctc atc gtg gtc atc act tgc atc ttg gga tcc ctg ctc aca     1440
Phe Val Leu Ile Val Val Ile Thr Cys Ile Leu Gly Ser Leu Leu Thr
465                 470                 475                 480

ctg aca tca gga ggg gcg tat gtg gtg acc ctg ctg gag gag tac gcc     1488
Leu Thr Ser Gly Gly Ala Tyr Val Val Thr Leu Leu Glu Glu Tyr Ala
                485                 490                 495

acg ggg cca gca gtg ctc act gtg gct ctc atc gag gcc gtc gtc gtg     1536
```

-continued

```
Thr Gly Pro Ala Val Leu Thr Val Ala Leu Ile Glu Ala Val Val Val
            500                 505                 510

tct tgg ttc tat gga atc act cag ttc tgc agc gac gtg aag gaa atg     1584
Ser Trp Phe Tyr Gly Ile Thr Gln Phe Cys Ser Asp Val Lys Glu Met
        515                 520                 525

ctg ggc ttc agc ccc gga tgg ttt tgg agg atc tgc tgg gtg gcc atc     1632
Leu Gly Phe Ser Pro Gly Trp Phe Trp Arg Ile Cys Trp Val Ala Ile
    530                 535                 540

agt cct ctg ttt ctc ctg ttc atc att tgc agt ttt ttg atg agt cca     1680
Ser Pro Leu Phe Leu Leu Phe Ile Ile Cys Ser Phe Leu Met Ser Pro
545                 550                 555                 560

ccc caa ctc cgg ctt ttc caa tac aat tat ccc cac tgg agt atc atc     1728
Pro Gln Leu Arg Leu Phe Gln Tyr Asn Tyr Pro His Trp Ser Ile Ile
                565                 570                 575

ttg ggc tac tgc ata gga aca tcg tct gtc atc tgc atc cct ata tac     1776
Leu Gly Tyr Cys Ile Gly Thr Ser Ser Val Ile Cys Ile Pro Ile Tyr
            580                 585                 590

atc att tat cgg ctg atc agc act cca ggg aca ctt aag gag cgc att     1824
Ile Ile Tyr Arg Leu Ile Ser Thr Pro Gly Thr Leu Lys Glu Arg Ile
        595                 600                 605

att aaa agt atc act cct gaa aca cca acg gaa att ccg tgt ggg gac     1872
Ile Lys Ser Ile Thr Pro Glu Thr Pro Thr Glu Ile Pro Cys Gly Asp
    610                 615                 620

atc cgc atg aat gct gtg taa                                         1893
Ile Arg Met Asn Ala Val
625                 630


<210> SEQ ID NO 8
<211> LENGTH: 630
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 8

Met Glu Thr Thr Pro Leu Asn Ser Gln Lys Val Leu Ser Glu Cys Lys
  1               5                  10                  15

Asp Lys Glu Asp Cys Gln Glu Asn Gly Val Leu Gln Lys Gly Val Pro
            20                  25                  30

Thr Pro Ala Asp Lys Ala Glu Pro Gly Gln Ile Ser Asn Gly Tyr Ser
        35                  40                  45

Ala Val Pro Ser Thr Ser Ala Gly Asp Glu Ala Pro His Ser Thr Pro
    50                  55                  60

Ala Ala Thr Thr Thr Leu Val Ala Glu Ile His Gln Gly Glu Arg Glu
 65                  70                  75                  80

Thr Trp Gly Lys Lys Met Asp Phe Leu Leu Ser Val Ile Gly Tyr Ala
                 85                  90                  95

Val Asp Leu Gly Asn Ile Trp Arg Phe Pro Tyr Ile Cys Tyr Gln Asn
            100                 105                 110

Gly Gly Gly Ala Phe Leu Leu Pro Tyr Thr Ile Met Ala Ile Phe Gly
        115                 120                 125

Gly Ile Pro Leu Phe Tyr Met Glu Leu Ala Leu Gly Gln Tyr His Arg
    130                 135                 140

Asn Gly Cys Ile Ser Ile Trp Arg Lys Ile Cys Pro Ile Phe Lys Gly
145                 150                 155                 160

Ile Gly Tyr Ala Ile Cys Ile Ile Ala Phe Tyr Met Ala Ser Tyr Tyr
                165                 170                 175
```

-continued

```
Asn Thr Ile Ile Ala Trp Ala Leu Tyr Tyr Leu Ile Ser Ser Phe Thr
            180                 185                 190

Asp Gln Leu Pro Trp Thr Ser Cys Lys Asn Ser Trp Asn Thr Gly Asn
        195                 200                 205

Cys Thr Asn Tyr Phe Ala Gln Asp Asn Ile Thr Trp Thr Leu His Ser
    210                 215                 220

Thr Ser Pro Ala Glu Glu Phe Tyr Leu Arg His Val Leu Gln Ile His
225                 230                 235                 240

Gln Ser Lys Gly Leu Gln Asp Leu Gly Thr Ile Ser Trp Gln Leu Ala
                245                 250                 255

Leu Cys Ile Met Leu Ile Phe Thr Ile Ile Tyr Phe Ser Ile Trp Lys
            260                 265                 270

Gly Val Lys Thr Ser Gly Lys Val Val Trp Val Thr Ala Thr Phe Pro
        275                 280                 285

Tyr Ile Val Leu Ser Val Leu Leu Val Arg Gly Ala Thr Leu Pro Gly
    290                 295                 300

Ala Trp Arg Gly Val Val Phe Tyr Leu Lys Pro Asn Trp Gln Lys Leu
305                 310                 315                 320

Leu Glu Thr Gly Val Trp Val Asp Ala Ala Ala Gln Ile Phe Phe Ser
                325                 330                 335

Leu Gly Pro Gly Phe Gly Val Leu Leu Ala Phe Ala Ser Tyr Asn Lys
            340                 345                 350

Phe Asn Asn Asn Cys Tyr Gln Asp Ala Leu Val Thr Ser Val Val Asn
        355                 360                 365

Cys Met Thr Ser Phe Val Ser Gly Phe Val Ile Phe Thr Val Leu Gly
    370                 375                 380

Tyr Met Ala Glu Met Arg Asn Glu Asp Val Ser Glu Val Ala Lys Asp
385                 390                 395                 400

Ala Gly Pro Ser Leu Leu Phe Ile Thr Tyr Ala Glu Ala Ile Ala Asn
                405                 410                 415

Met Pro Ala Ser Thr Phe Phe Ala Ile Ile Phe Phe Leu Met Leu Ile
            420                 425                 430

Thr Leu Gly Leu Asp Ser Thr Phe Ala Gly Leu Glu Gly Val Ile Thr
        435                 440                 445

Ala Val Leu Asp Glu Phe Pro His Ile Trp Ala Lys Arg Arg Glu Trp
    450                 455                 460

Phe Val Leu Ile Val Val Ile Thr Cys Ile Leu Gly Ser Leu Leu Thr
465                 470                 475                 480

Leu Thr Ser Gly Gly Ala Tyr Val Val Thr Leu Leu Glu Glu Tyr Ala
                485                 490                 495

Thr Gly Pro Ala Val Leu Thr Val Ala Leu Ile Glu Ala Val Val Val
            500                 505                 510

Ser Trp Phe Tyr Gly Ile Thr Gln Phe Cys Ser Asp Val Lys Glu Met
        515                 520                 525

Leu Gly Phe Ser Pro Gly Trp Phe Trp Arg Ile Cys Trp Val Ala Ile
    530                 535                 540

Ser Pro Leu Phe Leu Leu Phe Ile Ile Cys Ser Phe Leu Met Ser Pro
545                 550                 555                 560

Pro Gln Leu Arg Leu Phe Gln Tyr Asn Tyr Pro His Trp Ser Ile Ile
                565                 570                 575

Leu Gly Tyr Cys Ile Gly Thr Ser Ser Val Ile Cys Ile Pro Ile Tyr
            580                 585                 590

Ile Ile Tyr Arg Leu Ile Ser Thr Pro Gly Thr Leu Lys Glu Arg Ile
```

-continued

```
        595                 600                 605

Ile Lys Ser Ile Thr Pro Glu Thr Pro Thr Glu Ile Pro Cys Gly Asp
    610                 615                 620

Ile Arg Met Asn Ala Val
625                 630


<210> SEQ ID NO 9
<211> LENGTH: 1893
<212> TYPE: DNA
<213> ORGANISM: Artificial Sequence
<220> FEATURE:
<221> NAME/KEY: CDS
<222> LOCATION: (1)..(1893)
<220> FEATURE:
<223> OTHER INFORMATION: Description of Artificial Sequence:  Synthetic
      Primer

<400> SEQUENCE: 9

atg gag acg acg ccc ttg aat tct cag aag cag cta tca gcg tgt gaa       48
Met Glu Thr Thr Pro Leu Asn Ser Gln Lys Gln Leu Ser Ala Cys Glu
  1               5                  10                  15

gat gga gaa gat tgt cag gaa aac gga gtt cta cag aag gtt gtt ccc       96
Asp Gly Glu Asp Cys Gln Glu Asn Gly Val Leu Gln Lys Val Val Pro
             20                  25                  30

acc cca ggg gac aaa gtg gag tcc ggg caa ata tcc aat ggg tac tca      144
Thr Pro Gly Asp Lys Val Glu Ser Gly Gln Ile Ser Asn Gly Tyr Ser
         35                  40                  45

gca gtt cca agt cct ggt gcg gga gat gac aca cgg cac tct atc cca      192
Ala Val Pro Ser Pro Gly Ala Gly Asp Asp Thr Arg His Ser Ile Pro
     50                  55                  60

gcg acc acc acc acc cta gtg gct gag ctt cat caa ggg gaa cgg gag      240
Ala Thr Thr Thr Thr Leu Val Ala Glu Leu His Gln Gly Glu Arg Glu
 65                  70                  75                  80

acc tgg ggc aag aag gtg gat ttc ctt ctc tca gtg att ggc tat gct      288
Thr Trp Gly Lys Lys Val Asp Phe Leu Leu Ser Val Ile Gly Tyr Ala
                 85                  90                  95

gtg gac ctg ggc aat gtc tgg cgc ttc ccc tac ata tgt tac cag aat      336
Val Asp Leu Gly Asn Val Trp Arg Phe Pro Tyr Ile Cys Tyr Gln Asn
            100                 105                 110

gga ggg ggg gca ttc ctc ctc ccc tac acc atc atg gcc att ttt ggg      384
Gly Gly Gly Ala Phe Leu Leu Pro Tyr Thr Ile Met Ala Ile Phe Gly
        115                 120                 125

gga atc ccg ctc ttt tac atg gag ctc gca ctg gga cag tac cac cga      432
Gly Ile Pro Leu Phe Tyr Met Glu Leu Ala Leu Gly Gln Tyr His Arg
    130                 135                 140

aat gga tgc att tca ata tgg agg aaa atc tgc ccg att ttc aaa ggg      480
Asn Gly Cys Ile Ser Ile Trp Arg Lys Ile Cys Pro Ile Phe Lys Gly
145                 150                 155                 160

att ggt tat gcc atc tgc atc att gcc ttt tac gct gct tcc tac tac      528
Ile Gly Tyr Ala Ile Cys Ile Ile Ala Phe Tyr Ala Ala Ser Tyr Tyr
                165                 170                 175

aac acc atc atg gcc tgg gcg cta tac tac ctc atc tcc tcc ttc acg      576
Asn Thr Ile Met Ala Trp Ala Leu Tyr Tyr Leu Ile Ser Ser Phe Thr
            180                 185                 190

gac cag ctg ccc tgg acc agc tgc aag aac tcc tgg aac act ggc aac      624
Asp Gln Leu Pro Trp Thr Ser Cys Lys Asn Ser Trp Asn Thr Gly Asn
        195                 200                 205

tgc acc aat tac ttc tcc gag gac aac atc acc tgg acc ctc cat tcc      672
Cys Thr Asn Tyr Phe Ser Glu Asp Asn Ile Thr Trp Thr Leu His Ser
    210                 215                 220

acg tcc cct gct gaa gaa ttt tac acg cgc cac gtc ctg cag atc cac      720
```

-continued

```
Thr Ser Pro Ala Glu Glu Phe Tyr Thr Arg His Val Leu Gln Ile His
225                 230                 235                 240

cgg tct aag ggg ctc cag gac ctg ggg ggc atc agc tgg cag ctg gcc      768
Arg Ser Lys Gly Leu Gln Asp Leu Gly Gly Ile Ser Trp Gln Leu Ala
                245                 250                 255

ctc tgc atc atg ctg atc ttc act gtt atc tac ttc agc atc tgg aaa      816
Leu Cys Ile Met Leu Ile Phe Thr Val Ile Tyr Phe Ser Ile Trp Lys
            260                 265                 270

ggc gtc aag acc tct ggc aag gtg gtg tgg gtg aca gcc acc ttc cct      864
Gly Val Lys Thr Ser Gly Lys Val Val Trp Val Thr Ala Thr Phe Pro
        275                 280                 285

tat atc atc ctt tct gtc ctg ctg gtg agg ggt gcc acc ctc cct gga      912
Tyr Ile Ile Leu Ser Val Leu Leu Val Arg Gly Ala Thr Leu Pro Gly
    290                 295                 300

gcc tgg agg ggt gtt ctc ttc tac ttg aaa ccc aat tgg cag aaa ctc      960
Ala Trp Arg Gly Val Leu Phe Tyr Leu Lys Pro Asn Trp Gln Lys Leu
305                 310                 315                 320

ctg gag aca ggg gtg tgg ata gat gca gcc gct cag atc ttc ttc tct     1008
Leu Glu Thr Gly Val Trp Ile Asp Ala Ala Ala Gln Ile Phe Phe Ser
                325                 330                 335

ctt ggt ccg ggc ttt ggg gtc ctg ctg gct ttt gct agc tac aac aag     1056
Leu Gly Pro Gly Phe Gly Val Leu Leu Ala Phe Ala Ser Tyr Asn Lys
            340                 345                 350

ttc aac aac aac tgc tac caa gat gcc ctg gtg acc agc gtg gtg aac     1104
Phe Asn Asn Asn Cys Tyr Gln Asp Ala Leu Val Thr Ser Val Val Asn
        355                 360                 365

tgc atg acg agc ttc gtt tcg gga ttt gtc atc ttc aca gtg ctc ggt     1152
Cys Met Thr Ser Phe Val Ser Gly Phe Val Ile Phe Thr Val Leu Gly
    370                 375                 380

tac atg gct gag atg agg aat gaa gat gtg tct gag gtg gcc aaa gac     1200
Tyr Met Ala Glu Met Arg Asn Glu Asp Val Ser Glu Val Ala Lys Asp
385                 390                 395                 400

gca ggt ccc agc ctc ctc ttc atc acg tat gca gaa gcg ata gcc aac     1248
Ala Gly Pro Ser Leu Leu Phe Ile Thr Tyr Ala Glu Ala Ile Ala Asn
                405                 410                 415

atg cca gcg tcc act ttc ttt gcc atc atc ttc ttt ctg atg tta atc     1296
Met Pro Ala Ser Thr Phe Phe Ala Ile Ile Phe Phe Leu Met Leu Ile
            420                 425                 430

acg ctg ggc ttg gac agc acg ttt gca ggc ttg gag ggg gtg atc acg     1344
Thr Leu Gly Leu Asp Ser Thr Phe Ala Gly Leu Glu Gly Val Ile Thr
        435                 440                 445

gct gtg ctg gat gag ttc cca cac gtc tgg gcc aag cgc cgg gag cgg     1392
Ala Val Leu Asp Glu Phe Pro His Val Trp Ala Lys Arg Arg Glu Arg
    450                 455                 460

ttc gtg ctc gcc gtg gtc atc acc tgc ttc ttt gga tcc ctg gtc acc     1440
Phe Val Leu Ala Val Val Ile Thr Cys Phe Phe Gly Ser Leu Val Thr
465                 470                 475                 480

ctg act ttt gga ggg gcc tac gtg gtg aag ctg ctg gag gag tat gcc     1488
Leu Thr Phe Gly Gly Ala Tyr Val Val Lys Leu Leu Glu Glu Tyr Ala
                485                 490                 495

acg ggg ccc gca gtg ctc act gtc gcg ctg atc gaa gca gtc gct gtg     1536
Thr Gly Pro Ala Val Leu Thr Val Ala Leu Ile Glu Ala Val Ala Val
            500                 505                 510

tct tgg ttc tat ggc atc act cag ttc tgc agg gac gtg aag gaa atg     1584
Ser Trp Phe Tyr Gly Ile Thr Gln Phe Cys Arg Asp Val Lys Glu Met
        515                 520                 525

ctc ggc ttc agc ccg ggg tgg ttc tgg agg atc tgc tgg gtg gcc atc     1632
Leu Gly Phe Ser Pro Gly Trp Phe Trp Arg Ile Cys Trp Val Ala Ile
    530                 535                 540
```

-continued

```
agc cct ctg ttt ctc ctg ttc atc att tgc agt ttt ctg atg agc ccg     1680
Ser Pro Leu Phe Leu Leu Phe Ile Ile Cys Ser Phe Leu Met Ser Pro
545                 550                 555                 560

cca caa cta cga ctt ttc caa tat aat tat cct tac tgg agt atc atc     1728
Pro Gln Leu Arg Leu Phe Gln Tyr Asn Tyr Pro Tyr Trp Ser Ile Ile
                565                 570                 575

ttg ggt tac tgc ata gga acc tca tct ttc att tgc atc ccc aca tat     1776
Leu Gly Tyr Cys Ile Gly Thr Ser Ser Phe Ile Cys Ile Pro Thr Tyr
            580                 585                 590

ata gct tat cgg ttg atc atc act cca ggg aca ttt aaa gag cgt att     1824
Ile Ala Tyr Arg Leu Ile Ile Thr Pro Gly Thr Phe Lys Glu Arg Ile
        595                 600                 605

att aaa agt att acc cca gaa aca cca aca gaa att cct tgt ggg gac     1872
Ile Lys Ser Ile Thr Pro Glu Thr Pro Thr Glu Ile Pro Cys Gly Asp
    610                 615                 620

atc cgc ttg aat gct gtg taa                                         1893
Ile Arg Leu Asn Ala Val
625                 630


<210> SEQ ID NO 10
<211> LENGTH: 630
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 10

Met Glu Thr Thr Pro Leu Asn Ser Gln Lys Gln Leu Ser Ala Cys Glu
  1               5                  10                  15

Asp Gly Glu Asp Cys Gln Glu Asn Gly Val Leu Gln Lys Val Val Pro
             20                  25                  30

Thr Pro Gly Asp Lys Val Glu Ser Gly Gln Ile Ser Asn Gly Tyr Ser
         35                  40                  45

Ala Val Pro Ser Pro Gly Ala Gly Asp Asp Thr Arg His Ser Ile Pro
     50                  55                  60

Ala Thr Thr Thr Thr Leu Val Ala Glu Leu His Gln Gly Glu Arg Glu
 65                  70                  75                  80

Thr Trp Gly Lys Lys Val Asp Phe Leu Leu Ser Val Ile Gly Tyr Ala
                 85                  90                  95

Val Asp Leu Gly Asn Val Trp Arg Phe Pro Tyr Ile Cys Tyr Gln Asn
            100                 105                 110

Gly Gly Gly Ala Phe Leu Leu Pro Tyr Thr Ile Met Ala Ile Phe Gly
        115                 120                 125

Gly Ile Pro Leu Phe Tyr Met Glu Leu Ala Leu Gly Gln Tyr His Arg
    130                 135                 140

Asn Gly Cys Ile Ser Ile Trp Arg Lys Ile Cys Pro Ile Phe Lys Gly
145                 150                 155                 160

Ile Gly Tyr Ala Ile Cys Ile Ile Ala Phe Tyr Ala Ala Ser Tyr Tyr
                165                 170                 175

Asn Thr Ile Met Ala Trp Ala Leu Tyr Tyr Leu Ile Ser Ser Phe Thr
            180                 185                 190

Asp Gln Leu Pro Trp Thr Ser Cys Lys Asn Ser Trp Asn Thr Gly Asn
        195                 200                 205

Cys Thr Asn Tyr Phe Ser Glu Asp Asn Ile Thr Trp Thr Leu His Ser
    210                 215                 220

Thr Ser Pro Ala Glu Glu Phe Tyr Thr Arg His Val Leu Gln Ile His
225                 230                 235                 240
```

-continued

```
Arg Ser Lys Gly Leu Gln Asp Leu Gly Gly Ile Ser Trp Gln Leu Ala
                245                 250                 255

Leu Cys Ile Met Leu Ile Phe Thr Val Ile Tyr Phe Ser Ile Trp Lys
            260                 265                 270

Gly Val Lys Thr Ser Gly Lys Val Val Trp Val Thr Ala Thr Phe Pro
        275                 280                 285

Tyr Ile Ile Leu Ser Val Leu Leu Val Arg Gly Ala Thr Leu Pro Gly
    290                 295                 300

Ala Trp Arg Gly Val Leu Phe Tyr Leu Lys Pro Asn Trp Gln Lys Leu
305                 310                 315                 320

Leu Glu Thr Gly Val Trp Ile Asp Ala Ala Ala Gln Ile Phe Phe Ser
                325                 330                 335

Leu Gly Pro Gly Phe Gly Val Leu Leu Ala Phe Ala Ser Tyr Asn Lys
            340                 345                 350

Phe Asn Asn Asn Cys Tyr Gln Asp Ala Leu Val Thr Ser Val Val Asn
        355                 360                 365

Cys Met Thr Ser Phe Val Ser Gly Phe Val Ile Phe Thr Val Leu Gly
    370                 375                 380

Tyr Met Ala Glu Met Arg Asn Glu Asp Val Ser Glu Val Ala Lys Asp
385                 390                 395                 400

Ala Gly Pro Ser Leu Leu Phe Ile Thr Tyr Ala Glu Ala Ile Ala Asn
                405                 410                 415

Met Pro Ala Ser Thr Phe Phe Ala Ile Ile Phe Phe Leu Met Leu Ile
            420                 425                 430

Thr Leu Gly Leu Asp Ser Thr Phe Ala Gly Leu Glu Gly Val Ile Thr
        435                 440                 445

Ala Val Leu Asp Glu Phe Pro His Val Trp Ala Lys Arg Arg Glu Arg
    450                 455                 460

Phe Val Leu Ala Val Val Ile Thr Cys Phe Phe Gly Ser Leu Val Thr
465                 470                 475                 480

Leu Thr Phe Gly Gly Ala Tyr Val Val Lys Leu Leu Glu Glu Tyr Ala
                485                 490                 495

Thr Gly Pro Ala Val Leu Thr Val Ala Leu Ile Glu Ala Val Ala Val
            500                 505                 510

Ser Trp Phe Tyr Gly Ile Thr Gln Phe Cys Arg Asp Val Lys Glu Met
        515                 520                 525

Leu Gly Phe Ser Pro Gly Trp Phe Trp Arg Ile Cys Trp Val Ala Ile
    530                 535                 540

Ser Pro Leu Phe Leu Leu Phe Ile Ile Cys Ser Phe Leu Met Ser Pro
545                 550                 555                 560

Pro Gln Leu Arg Leu Phe Gln Tyr Asn Tyr Pro Tyr Trp Ser Ile Ile
                565                 570                 575

Leu Gly Tyr Cys Ile Gly Thr Ser Ser Phe Ile Cys Ile Pro Thr Tyr
            580                 585                 590

Ile Ala Tyr Arg Leu Ile Ile Thr Pro Gly Thr Phe Lys Glu Arg Ile
        595                 600                 605

Ile Lys Ser Ile Thr Pro Glu Thr Pro Thr Glu Ile Pro Cys Gly Asp
    610                 615                 620

Ile Arg Leu Asn Ala Val
625                 630
```

<210> SEQ ID NO 11
<211> LENGTH: 1893

-continued

```
<212> TYPE: DNA
<213> ORGANISM: Artificial Sequence
<220> FEATURE:
<221> NAME/KEY: CDS
<222> LOCATION: (1)..(1893)
<220> FEATURE:
<223> OTHER INFORMATION: Description of Artificial Sequence:  Synthetic
      Primer

<400> SEQUENCE: 11

atg gag acg acg ccc ttg aat tct cag aag cag cta tca gcg tgt gaa       48
Met Glu Thr Thr Pro Leu Asn Ser Gln Lys Gln Leu Ser Ala Cys Glu
  1               5                  10                  15

gat gga gaa gat tgt cag gaa aac gga gtt cta cag aag gtt gtt ccc       96
Asp Gly Glu Asp Cys Gln Glu Asn Gly Val Leu Gln Lys Val Val Pro
             20                  25                  30

acc cca ggg gac aaa gtg gag tcc ggg caa ata tcc aat ggg tac tca      144
Thr Pro Gly Asp Lys Val Glu Ser Gly Gln Ile Ser Asn Gly Tyr Ser
         35                  40                  45

gca gtt cca agt cct ggt gcg gga gat gac aca cgg cac tct atc cca      192
Ala Val Pro Ser Pro Gly Ala Gly Asp Asp Thr Arg His Ser Ile Pro
     50                  55                  60

gcg acc acc acc acc cta gtg gct gag ctt cat caa ggg gaa cgg gag      240
Ala Thr Thr Thr Thr Leu Val Ala Glu Leu His Gln Gly Glu Arg Glu
 65                  70                  75                  80

acc tgg ggc aag aag gtg gat ttc ctt ctc tca gtg att ggc tat gct      288
Thr Trp Gly Lys Lys Val Asp Phe Leu Leu Ser Val Ile Gly Tyr Ala
                 85                  90                  95

gtg gac ctg ggc aat gtc tgg cgc ttc ccc tac ata tgt tac cag aat      336
Val Asp Leu Gly Asn Val Trp Arg Phe Pro Tyr Ile Cys Tyr Gln Asn
            100                 105                 110

gga ggg ggg gca ttc ctc ctc ccc tac acc atc atg gcc att ttt ggg      384
Gly Gly Gly Ala Phe Leu Leu Pro Tyr Thr Ile Met Ala Ile Phe Gly
        115                 120                 125

gga atc ccg ctc ttt tac atg gag ctc gca ctg gga cag tac cac cga      432
Gly Ile Pro Leu Phe Tyr Met Glu Leu Ala Leu Gly Gln Tyr His Arg
    130                 135                 140

aat gga tgc att tca ata tgg agg aaa atc tgc ccg att ttc aaa ggg      480
Asn Gly Cys Ile Ser Ile Trp Arg Lys Ile Cys Pro Ile Phe Lys Gly
145                 150                 155                 160

att ggt tat gcc atc tgc atc att gcc ttt tac ttt gct tcc tac tac      528
Ile Gly Tyr Ala Ile Cys Ile Ile Ala Phe Tyr Phe Ala Ser Tyr Tyr
                165                 170                 175

aac acc atc atg gcc tgg gcg cta tac tac ctc atc tcc tcc ttc acg      576
Asn Thr Ile Met Ala Trp Ala Leu Tyr Tyr Leu Ile Ser Ser Phe Thr
            180                 185                 190

gac cag ctg ccc tgg acc agc tgc aag aac tcc tgg aac act ggc aac      624
Asp Gln Leu Pro Trp Thr Ser Cys Lys Asn Ser Trp Asn Thr Gly Asn
        195                 200                 205

tgc acc aat tac ttc tcc gag gac aac atc acc tgg acc ctc cat tcc      672
Cys Thr Asn Tyr Phe Ser Glu Asp Asn Ile Thr Trp Thr Leu His Ser
    210                 215                 220

acg tcc cct gct gaa gaa ttt tac acg cgc cac gtc ctg cag atc cac      720
Thr Ser Pro Ala Glu Glu Phe Tyr Thr Arg His Val Leu Gln Ile His
225                 230                 235                 240

cgg tct aag ggg ctc cag gac ctg ggg ggc atc agc tgg cag ctg gcc      768
Arg Ser Lys Gly Leu Gln Asp Leu Gly Gly Ile Ser Trp Gln Leu Ala
                245                 250                 255

ctc tgc atc atg ctg atc ttc act gtt atc tac ttc agc atc tgg aaa      816
Leu Cys Ile Met Leu Ile Phe Thr Val Ile Tyr Phe Ser Ile Trp Lys
            260                 265                 270
```

-continued

```
ggc gtc aag acc tct ggc aag gtg gtg tgg gtg aca gcc acc ttc cct      864
Gly Val Lys Thr Ser Gly Lys Val Val Trp Val Thr Ala Thr Phe Pro
        275                 280                 285

tat atc atc ctt tct gtc ctg ctg gtg agg ggt gcc acc ctc cct gga      912
Tyr Ile Ile Leu Ser Val Leu Leu Val Arg Gly Ala Thr Leu Pro Gly
    290                 295                 300

gcc tgg agg ggt gtt ctc ttc tac ttg aaa ccc aat tgg cag aaa ctc      960
Ala Trp Arg Gly Val Leu Phe Tyr Leu Lys Pro Asn Trp Gln Lys Leu
305                 310                 315                 320

ctg gag aca ggg gtg tgg ata gat gca gcc gct cag atc ttc ttc tct     1008
Leu Glu Thr Gly Val Trp Ile Asp Ala Ala Ala Gln Ile Phe Phe Ser
                325                 330                 335

ctt ggt ccg ggc ttt ggg gtc ctg ctg gct ttt gct agc tac aac aag     1056
Leu Gly Pro Gly Phe Gly Val Leu Leu Ala Phe Ala Ser Tyr Asn Lys
            340                 345                 350

ttc aac aac aac tgc tac caa gat gcc ctg gtg acc agc gtg gtg aac     1104
Phe Asn Asn Asn Cys Tyr Gln Asp Ala Leu Val Thr Ser Val Val Asn
        355                 360                 365

tgc atg acg agc ttc gtt tcg gga ttt gtc atc ttc aca gtg ctc ggt     1152
Cys Met Thr Ser Phe Val Ser Gly Phe Val Ile Phe Thr Val Leu Gly
    370                 375                 380

tac atg gct gag atg agg aat gaa gat gtg tct gag gtg gcc aaa gac     1200
Tyr Met Ala Glu Met Arg Asn Glu Asp Val Ser Glu Val Ala Lys Asp
385                 390                 395                 400

gca ggt ccc agc ctc ctc ttc atc acg tat gca gaa gcg ata gcc aac     1248
Ala Gly Pro Ser Leu Leu Phe Ile Thr Tyr Ala Glu Ala Ile Ala Asn
                405                 410                 415

atg cca gcg tcc act ttc ttt gcc atc atc ttc ttt ctg atg tta atc     1296
Met Pro Ala Ser Thr Phe Phe Ala Ile Ile Phe Phe Leu Met Leu Ile
            420                 425                 430

acg ctg ggc ttg gac agc acg ttt gca ggc ttg gag ggg gtg atc acg     1344
Thr Leu Gly Leu Asp Ser Thr Phe Ala Gly Leu Glu Gly Val Ile Thr
        435                 440                 445

gct gtg ctg gat gag ttc cca cac gtc tgg gcc aag cgc cgg gag cgg     1392
Ala Val Leu Asp Glu Phe Pro His Val Trp Ala Lys Arg Arg Glu Arg
    450                 455                 460

ttc gtg ctc gcc gtg gtc atc acc tgc ttc ttt gga tcc ctg gtc acc     1440
Phe Val Leu Ala Val Val Ile Thr Cys Phe Phe Gly Ser Leu Val Thr
465                 470                 475                 480

ctg act ttt gga ggg gcc tac gtg gtg aag ctg ctg gag gag tat gcc     1488
Leu Thr Phe Gly Gly Ala Tyr Val Val Lys Leu Leu Glu Glu Tyr Ala
                485                 490                 495

acg ggg ccc gca gtg ctc act gtc gcg ctg atc gaa gca gtc gct gtg     1536
Thr Gly Pro Ala Val Leu Thr Val Ala Leu Ile Glu Ala Val Ala Val
            500                 505                 510

tct tgg ttc tat ggc atc act cag ttc tgc agg gac gtg aag gaa atg     1584
Ser Trp Phe Tyr Gly Ile Thr Gln Phe Cys Arg Asp Val Lys Glu Met
        515                 520                 525

ctc ggc ttc agc ccg ggg tgg ttc tgg agg atc tgc tgg gtg gcc atc     1632
Leu Gly Phe Ser Pro Gly Trp Phe Trp Arg Ile Cys Trp Val Ala Ile
    530                 535                 540

agc cct ctg ttt ctc ctg ttc atc att tgc agt ttt ctg atg agc ccg     1680
Ser Pro Leu Phe Leu Leu Phe Ile Ile Cys Ser Phe Leu Met Ser Pro
545                 550                 555                 560

cca caa cta cga ctt ttc caa tat aat tat cct tac tgg agt atc atc     1728
Pro Gln Leu Arg Leu Phe Gln Tyr Asn Tyr Pro Tyr Trp Ser Ile Ile
                565                 570                 575

ttg ggt tac tgc ata gga acc tca tct ttc att tgc atc ccc aca tat     1776
Leu Gly Tyr Cys Ile Gly Thr Ser Ser Phe Ile Cys Ile Pro Thr Tyr
            580                 585                 590
```

-continued

```
ata gct tat cgg ttg atc atc act cca ggg aca ttt aaa gag cgt att      1824
Ile Ala Tyr Arg Leu Ile Ile Thr Pro Gly Thr Phe Lys Glu Arg Ile
        595                 600                 605

att aaa agt att acc cca gaa aca cca aca gaa att cct tgt ggg gac      1872
Ile Lys Ser Ile Thr Pro Glu Thr Pro Thr Glu Ile Pro Cys Gly Asp
    610                 615                 620

atc cgc ttg aat gct gtg taa                                          1893
Ile Arg Leu Asn Ala Val
625                 630


<210> SEQ ID NO 12
<211> LENGTH: 630
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 12

Met Glu Thr Thr Pro Leu Asn Ser Gln Lys Gln Leu Ser Ala Cys Glu
  1               5                  10                  15

Asp Gly Glu Asp Cys Gln Glu Asn Gly Val Leu Gln Lys Val Val Pro
             20                  25                  30

Thr Pro Gly Asp Lys Val Glu Ser Gly Gln Ile Ser Asn Gly Tyr Ser
         35                  40                  45

Ala Val Pro Ser Pro Gly Ala Gly Asp Asp Thr Arg His Ser Ile Pro
     50                  55                  60

Ala Thr Thr Thr Thr Leu Val Ala Glu Leu His Gln Gly Glu Arg Glu
 65                  70                  75                  80

Thr Trp Gly Lys Lys Val Asp Phe Leu Leu Ser Val Ile Gly Tyr Ala
                 85                  90                  95

Val Asp Leu Gly Asn Val Trp Arg Phe Pro Tyr Ile Cys Tyr Gln Asn
            100                 105                 110

Gly Gly Gly Ala Phe Leu Leu Pro Tyr Thr Ile Met Ala Ile Phe Gly
        115                 120                 125

Gly Ile Pro Leu Phe Tyr Met Glu Leu Ala Leu Gly Gln Tyr His Arg
    130                 135                 140

Asn Gly Cys Ile Ser Ile Trp Arg Lys Ile Cys Pro Ile Phe Lys Gly
145                 150                 155                 160

Ile Gly Tyr Ala Ile Cys Ile Ile Ala Phe Tyr Phe Ala Ser Tyr Tyr
                165                 170                 175

Asn Thr Ile Met Ala Trp Ala Leu Tyr Tyr Leu Ile Ser Ser Phe Thr
            180                 185                 190

Asp Gln Leu Pro Trp Thr Ser Cys Lys Asn Ser Trp Asn Thr Gly Asn
        195                 200                 205

Cys Thr Asn Tyr Phe Ser Glu Asp Asn Ile Thr Trp Thr Leu His Ser
    210                 215                 220

Thr Ser Pro Ala Glu Glu Phe Tyr Thr Arg His Val Leu Gln Ile His
225                 230                 235                 240

Arg Ser Lys Gly Leu Gln Asp Leu Gly Gly Ile Ser Trp Gln Leu Ala
                245                 250                 255

Leu Cys Ile Met Leu Ile Phe Thr Val Ile Tyr Phe Ser Ile Trp Lys
            260                 265                 270

Gly Val Lys Thr Ser Gly Lys Val Val Trp Val Thr Ala Thr Phe Pro
        275                 280                 285

Tyr Ile Ile Leu Ser Val Leu Leu Val Arg Gly Ala Thr Leu Pro Gly
```

-continued

```
    290                 295                 300

Ala Trp Arg Gly Val Leu Phe Tyr Leu Lys Pro Asn Trp Gln Lys Leu
305                 310                 315                 320

Leu Glu Thr Gly Val Trp Ile Asp Ala Ala Ala Gln Ile Phe Phe Ser
                325                 330                 335

Leu Gly Pro Gly Phe Gly Val Leu Leu Ala Phe Ala Ser Tyr Asn Lys
            340                 345                 350

Phe Asn Asn Asn Cys Tyr Gln Asp Ala Leu Val Thr Ser Val Val Asn
        355                 360                 365

Cys Met Thr Ser Phe Val Ser Gly Phe Val Ile Phe Thr Val Leu Gly
    370                 375                 380

Tyr Met Ala Glu Met Arg Asn Glu Asp Val Ser Glu Val Ala Lys Asp
385                 390                 395                 400

Ala Gly Pro Ser Leu Leu Phe Ile Thr Tyr Ala Glu Ala Ile Ala Asn
                405                 410                 415

Met Pro Ala Ser Thr Phe Phe Ala Ile Ile Phe Phe Leu Met Leu Ile
            420                 425                 430

Thr Leu Gly Leu Asp Ser Thr Phe Ala Gly Leu Glu Gly Val Ile Thr
        435                 440                 445

Ala Val Leu Asp Glu Phe Pro His Val Trp Ala Lys Arg Arg Glu Arg
    450                 455                 460

Phe Val Leu Ala Val Val Ile Thr Cys Phe Phe Gly Ser Leu Val Thr
465                 470                 475                 480

Leu Thr Phe Gly Gly Ala Tyr Val Val Lys Leu Leu Glu Glu Tyr Ala
                485                 490                 495

Thr Gly Pro Ala Val Leu Thr Val Ala Leu Ile Glu Ala Val Ala Val
            500                 505                 510

Ser Trp Phe Tyr Gly Ile Thr Gln Phe Cys Arg Asp Val Lys Glu Met
        515                 520                 525

Leu Gly Phe Ser Pro Gly Trp Phe Trp Arg Ile Cys Trp Val Ala Ile
    530                 535                 540

Ser Pro Leu Phe Leu Leu Phe Ile Ile Cys Ser Phe Leu Met Ser Pro
545                 550                 555                 560

Pro Gln Leu Arg Leu Phe Gln Tyr Asn Tyr Pro Tyr Trp Ser Ile Ile
                565                 570                 575

Leu Gly Tyr Cys Ile Gly Thr Ser Ser Phe Ile Cys Ile Pro Thr Tyr
            580                 585                 590

Ile Ala Tyr Arg Leu Ile Ile Thr Pro Gly Thr Phe Lys Glu Arg Ile
        595                 600                 605

Ile Lys Ser Ile Thr Pro Glu Thr Pro Thr Glu Ile Pro Cys Gly Asp
    610                 615                 620

Ile Arg Leu Asn Ala Val
625                 630
```

<210> SEQ ID NO 13
<211> LENGTH: 1893
<212> TYPE: DNA
<213> ORGANISM: Artificial Sequence
<220> FEATURE:
<221> NAME/KEY: CDS
<222> LOCATION: (1)..(1893)
<220> FEATURE:
<223> OTHER INFORMATION: Description of Artificial Sequence: Synthetic Primer

<400> SEQUENCE: 13

-continued atg gag acg acg ccc ttg aat tct cag aag cag cta tca gcg tgt gaa 48
Met Glu Thr Thr Pro Leu Asn Ser Gln Lys Gln Leu Ser Ala Cys Glu
1 5 10 15 gat gga gaa gat tgt cag gaa aac gga gtt cta cag aag gtt gtt ccc 96
Asp Gly Glu Asp Cys Gln Glu Asn Gly Val Leu Gln Lys Val Val Pro
20 25 30 acc cca ggg gac aaa gtg gag tcc ggg caa ata tcc aat ggg tac tca 144
Thr Pro Gly Asp Lys Val Glu Ser Gly Gln Ile Ser Asn Gly Tyr Ser
35 40 45 gca gtt cca agt cct ggt gcg gga gat gac aca cgg cac tct atc cca 192
Ala Val Pro Ser Pro Gly Ala Gly Asp Asp Thr Arg His Ser Ile Pro
50 55 60 gcg acc acc acc acc cta gtg gct gag ctt cat caa ggg gaa cgg gag 240
Ala Thr Thr Thr Thr Leu Val Ala Glu Leu His Gln Gly Glu Arg Glu
65 70 75 80 acc tgg ggc aag aag gtg gat ttc ctt ctc tca gtg att ggc tat gct 288
Thr Trp Gly Lys Lys Val Asp Phe Leu Leu Ser Val Ile Gly Tyr Ala
85 90 95 gtg gac ctg ggc aat gtc tgg cgc ttc ccc tac ata tgt tac cag aat 336
Val Asp Leu Gly Asn Val Trp Arg Phe Pro Tyr Ile Cys Tyr Gln Asn
100 105 110 gga ggg ggg gca ttc ctc ctc ccc tac acc atc atg gcc att ttt ggg 384
Gly Gly Gly Ala Phe Leu Leu Pro Tyr Thr Ile Met Ala Ile Phe Gly
115 120 125 gga atc ccg ctc ttt tac atg gag ctc gca ctg gga cag tac cac cga 432
Gly Ile Pro Leu Phe Tyr Met Glu Leu Ala Leu Gly Gln Tyr His Arg
130 135 140 aat gga tgc att tca ata tgg agg aaa atc tgc ccg att ttc aaa ggg 480
Asn Gly Cys Ile Ser Ile Trp Arg Lys Ile Cys Pro Ile Phe Lys Gly
145 150 155 160 att ggt tat gcc atc tgc atc att gcc ttt tac cag gct tcc tac tac 528
Ile Gly Tyr Ala Ile Cys Ile Ile Ala Phe Tyr Gln Ala Ser Tyr Tyr
165 170 175 aac acc atc atg gcc tgg gcg cta tac tac ctc atc tcc tcc ttc acg 576
Asn Thr Ile Met Ala Trp Ala Leu Tyr Tyr Leu Ile Ser Ser Phe Thr
180 185 190 gac cag ctg ccc tgg acc agc tgc aag aac tcc tgg aac act ggc aac 624
Asp Gln Leu Pro Trp Thr Ser Cys Lys Asn Ser Trp Asn Thr Gly Asn
195 200 205 tgc acc aat tac ttc tcc gag gac aac atc acc tgg acc ctc cat tcc 672
Cys Thr Asn Tyr Phe Ser Glu Asp Asn Ile Thr Trp Thr Leu His Ser
210 215 220 acg tcc cct gct gaa gaa ttt tac acg cgc cac gtc ctg cag atc cac 720
Thr Ser Pro Ala Glu Glu Phe Tyr Thr Arg His Val Leu Gln Ile His
225 230 235 240 cgg tct aag ggg ctc cag gac ctg ggg ggc atc agc tgg cag ctg gcc 768
Arg Ser Lys Gly Leu Gln Asp Leu Gly Gly Ile Ser Trp Gln Leu Ala
245 250 255 ctc tgc atc atg ctg atc ttc act gtt atc tac ttc agc atc tgg aaa 816
Leu Cys Ile Met Leu Ile Phe Thr Val Ile Tyr Phe Ser Ile Trp Lys
260 265 270 ggc gtc aag acc tct ggc aag gtg gtg tgg gtg aca gcc acc ttc cct 864
Gly Val Lys Thr Ser Gly Lys Val Val Trp Val Thr Ala Thr Phe Pro
275 280 285 tat atc atc ctt tct gtc ctg ctg gtg agg ggt gcc acc ctc cct gga 912
Tyr Ile Ile Leu Ser Val Leu Leu Val Arg Gly Ala Thr Leu Pro Gly
290 295 300 gcc tgg agg ggt gtt ctc ttc tac ttg aaa ccc aat tgg cag aaa ctc 960
Ala Trp Arg Gly Val Leu Phe Tyr Leu Lys Pro Asn Trp Gln Lys Leu
305 310 315 320

-continued

```
ctg gag aca ggg gtg tgg ata gat gca gcc gct cag atc ttc ttc tct      1008
Leu Glu Thr Gly Val Trp Ile Asp Ala Ala Ala Gln Ile Phe Phe Ser
                325                 330                 335

ctt ggt ccg ggc ttt ggg gtc ctg ctg gct ttt gct agc tac aac aag      1056
Leu Gly Pro Gly Phe Gly Val Leu Leu Ala Phe Ala Ser Tyr Asn Lys
            340                 345                 350

ttc aac aac aac tgc tac caa gat gcc ctg gtg acc agc gtg gtg aac      1104
Phe Asn Asn Asn Cys Tyr Gln Asp Ala Leu Val Thr Ser Val Val Asn
        355                 360                 365

tgc atg acg agc ttc gtt tcg gga ttt gtc atc ttc aca gtg ctc ggt      1152
Cys Met Thr Ser Phe Val Ser Gly Phe Val Ile Phe Thr Val Leu Gly
    370                 375                 380

tac atg gct gag atg agg aat gaa gat gtg tct gag gtg gcc aaa gac      1200
Tyr Met Ala Glu Met Arg Asn Glu Asp Val Ser Glu Val Ala Lys Asp
385                 390                 395                 400

gca ggt ccc agc ctc ctc ttc atc acg tat gca gaa gcg ata gcc aac      1248
Ala Gly Pro Ser Leu Leu Phe Ile Thr Tyr Ala Glu Ala Ile Ala Asn
                405                 410                 415

atg cca gcg tcc act ttc ttt gcc atc atc ttc ttt ctg atg tta atc      1296
Met Pro Ala Ser Thr Phe Phe Ala Ile Ile Phe Phe Leu Met Leu Ile
            420                 425                 430

acg ctg ggc ttg gac agc acg ttt gca ggc ttg gag ggg gtg atc acg      1344
Thr Leu Gly Leu Asp Ser Thr Phe Ala Gly Leu Glu Gly Val Ile Thr
        435                 440                 445

gct gtg ctg gat gag ttc cca cac gtc tgg gcc aag cgc cgg gag cgg      1392
Ala Val Leu Asp Glu Phe Pro His Val Trp Ala Lys Arg Arg Glu Arg
    450                 455                 460

ttc gtg ctc gcc gtg gtc atc acc tgc ttc ttt gga tcc ctg gtc acc      1440
Phe Val Leu Ala Val Val Ile Thr Cys Phe Phe Gly Ser Leu Val Thr
465                 470                 475                 480

ctg act ttt gga ggg gcc tac gtg gtg aag ctg ctg gag gag tat gcc      1488
Leu Thr Phe Gly Gly Ala Tyr Val Val Lys Leu Leu Glu Glu Tyr Ala
                485                 490                 495

acg ggg ccc gca gtg ctc act gtc gcg ctg atc gaa gca gtc gct gtg      1536
Thr Gly Pro Ala Val Leu Thr Val Ala Leu Ile Glu Ala Val Ala Val
            500                 505                 510

tct tgg ttc tat ggc atc act cag ttc tgc agg gac gtg aag gaa atg      1584
Ser Trp Phe Tyr Gly Ile Thr Gln Phe Cys Arg Asp Val Lys Glu Met
        515                 520                 525

ctc ggc ttc agc ccg ggg tgg ttc tgg agg atc tgc tgg gtg gcc atc      1632
Leu Gly Phe Ser Pro Gly Trp Phe Trp Arg Ile Cys Trp Val Ala Ile
    530                 535                 540

agc cct ctg ttt ctc ctg ttc atc att tgc agt ttt ctg atg agc ccg      1680
Ser Pro Leu Phe Leu Leu Phe Ile Ile Cys Ser Phe Leu Met Ser Pro
545                 550                 555                 560

cca caa cta cga ctt ttc caa tat aat tat cct tac tgg agt atc atc      1728
Pro Gln Leu Arg Leu Phe Gln Tyr Asn Tyr Pro Tyr Trp Ser Ile Ile
                565                 570                 575

ttg ggt tac tgc ata gga acc tca tct ttc att tgc atc ccc aca tat      1776
Leu Gly Tyr Cys Ile Gly Thr Ser Ser Phe Ile Cys Ile Pro Thr Tyr
            580                 585                 590

ata gct tat cgg ttg atc atc act cca ggg aca ttt aaa gag cgt att      1824
Ile Ala Tyr Arg Leu Ile Ile Thr Pro Gly Thr Phe Lys Glu Arg Ile
        595                 600                 605

att aaa agt att acc cca gaa aca cca aca gaa att cct tgt ggg gac      1872
Ile Lys Ser Ile Thr Pro Glu Thr Pro Thr Glu Ile Pro Cys Gly Asp
    610                 615                 620

atc cgc ttg aat gct gtg taa                                          1893
Ile Arg Leu Asn Ala Val
```

-continued

```
625                 630

<210> SEQ ID NO 14
<211> LENGTH: 630
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 14

Met Glu Thr Thr Pro Leu Asn Ser Gln Lys Gln Leu Ser Ala Cys Glu
  1               5                  10                  15

Asp Gly Glu Asp Cys Gln Glu Asn Gly Val Leu Gln Lys Val Val Pro
            20                  25                  30

Thr Pro Gly Asp Lys Val Glu Ser Gly Gln Ile Ser Asn Gly Tyr Ser
        35                  40                  45

Ala Val Pro Ser Pro Gly Ala Gly Asp Asp Thr Arg His Ser Ile Pro
     50                  55                  60

Ala Thr Thr Thr Thr Leu Val Ala Glu Leu His Gln Gly Glu Arg Glu
 65                  70                  75                  80

Thr Trp Gly Lys Lys Val Asp Phe Leu Leu Ser Val Ile Gly Tyr Ala
                 85                  90                  95

Val Asp Leu Gly Asn Val Trp Arg Phe Pro Tyr Ile Cys Tyr Gln Asn
            100                 105                 110

Gly Gly Gly Ala Phe Leu Leu Pro Tyr Thr Ile Met Ala Ile Phe Gly
        115                 120                 125

Gly Ile Pro Leu Phe Tyr Met Glu Leu Ala Leu Gly Gln Tyr His Arg
    130                 135                 140

Asn Gly Cys Ile Ser Ile Trp Arg Lys Ile Cys Pro Ile Phe Lys Gly
145                 150                 155                 160

Ile Gly Tyr Ala Ile Cys Ile Ile Ala Phe Tyr Gln Ala Ser Tyr Tyr
                165                 170                 175

Asn Thr Ile Met Ala Trp Ala Leu Tyr Tyr Leu Ile Ser Ser Phe Thr
            180                 185                 190

Asp Gln Leu Pro Trp Thr Ser Cys Lys Asn Ser Trp Asn Thr Gly Asn
        195                 200                 205

Cys Thr Asn Tyr Phe Ser Glu Asp Asn Ile Thr Trp Thr Leu His Ser
    210                 215                 220

Thr Ser Pro Ala Glu Glu Phe Tyr Thr Arg His Val Leu Gln Ile His
225                 230                 235                 240

Arg Ser Lys Gly Leu Gln Asp Leu Gly Gly Ile Ser Trp Gln Leu Ala
                245                 250                 255

Leu Cys Ile Met Leu Ile Phe Thr Val Ile Tyr Phe Ser Ile Trp Lys
            260                 265                 270

Gly Val Lys Thr Ser Gly Lys Val Val Trp Val Thr Ala Thr Phe Pro
        275                 280                 285

Tyr Ile Ile Leu Ser Val Leu Leu Val Arg Gly Ala Thr Leu Pro Gly
    290                 295                 300

Ala Trp Arg Gly Val Leu Phe Tyr Leu Lys Pro Asn Trp Gln Lys Leu
305                 310                 315                 320

Leu Glu Thr Gly Val Trp Ile Asp Ala Ala Ala Gln Ile Phe Phe Ser
                325                 330                 335

Leu Gly Pro Gly Phe Gly Val Leu Leu Ala Phe Ala Ser Tyr Asn Lys
            340                 345                 350
```

-continued

```
Phe Asn Asn Asn Cys Tyr Gln Asp Ala Leu Val Thr Ser Val Val Asn
        355                 360                 365

Cys Met Thr Ser Phe Val Ser Gly Phe Val Ile Phe Thr Val Leu Gly
    370                 375                 380

Tyr Met Ala Glu Met Arg Asn Glu Asp Val Ser Glu Val Ala Lys Asp
385                 390                 395                 400

Ala Gly Pro Ser Leu Leu Phe Ile Thr Tyr Ala Glu Ala Ile Ala Asn
                405                 410                 415

Met Pro Ala Ser Thr Phe Phe Ala Ile Ile Phe Phe Leu Met Leu Ile
            420                 425                 430

Thr Leu Gly Leu Asp Ser Thr Phe Ala Gly Leu Glu Gly Val Ile Thr
        435                 440                 445

Ala Val Leu Asp Glu Phe Pro His Val Trp Ala Lys Arg Arg Glu Arg
    450                 455                 460

Phe Val Leu Ala Val Val Ile Thr Cys Phe Phe Gly Ser Leu Val Thr
465                 470                 475                 480

Leu Thr Phe Gly Gly Ala Tyr Val Val Lys Leu Leu Glu Glu Tyr Ala
                485                 490                 495

Thr Gly Pro Ala Val Leu Thr Val Ala Leu Ile Glu Ala Val Ala Val
            500                 505                 510

Ser Trp Phe Tyr Gly Ile Thr Gln Phe Cys Arg Asp Val Lys Glu Met
        515                 520                 525

Leu Gly Phe Ser Pro Gly Trp Phe Trp Arg Ile Cys Trp Val Ala Ile
    530                 535                 540

Ser Pro Leu Phe Leu Leu Phe Ile Ile Cys Ser Phe Leu Met Ser Pro
545                 550                 555                 560

Pro Gln Leu Arg Leu Phe Gln Tyr Asn Tyr Pro Tyr Trp Ser Ile Ile
                565                 570                 575

Leu Gly Tyr Cys Ile Gly Thr Ser Ser Phe Ile Cys Ile Pro Thr Tyr
            580                 585                 590

Ile Ala Tyr Arg Leu Ile Ile Thr Pro Gly Thr Phe Lys Glu Arg Ile
        595                 600                 605

Ile Lys Ser Ile Thr Pro Glu Thr Pro Thr Glu Ile Pro Cys Gly Asp
    610                 615                 620

Ile Arg Leu Asn Ala Val
625                 630


<210> SEQ ID NO 15
<211> LENGTH: 1893
<212> TYPE: DNA
<213> ORGANISM: Artificial Sequence
<220> FEATURE:
<221> NAME/KEY: CDS
<222> LOCATION: (1)..(1893)
<220> FEATURE:
<223> OTHER INFORMATION: Description of Artificial Sequence:  Synthetic
      Primer

<400> SEQUENCE: 15

atg gag acg acg ccc ttg aat tct cag aag cag cta tca gcg tgt gaa       48
Met Glu Thr Thr Pro Leu Asn Ser Gln Lys Gln Leu Ser Ala Cys Glu
  1               5                  10                  15

gat gga gaa gat tgt cag gaa aac gga gtt cta cag aag gtt gtt ccc       96
Asp Gly Glu Asp Cys Gln Glu Asn Gly Val Leu Gln Lys Val Val Pro
             20                  25                  30

acc cca ggg gac aaa gtg gag tcc ggg caa ata tcc aat ggg tac tca      144
Thr Pro Gly Asp Lys Val Glu Ser Gly Gln Ile Ser Asn Gly Tyr Ser
         35                  40                  45
```

-continued

```
gca gtt cca agt cct ggt gcg gga gat gac aca cgg cac tct atc cca      192
Ala Val Pro Ser Pro Gly Ala Gly Asp Asp Thr Arg His Ser Ile Pro
     50                  55                  60

gcg acc acc acc acc cta gtg gct gag ctt cat caa ggg gaa cgg gag      240
Ala Thr Thr Thr Thr Leu Val Ala Glu Leu His Gln Gly Glu Arg Glu
 65                  70                  75                  80

acc tgg ggc aag aag gtg gat ttc ctt ctc tca gtg att ggc tat gct      288
Thr Trp Gly Lys Lys Val Asp Phe Leu Leu Ser Val Ile Gly Tyr Ala
                 85                  90                  95

gtg gac ctg ggc aat gtc tgg cgc ttc ccc tac ata tgt tac cag aat      336
Val Asp Leu Gly Asn Val Trp Arg Phe Pro Tyr Ile Cys Tyr Gln Asn
            100                 105                 110

gga ggg ggg gca ttc ctc ctc ccc tac acc atc atg gcc att ttt ggg      384
Gly Gly Gly Ala Phe Leu Leu Pro Tyr Thr Ile Met Ala Ile Phe Gly
        115                 120                 125

gga atc ccg ctc ttt tac atg gag ctc gca ctg gga cag tac cac cga      432
Gly Ile Pro Leu Phe Tyr Met Glu Leu Ala Leu Gly Gln Tyr His Arg
    130                 135                 140

aat gga tgc att tca ata tgg agg aaa atc tgc ccg att ttc aaa ggg      480
Asn Gly Cys Ile Ser Ile Trp Arg Lys Ile Cys Pro Ile Phe Lys Gly
145                 150                 155                 160

att ggt tat gcc atc tgc atc att gcc ttt tac gtt gct tcc tac tac      528
Ile Gly Tyr Ala Ile Cys Ile Ile Ala Phe Tyr Val Ala Ser Tyr Tyr
                165                 170                 175

aac acc atc atg gcc tgg gcg cta tac tac ctc atc tcc tcc ttc acg      576
Asn Thr Ile Met Ala Trp Ala Leu Tyr Tyr Leu Ile Ser Ser Phe Thr
            180                 185                 190

gac cag ctg ccc tgg acc agc tgc aag aac tcc tgg aac act ggc aac      624
Asp Gln Leu Pro Trp Thr Ser Cys Lys Asn Ser Trp Asn Thr Gly Asn
        195                 200                 205

tgc acc aat tac ttc tcc gag gac aac atc acc tgg acc ctc cat tcc      672
Cys Thr Asn Tyr Phe Ser Glu Asp Asn Ile Thr Trp Thr Leu His Ser
    210                 215                 220

acg tcc cct gct gaa gaa ttt tac acg cgc cac gtc ctg cag atc cac      720
Thr Ser Pro Ala Glu Glu Phe Tyr Thr Arg His Val Leu Gln Ile His
225                 230                 235                 240

cgg tct aag ggg ctc cag gac ctg ggg ggc atc agc tgg cag ctg gcc      768
Arg Ser Lys Gly Leu Gln Asp Leu Gly Gly Ile Ser Trp Gln Leu Ala
                245                 250                 255

ctc tgc atc atg ctg atc ttc act gtt atc tac ttc agc atc tgg aaa      816
Leu Cys Ile Met Leu Ile Phe Thr Val Ile Tyr Phe Ser Ile Trp Lys
            260                 265                 270

ggc gtc aag acc tct ggc aag gtg gtg tgg gtg aca gcc acc ttc cct      864
Gly Val Lys Thr Ser Gly Lys Val Val Trp Val Thr Ala Thr Phe Pro
        275                 280                 285

tat atc atc ctt tct gtc ctg ctg gtg agg ggt gcc acc ctc cct gga      912
Tyr Ile Ile Leu Ser Val Leu Leu Val Arg Gly Ala Thr Leu Pro Gly
    290                 295                 300

gcc tgg agg ggt gtt ctc ttc tac ttg aaa ccc aat tgg cag aaa ctc      960
Ala Trp Arg Gly Val Leu Phe Tyr Leu Lys Pro Asn Trp Gln Lys Leu
305                 310                 315                 320

ctg gag aca ggg gtg tgg ata gat gca gcc gct cag atc ttc ttc tct     1008
Leu Glu Thr Gly Val Trp Ile Asp Ala Ala Ala Gln Ile Phe Phe Ser
                325                 330                 335

ctt ggt ccg ggc ttt ggg gtc ctg ctg gct ttt gct agc tac aac aag     1056
Leu Gly Pro Gly Phe Gly Val Leu Leu Ala Phe Ala Ser Tyr Asn Lys
            340                 345                 350

ttc aac aac aac tgc tac caa gat gcc ctg gtg acc agc gtg gtg aac     1104
Phe Asn Asn Asn Cys Tyr Gln Asp Ala Leu Val Thr Ser Val Val Asn
```

-continued

```
        355                 360                 365

tgc atg acg agc ttc gtt tcg gga ttt gtc atc ttc aca gtg ctc ggt      1152
Cys Met Thr Ser Phe Val Ser Gly Phe Val Ile Phe Thr Val Leu Gly
    370                 375                 380

tac atg gct gag atg agg aat gaa gat gtg tct gag gtg gcc aaa gac      1200
Tyr Met Ala Glu Met Arg Asn Glu Asp Val Ser Glu Val Ala Lys Asp
385                 390                 395                 400

gca ggt ccc agc ctc ctc ttc atc acg tat gca gaa gcg ata gcc aac      1248
Ala Gly Pro Ser Leu Leu Phe Ile Thr Tyr Ala Glu Ala Ile Ala Asn
                405                 410                 415

atg cca gcg tcc act ttc ttt gcc atc atc ttc ttt ctg atg tta atc      1296
Met Pro Ala Ser Thr Phe Phe Ala Ile Ile Phe Phe Leu Met Leu Ile
            420                 425                 430

acg ctg ggc ttg gac agc acg ttt gca ggc ttg gag ggg gtg atc acg      1344
Thr Leu Gly Leu Asp Ser Thr Phe Ala Gly Leu Glu Gly Val Ile Thr
        435                 440                 445

gct gtg ctg gat gag ttc cca cac gtc tgg gcc aag cgc cgg gag cgg      1392
Ala Val Leu Asp Glu Phe Pro His Val Trp Ala Lys Arg Arg Glu Arg
    450                 455                 460

ttc gtg ctc gcc gtg gtc atc acc tgc ttc ttt gga tcc ctg gtc acc      1440
Phe Val Leu Ala Val Val Ile Thr Cys Phe Phe Gly Ser Leu Val Thr
465                 470                 475                 480

ctg act ttt gga ggg gcc tac gtg gtg aag ctg ctg gag gag tat gcc      1488
Leu Thr Phe Gly Gly Ala Tyr Val Val Lys Leu Leu Glu Glu Tyr Ala
                485                 490                 495

acg ggg ccc gca gtg ctc act gtc gcg ctg atc gaa gca gtc gct gtg      1536
Thr Gly Pro Ala Val Leu Thr Val Ala Leu Ile Glu Ala Val Ala Val
            500                 505                 510

tct tgg ttc tat ggc atc act cag ttc tgc agg gac gtg aag gaa atg      1584
Ser Trp Phe Tyr Gly Ile Thr Gln Phe Cys Arg Asp Val Lys Glu Met
        515                 520                 525

ctc ggc ttc agc ccg ggg tgg ttc tgg agg atc tgc tgg gtg gcc atc      1632
Leu Gly Phe Ser Pro Gly Trp Phe Trp Arg Ile Cys Trp Val Ala Ile
    530                 535                 540

agc cct ctg ttt ctc ctg ttc atc att tgc agt ttt ctg atg agc ccg      1680
Ser Pro Leu Phe Leu Leu Phe Ile Ile Cys Ser Phe Leu Met Ser Pro
545                 550                 555                 560

cca caa cta cga ctt ttc caa tat aat tat cct tac tgg agt atc atc      1728
Pro Gln Leu Arg Leu Phe Gln Tyr Asn Tyr Pro Tyr Trp Ser Ile Ile
                565                 570                 575

ttg ggt tac tgc ata gga acc tca tct ttc att tgc atc ccc aca tat      1776
Leu Gly Tyr Cys Ile Gly Thr Ser Ser Phe Ile Cys Ile Pro Thr Tyr
            580                 585                 590

ata gct tat cgg ttg atc atc act cca ggg aca ttt aaa gag cgt att      1824
Ile Ala Tyr Arg Leu Ile Ile Thr Pro Gly Thr Phe Lys Glu Arg Ile
        595                 600                 605

att aaa agt att acc cca gaa aca cca aca gaa att cct tgt ggg gac      1872
Ile Lys Ser Ile Thr Pro Glu Thr Pro Thr Glu Ile Pro Cys Gly Asp
    610                 615                 620

atc cgc ttg aat gct gtg taa                                          1893
Ile Arg Leu Asn Ala Val
625                 630


<210> SEQ ID NO 16
<211> LENGTH: 630
<212> TYPE: PRT
<213> ORGANISM: Artificial Sequence
<220> FEATURE:
<223> OTHER INFORMATION: Description of Artificial Sequence:  Synthetic
      Peptide
```

-continued

<400> SEQUENCE: 16

```
Met Glu Thr Thr Pro Leu Asn Ser Gln Lys Gln Leu Ser Ala Cys Glu
  1               5                  10                  15

Asp Gly Glu Asp Cys Gln Glu Asn Gly Val Leu Gln Lys Val Val Pro
             20                  25                  30

Thr Pro Gly Asp Lys Val Glu Ser Gly Gln Ile Ser Asn Gly Tyr Ser
         35                  40                  45

Ala Val Pro Ser Pro Gly Ala Gly Asp Asp Thr Arg His Ser Ile Pro
     50                  55                  60

Ala Thr Thr Thr Thr Leu Val Ala Glu Leu His Gln Gly Glu Arg Glu
 65                  70                  75                  80

Thr Trp Gly Lys Lys Val Asp Phe Leu Leu Ser Val Ile Gly Tyr Ala
                 85                  90                  95

Val Asp Leu Gly Asn Val Trp Arg Phe Pro Tyr Ile Cys Tyr Gln Asn
            100                 105                 110

Gly Gly Gly Ala Phe Leu Leu Pro Tyr Thr Ile Met Ala Ile Phe Gly
        115                 120                 125

Gly Ile Pro Leu Phe Tyr Met Glu Leu Ala Leu Gly Gln Tyr His Arg
    130                 135                 140

Asn Gly Cys Ile Ser Ile Trp Arg Lys Ile Cys Pro Ile Phe Lys Gly
145                 150                 155                 160

Ile Gly Tyr Ala Ile Cys Ile Ile Ala Phe Tyr Val Ala Ser Tyr Tyr
                165                 170                 175

Asn Thr Ile Met Ala Trp Ala Leu Tyr Tyr Leu Ile Ser Ser Phe Thr
            180                 185                 190

Asp Gln Leu Pro Trp Thr Ser Cys Lys Asn Ser Trp Asn Thr Gly Asn
        195                 200                 205

Cys Thr Asn Tyr Phe Ser Glu Asp Asn Ile Thr Trp Thr Leu His Ser
    210                 215                 220

Thr Ser Pro Ala Glu Glu Phe Tyr Thr Arg His Val Leu Gln Ile His
225                 230                 235                 240

Arg Ser Lys Gly Leu Gln Asp Leu Gly Gly Ile Ser Trp Gln Leu Ala
                245                 250                 255

Leu Cys Ile Met Leu Ile Phe Thr Val Ile Tyr Phe Ser Ile Trp Lys
            260                 265                 270

Gly Val Lys Thr Ser Gly Lys Val Val Trp Val Thr Ala Thr Phe Pro
        275                 280                 285

Tyr Ile Ile Leu Ser Val Leu Leu Val Arg Gly Ala Thr Leu Pro Gly
    290                 295                 300

Ala Trp Arg Gly Val Leu Phe Tyr Leu Lys Pro Asn Trp Gln Lys Leu
305                 310                 315                 320

Leu Glu Thr Gly Val Trp Ile Asp Ala Ala Ala Gln Ile Phe Phe Ser
                325                 330                 335

Leu Gly Pro Gly Phe Gly Val Leu Leu Ala Phe Ala Ser Tyr Asn Lys
            340                 345                 350

Phe Asn Asn Asn Cys Tyr Gln Asp Ala Leu Val Thr Ser Val Val Asn
        355                 360                 365

Cys Met Thr Ser Phe Val Ser Gly Phe Val Ile Phe Thr Val Leu Gly
    370                 375                 380

Tyr Met Ala Glu Met Arg Asn Glu Asp Val Ser Glu Val Ala Lys Asp
385                 390                 395                 400

Ala Gly Pro Ser Leu Leu Phe Ile Thr Tyr Ala Glu Ala Ile Ala Asn
                405                 410                 415
```

-continued

```
Met Pro Ala Ser Thr Phe Phe Ala Ile Ile Phe Phe Leu Met Leu Ile
            420                 425                 430

Thr Leu Gly Leu Asp Ser Thr Phe Ala Gly Leu Glu Gly Val Ile Thr
        435                 440                 445

Ala Val Leu Asp Glu Phe Pro His Val Trp Ala Lys Arg Arg Glu Arg
    450                 455                 460

Phe Val Leu Ala Val Val Ile Thr Cys Phe Phe Gly Ser Leu Val Thr
465                 470                 475                 480

Leu Thr Phe Gly Gly Ala Tyr Val Val Lys Leu Leu Glu Glu Tyr Ala
                485                 490                 495

Thr Gly Pro Ala Val Leu Thr Val Ala Leu Ile Glu Ala Val Ala Val
            500                 505                 510

Ser Trp Phe Tyr Gly Ile Thr Gln Phe Cys Arg Asp Val Lys Glu Met
        515                 520                 525

Leu Gly Phe Ser Pro Gly Trp Phe Trp Arg Ile Cys Trp Val Ala Ile
    530                 535                 540

Ser Pro Leu Phe Leu Leu Phe Ile Ile Cys Ser Phe Leu Met Ser Pro
545                 550                 555                 560

Pro Gln Leu Arg Leu Phe Gln Tyr Asn Tyr Pro Tyr Trp Ser Ile Ile
                565                 570                 575

Leu Gly Tyr Cys Ile Gly Thr Ser Ser Phe Ile Cys Ile Pro Thr Tyr
            580                 585                 590

Ile Ala Tyr Arg Leu Ile Ile Thr Pro Gly Thr Phe Lys Glu Arg Ile
        595                 600                 605

Ile Lys Ser Ile Thr Pro Glu Thr Pro Thr Glu Ile Pro Cys Gly Asp
    610                 615                 620

Ile Arg Leu Asn Ala Val
625                 630


<210> SEQ ID NO 17
<211> LENGTH: 1893
<212> TYPE: DNA
<213> ORGANISM: Artificial Sequence
<220> FEATURE:
<223> OTHER INFORMATION: Description of Artificial Sequence:  Synthetic
      Primer
<220> FEATURE:
<221> NAME/KEY: CDS
<222> LOCATION: (1)..(1893)

<400> SEQUENCE: 17

atg gag acg acg ccc ttg aat tct cag aag cag cta tca gcg tgt gaa       48
Met Glu Thr Thr Pro Leu Asn Ser Gln Lys Gln Leu Ser Ala Cys Glu
  1               5                  10                  15

gat gga gaa gat tgt cag gaa aac gga gtt cta cag aag gtt gtt ccc       96
Asp Gly Glu Asp Cys Gln Glu Asn Gly Val Leu Gln Lys Val Val Pro
             20                  25                  30

acc cca ggg gac aaa gtg gag tcc ggg caa ata tcc aat ggg tac tca      144
Thr Pro Gly Asp Lys Val Glu Ser Gly Gln Ile Ser Asn Gly Tyr Ser
         35                  40                  45

gca gtt cca agt cct ggt gcg gga gat gac aca cgg cac tct atc cca      192
Ala Val Pro Ser Pro Gly Ala Gly Asp Asp Thr Arg His Ser Ile Pro
     50                  55                  60

gcg acc acc acc acc cta gtg gct gag ctt cat caa ggg gaa cgg gag      240
Ala Thr Thr Thr Thr Leu Val Ala Glu Leu His Gln Gly Glu Arg Glu
 65                  70                  75                  80

acc tgg ggc aag aag gtg gat ttc ctt ctc tca gtg att ggc ttt gct      288
Thr Trp Gly Lys Lys Val Asp Phe Leu Leu Ser Val Ile Gly Phe Ala
```

-continued

```
                85                  90                  95

gtg gac ctg ggc aat gtc tgg cgc ttc ccc tac ata tgt tac cag aat      336
Val Asp Leu Gly Asn Val Trp Arg Phe Pro Tyr Ile Cys Tyr Gln Asn
            100                 105                 110

gga ggg ggg gca ttc ctc ctc ccc tac acc atc atg gcc att ttt ggg      384
Gly Gly Gly Ala Phe Leu Leu Pro Tyr Thr Ile Met Ala Ile Phe Gly
        115                 120                 125

gga atc ccg ctc ttt tac atg gag ctc gca ctg gga cag tac cac cga      432
Gly Ile Pro Leu Phe Tyr Met Glu Leu Ala Leu Gly Gln Tyr His Arg
    130                 135                 140

aat gga tgc att tca ata tgg agg aaa atc tgc ccg att ttc aaa ggg      480
Asn Gly Cys Ile Ser Ile Trp Arg Lys Ile Cys Pro Ile Phe Lys Gly
145                 150                 155                 160

att ggt tat gcc atc tgc atc att gcc ttt tac atg gct tcc tac tac      528
Ile Gly Tyr Ala Ile Cys Ile Ile Ala Phe Tyr Met Ala Ser Tyr Tyr
                165                 170                 175

aac acc atc atg gcc tgg gcg cta tac tac ctc atc tcc tcc ttc acg      576
Asn Thr Ile Met Ala Trp Ala Leu Tyr Tyr Leu Ile Ser Ser Phe Thr
            180                 185                 190

gac cag ctg ccc tgg acc agc tgc aag aac tcc tgg aac act ggc aac      624
Asp Gln Leu Pro Trp Thr Ser Cys Lys Asn Ser Trp Asn Thr Gly Asn
        195                 200                 205

tgc acc aat tac ttc tcc gag gac aac atc acc tgg acc ctc cat tcc      672
Cys Thr Asn Tyr Phe Ser Glu Asp Asn Ile Thr Trp Thr Leu His Ser
    210                 215                 220

acg tcc cct gct gaa gaa ttt tac acg cgc cac gtc ctg cag atc cac      720
Thr Ser Pro Ala Glu Glu Phe Tyr Thr Arg His Val Leu Gln Ile His
225                 230                 235                 240

cgg tct aag ggg ctc cag gac ctg ggg ggc atc agc tgg cag ctg gcc      768
Arg Ser Lys Gly Leu Gln Asp Leu Gly Gly Ile Ser Trp Gln Leu Ala
                245                 250                 255

ctc tgc atc atg ctg atc ttc act gtt atc tac ttc agc atc tgg aaa      816
Leu Cys Ile Met Leu Ile Phe Thr Val Ile Tyr Phe Ser Ile Trp Lys
            260                 265                 270

ggc gtc aag acc tct ggc aag gtg gtg tgg gtg aca gcc acc ttc cct      864
Gly Val Lys Thr Ser Gly Lys Val Val Trp Val Thr Ala Thr Phe Pro
        275                 280                 285

tat atc atc ctt tct gtc ctg ctg gtg agg ggt gcc acc ctc cct gga      912
Tyr Ile Ile Leu Ser Val Leu Leu Val Arg Gly Ala Thr Leu Pro Gly
    290                 295                 300

gcc tgg agg ggt gtt ctc ttc tac ttg aaa ccc aat tgg cag aaa ctc      960
Ala Trp Arg Gly Val Leu Phe Tyr Leu Lys Pro Asn Trp Gln Lys Leu
305                 310                 315                 320

ctg gag aca ggg gtg tgg ata gat gca gcc gct cag atc ttc ttc tct     1008
Leu Glu Thr Gly Val Trp Ile Asp Ala Ala Ala Gln Ile Phe Phe Ser
                325                 330                 335

ctt ggt ccg ggc ttt ggg gtc ctg ctg gct ttt gct agc tac aac aag     1056
Leu Gly Pro Gly Phe Gly Val Leu Leu Ala Phe Ala Ser Tyr Asn Lys
            340                 345                 350

ttc aac aac aac tgc tac caa gat gcc ctg gtg acc agc gtg gtg aac     1104
Phe Asn Asn Asn Cys Tyr Gln Asp Ala Leu Val Thr Ser Val Val Asn
        355                 360                 365

tgc atg acg agc ttc gtt tcg gga ttt gtc atc ttc aca gtg ctc ggt     1152
Cys Met Thr Ser Phe Val Ser Gly Phe Val Ile Phe Thr Val Leu Gly
    370                 375                 380

tac atg gct gag atg agg aat gaa gat gtg tct gag gtg gcc aaa gac     1200
Tyr Met Ala Glu Met Arg Asn Glu Asp Val Ser Glu Val Ala Lys Asp
385                 390                 395                 400

gca ggt ccc agc ctc ctc ttc atc acg tat gca gaa gcg ata gcc aac     1248
```

-continued

```
Ala Gly Pro Ser Leu Leu Phe Ile Thr Tyr Ala Glu Ala Ile Ala Asn
                405                 410                 415

atg cca gcg tcc act ttc ttt gcc atc atc ttc ttt ctg atg tta atc     1296
Met Pro Ala Ser Thr Phe Phe Ala Ile Ile Phe Phe Leu Met Leu Ile
            420                 425                 430

acg ctg ggc ttg gac agc acg ttt gca ggc ttg gag ggg gtg atc acg     1344
Thr Leu Gly Leu Asp Ser Thr Phe Ala Gly Leu Glu Gly Val Ile Thr
        435                 440                 445

gct gtg ctg gat gag ttc cca cac gtc tgg gcc aag cgc cgg gag cgg     1392
Ala Val Leu Asp Glu Phe Pro His Val Trp Ala Lys Arg Arg Glu Arg
    450                 455                 460

ttc gtg ctc gcc gtg gtc atc acc tgc ttc ttt gga tcc ctg gtc acc     1440
Phe Val Leu Ala Val Val Ile Thr Cys Phe Phe Gly Ser Leu Val Thr
465                 470                 475                 480

ctg act ttt gga ggg gcc tac gtg gtg aag ctg ctg gag gag tat gcc     1488
Leu Thr Phe Gly Gly Ala Tyr Val Val Lys Leu Leu Glu Glu Tyr Ala
                485                 490                 495

acg ggg ccc gca gtg ctc act gtc gcg ctg atc gaa gca gtc gct gtg     1536
Thr Gly Pro Ala Val Leu Thr Val Ala Leu Ile Glu Ala Val Ala Val
            500                 505                 510

tct tgg ttc tat ggc atc act cag ttc tgc agg gac gtg aag gaa atg     1584
Ser Trp Phe Tyr Gly Ile Thr Gln Phe Cys Arg Asp Val Lys Glu Met
        515                 520                 525

ctc ggc ttc agc ccg ggg tgg ttc tgg agg atc tgc tgg gtg gcc atc     1632
Leu Gly Phe Ser Pro Gly Trp Phe Trp Arg Ile Cys Trp Val Ala Ile
    530                 535                 540

agc cct ctg ttt ctc ctg ttc atc att tgc agt ttt ctg atg agc ccg     1680
Ser Pro Leu Phe Leu Leu Phe Ile Ile Cys Ser Phe Leu Met Ser Pro
545                 550                 555                 560

cca caa cta cga ctt ttc caa tat aat tat cct tac tgg agt atc atc     1728
Pro Gln Leu Arg Leu Phe Gln Tyr Asn Tyr Pro Tyr Trp Ser Ile Ile
                565                 570                 575

ttg ggt tac tgc ata gga acc tca tct ttc att tgc atc ccc aca tat     1776
Leu Gly Tyr Cys Ile Gly Thr Ser Ser Phe Ile Cys Ile Pro Thr Tyr
            580                 585                 590

ata gct tat cgg ttg atc atc act cca ggg aca ttt aaa gag cgt att     1824
Ile Ala Tyr Arg Leu Ile Ile Thr Pro Gly Thr Phe Lys Glu Arg Ile
        595                 600                 605

att aaa agt att acc cca gaa aca cca aca gaa att cct tgt ggg gac     1872
Ile Lys Ser Ile Thr Pro Glu Thr Pro Thr Glu Ile Pro Cys Gly Asp
    610                 615                 620

atc cgc ttg aat gct gtg taa                                         1893
Ile Arg Leu Asn Ala Val
625                 630


<210> SEQ ID NO 18
<211> LENGTH: 630
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 18

Met Glu Thr Thr Pro Leu Asn Ser Gln Lys Gln Leu Ser Ala Cys Glu
  1               5                  10                  15

Asp Gly Glu Asp Cys Gln Glu Asn Gly Val Leu Gln Lys Val Val Pro
             20                  25                  30

Thr Pro Gly Asp Lys Val Glu Ser Gly Gln Ile Ser Asn Gly Tyr Ser
         35                  40                  45
```

-continued

```
Ala Val Pro Ser Pro Gly Ala Gly Asp Asp Thr Arg His Ser Ile Pro
     50                  55                  60

Ala Thr Thr Thr Thr Leu Val Ala Glu Leu His Gln Gly Glu Arg Glu
 65                  70                  75                  80

Thr Trp Gly Lys Lys Val Asp Phe Leu Leu Ser Val Ile Gly Phe Ala
                 85                  90                  95

Val Asp Leu Gly Asn Val Trp Arg Phe Pro Tyr Ile Cys Tyr Gln Asn
            100                 105                 110

Gly Gly Gly Ala Phe Leu Leu Pro Tyr Thr Ile Met Ala Ile Phe Gly
        115                 120                 125

Gly Ile Pro Leu Phe Tyr Met Glu Leu Ala Leu Gly Gln Tyr His Arg
    130                 135                 140

Asn Gly Cys Ile Ser Ile Trp Arg Lys Ile Cys Pro Ile Phe Lys Gly
145                 150                 155                 160

Ile Gly Tyr Ala Ile Cys Ile Ile Ala Phe Tyr Met Ala Ser Tyr Tyr
                165                 170                 175

Asn Thr Ile Met Ala Trp Ala Leu Tyr Tyr Leu Ile Ser Ser Phe Thr
            180                 185                 190

Asp Gln Leu Pro Trp Thr Ser Cys Lys Asn Ser Trp Asn Thr Gly Asn
        195                 200                 205

Cys Thr Asn Tyr Phe Ser Glu Asp Asn Ile Thr Trp Thr Leu His Ser
    210                 215                 220

Thr Ser Pro Ala Glu Glu Phe Tyr Thr Arg His Val Leu Gln Ile His
225                 230                 235                 240

Arg Ser Lys Gly Leu Gln Asp Leu Gly Gly Ile Ser Trp Gln Leu Ala
                245                 250                 255

Leu Cys Ile Met Leu Ile Phe Thr Val Ile Tyr Phe Ser Ile Trp Lys
            260                 265                 270

Gly Val Lys Thr Ser Gly Lys Val Val Trp Val Thr Ala Thr Phe Pro
        275                 280                 285

Tyr Ile Ile Leu Ser Val Leu Leu Val Arg Gly Ala Thr Leu Pro Gly
    290                 295                 300

Ala Trp Arg Gly Val Leu Phe Tyr Leu Lys Pro Asn Trp Gln Lys Leu
305                 310                 315                 320

Leu Glu Thr Gly Val Trp Ile Asp Ala Ala Ala Gln Ile Phe Phe Ser
                325                 330                 335

Leu Gly Pro Gly Phe Gly Val Leu Leu Ala Phe Ala Ser Tyr Asn Lys
            340                 345                 350

Phe Asn Asn Asn Cys Tyr Gln Asp Ala Leu Val Thr Ser Val Val Asn
        355                 360                 365

Cys Met Thr Ser Phe Val Ser Gly Phe Val Ile Phe Thr Val Leu Gly
    370                 375                 380

Tyr Met Ala Glu Met Arg Asn Glu Asp Val Ser Glu Val Ala Lys Asp
385                 390                 395                 400

Ala Gly Pro Ser Leu Leu Phe Ile Thr Tyr Ala Glu Ala Ile Ala Asn
                405                 410                 415

Met Pro Ala Ser Thr Phe Phe Ala Ile Ile Phe Phe Leu Met Leu Ile
            420                 425                 430

Thr Leu Gly Leu Asp Ser Thr Phe Ala Gly Leu Glu Gly Val Ile Thr
        435                 440                 445

Ala Val Leu Asp Glu Phe Pro His Val Trp Ala Lys Arg Arg Glu Arg
    450                 455                 460

Phe Val Leu Ala Val Val Ile Thr Cys Phe Phe Gly Ser Leu Val Thr
```

-continued

```
465                 470                 475                 480

Leu Thr Phe Gly Gly Ala Tyr Val Val Lys Leu Leu Glu Glu Tyr Ala
                485                 490                 495

Thr Gly Pro Ala Val Leu Thr Val Ala Leu Ile Glu Ala Val Ala Val
            500                 505                 510

Ser Trp Phe Tyr Gly Ile Thr Gln Phe Cys Arg Asp Val Lys Glu Met
        515                 520                 525

Leu Gly Phe Ser Pro Gly Trp Phe Trp Arg Ile Cys Trp Val Ala Ile
    530                 535                 540

Ser Pro Leu Phe Leu Leu Phe Ile Ile Cys Ser Phe Leu Met Ser Pro
545                 550                 555                 560

Pro Gln Leu Arg Leu Phe Gln Tyr Asn Tyr Pro Tyr Trp Ser Ile Ile
                565                 570                 575

Leu Gly Tyr Cys Ile Gly Thr Ser Ser Phe Ile Cys Ile Pro Thr Tyr
            580                 585                 590

Ile Ala Tyr Arg Leu Ile Ile Thr Pro Gly Thr Phe Lys Glu Arg Ile
        595                 600                 605

Ile Lys Ser Ile Thr Pro Glu Thr Pro Thr Glu Ile Pro Cys Gly Asp
    610                 615                 620

Ile Arg Leu Asn Ala Val
625                 630


<210> SEQ ID NO 19
<211> LENGTH: 1893
<212> TYPE: DNA
<213> ORGANISM: Artificial Sequence
<220> FEATURE:
<221> NAME/KEY: CDS
<222> LOCATION: (1)..(1893)
<220> FEATURE:
<223> OTHER INFORMATION: Description of Artificial Sequence:  Synthetic
      Primer

<400> SEQUENCE: 19

atg gag acg acg ccc ttg aat tct cag aag cag cta tca gcg tgt gaa       48
Met Glu Thr Thr Pro Leu Asn Ser Gln Lys Gln Leu Ser Ala Cys Glu
  1               5                  10                  15

gat gga gaa gat tgt cag gaa aac gga gtt cta cag aag gtt gtt ccc       96
Asp Gly Glu Asp Cys Gln Glu Asn Gly Val Leu Gln Lys Val Val Pro
             20                  25                  30

acc cca ggg gac aaa gtg gag tcc ggg caa ata tcc aat ggg tac tca      144
Thr Pro Gly Asp Lys Val Glu Ser Gly Gln Ile Ser Asn Gly Tyr Ser
         35                  40                  45

gca gtt cca agt cct ggt gcg gga gat gac aca cgg cac tct atc cca      192
Ala Val Pro Ser Pro Gly Ala Gly Asp Asp Thr Arg His Ser Ile Pro
     50                  55                  60

gcg acc acc acc acc cta gtg gct gag ctt cat caa ggg gaa cgg gag      240
Ala Thr Thr Thr Thr Leu Val Ala Glu Leu His Gln Gly Glu Arg Glu
 65                  70                  75                  80

acc tgg ggc aag aag gtg gat ttc ctt ctc tca gtg att ggc ttt gct      288
Thr Trp Gly Lys Lys Val Asp Phe Leu Leu Ser Val Ile Gly Phe Ala
                 85                  90                  95

gtg gac ctg ggc aat gtc tgg cgc ttc ccc tac ata tgt tac cag aat      336
Val Asp Leu Gly Asn Val Trp Arg Phe Pro Tyr Ile Cys Tyr Gln Asn
            100                 105                 110

gga ggg ggg gca ttc ctc ctc ccc tac acc atc atg gcc att ttt ggg      384
Gly Gly Gly Ala Phe Leu Leu Pro Tyr Thr Ile Met Ala Ile Phe Gly
        115                 120                 125

gga atc ccg ctc ttt tac atg gag ctc gca ctg gga cag tac cac cga      432
```

-continued

```
Gly Ile Pro Leu Phe Tyr Met Glu Leu Ala Leu Gly Gln Tyr His Arg
    130                 135                 140

aat gga tgc att tca ata tgg agg aaa atc tgc ccg att ttc aaa ggg      480
Asn Gly Cys Ile Ser Ile Trp Arg Lys Ile Cys Pro Ile Phe Lys Gly
145                 150                 155                 160

att ggt tat gcc atc tgc atc att gcc ttt tac att gct tcc tac tac      528
Ile Gly Tyr Ala Ile Cys Ile Ile Ala Phe Tyr Ile Ala Ser Tyr Tyr
                165                 170                 175

aac acc atc atg gcc tgg gcg cta tac tac ctc atc tcc tcc ttc acg      576
Asn Thr Ile Met Ala Trp Ala Leu Tyr Tyr Leu Ile Ser Ser Phe Thr
            180                 185                 190

gac cag ctg ccc tgg acc agc tgc aag aac tcc tgg aac act ggc aac      624
Asp Gln Leu Pro Trp Thr Ser Cys Lys Asn Ser Trp Asn Thr Gly Asn
        195                 200                 205

tgc acc aat tac ttc tcc gag gac aac atc acc tgg acc ctc cat tcc      672
Cys Thr Asn Tyr Phe Ser Glu Asp Asn Ile Thr Trp Thr Leu His Ser
    210                 215                 220

acg tcc cct gct gaa gaa ttt tac acg cgc cac gtc ctg cag atc cac      720
Thr Ser Pro Ala Glu Glu Phe Tyr Thr Arg His Val Leu Gln Ile His
225                 230                 235                 240

cgg tct aag ggg ctc cag gac ctg ggg ggc atc agc tgg cag ctg gcc      768
Arg Ser Lys Gly Leu Gln Asp Leu Gly Gly Ile Ser Trp Gln Leu Ala
                245                 250                 255

ctc tgc atc atg ctg atc ttc act gtt atc tac ttc agc atc tgg aaa      816
Leu Cys Ile Met Leu Ile Phe Thr Val Ile Tyr Phe Ser Ile Trp Lys
            260                 265                 270

ggc gtc aag acc tct ggc aag gtg gtg tgg gtg aca gcc acc ttc cct      864
Gly Val Lys Thr Ser Gly Lys Val Val Trp Val Thr Ala Thr Phe Pro
        275                 280                 285

tat atc atc ctt tct gtc ctg ctg gtg agg ggt gcc acc ctc cct gga      912
Tyr Ile Ile Leu Ser Val Leu Leu Val Arg Gly Ala Thr Leu Pro Gly
    290                 295                 300

gcc tgg agg ggt gtt ctc ttc tac ttg aaa ccc aat tgg cag aaa ctc      960
Ala Trp Arg Gly Val Leu Phe Tyr Leu Lys Pro Asn Trp Gln Lys Leu
305                 310                 315                 320

ctg gag aca ggg gtg tgg ata gat gca gcc gct cag atc ttc ttc tct     1008
Leu Glu Thr Gly Val Trp Ile Asp Ala Ala Ala Gln Ile Phe Phe Ser
                325                 330                 335

ctt ggt ccg ggc ttt ggg gtc ctg ctg gct ttt gct agc tac aac aag     1056
Leu Gly Pro Gly Phe Gly Val Leu Leu Ala Phe Ala Ser Tyr Asn Lys
            340                 345                 350

ttc aac aac aac tgc tac caa gat gcc ctg gtg acc agc gtg gtg aac     1104
Phe Asn Asn Asn Cys Tyr Gln Asp Ala Leu Val Thr Ser Val Val Asn
        355                 360                 365

tgc atg acg agc ttc gtt tcg gga ttt gtc atc ttc aca gtg ctc ggt     1152
Cys Met Thr Ser Phe Val Ser Gly Phe Val Ile Phe Thr Val Leu Gly
    370                 375                 380

tac atg gct gag atg agg aat gaa gat gtg tct gag gtg gcc aaa gac     1200
Tyr Met Ala Glu Met Arg Asn Glu Asp Val Ser Glu Val Ala Lys Asp
385                 390                 395                 400

gca ggt ccc agc ctc ctc ttc atc acg tat gca gaa gcg ata gcc aac     1248
Ala Gly Pro Ser Leu Leu Phe Ile Thr Tyr Ala Glu Ala Ile Ala Asn
                405                 410                 415

atg cca gcg tcc act ttc ttt gcc atc atc ttc ttt ctg atg tta atc     1296
Met Pro Ala Ser Thr Phe Phe Ala Ile Ile Phe Phe Leu Met Leu Ile
            420                 425                 430

acg ctg ggc ttg gac agc acg ttt gca ggc ttg gag ggg gtg atc acg     1344
Thr Leu Gly Leu Asp Ser Thr Phe Ala Gly Leu Glu Gly Val Ile Thr
        435                 440                 445
```

-continued

```
gct gtg ctg gat gag ttc cca cac gtc tgg gcc aag cgc cgg gag cgg     1392
Ala Val Leu Asp Glu Phe Pro His Val Trp Ala Lys Arg Arg Glu Arg
    450                 455                 460

ttc gtg ctc gcc gtg gtc atc acc tgc ttc ttt gga tcc ctg gtc acc     1440
Phe Val Leu Ala Val Val Ile Thr Cys Phe Phe Gly Ser Leu Val Thr
465                 470                 475                 480

ctg act ttt gga ggg gcc tac gtg gtg aag ctg ctg gag gag tat gcc     1488
Leu Thr Phe Gly Gly Ala Tyr Val Val Lys Leu Leu Glu Glu Tyr Ala
                485                 490                 495

acg ggg ccc gca gtg ctc act gtc gcg ctg atc gaa gca gtc gct gtg     1536
Thr Gly Pro Ala Val Leu Thr Val Ala Leu Ile Glu Ala Val Ala Val
            500                 505                 510

tct tgg ttc tat ggc atc act cag ttc tgc agg gac gtg aag gaa atg     1584
Ser Trp Phe Tyr Gly Ile Thr Gln Phe Cys Arg Asp Val Lys Glu Met
        515                 520                 525

ctc ggc ttc agc ccg ggg tgg ttc tgg agg atc tgc tgg gtg gcc atc     1632
Leu Gly Phe Ser Pro Gly Trp Phe Trp Arg Ile Cys Trp Val Ala Ile
    530                 535                 540

agc cct ctg ttt ctc ctg ttc atc att tgc agt ttt ctg atg agc ccg     1680
Ser Pro Leu Phe Leu Leu Phe Ile Ile Cys Ser Phe Leu Met Ser Pro
545                 550                 555                 560

cca caa cta cga ctt ttc caa tat aat tat cct tac tgg agt atc atc     1728
Pro Gln Leu Arg Leu Phe Gln Tyr Asn Tyr Pro Tyr Trp Ser Ile Ile
                565                 570                 575

ttg ggt tac tgc ata gga acc tca tct ttc att tgc atc ccc aca tat     1776
Leu Gly Tyr Cys Ile Gly Thr Ser Ser Phe Ile Cys Ile Pro Thr Tyr
            580                 585                 590

ata gct tat cgg ttg atc atc act cca ggg aca ttt aaa gag cgt att     1824
Ile Ala Tyr Arg Leu Ile Ile Thr Pro Gly Thr Phe Lys Glu Arg Ile
        595                 600                 605

att aaa agt att acc cca gaa aca cca aca gaa att cct tgt ggg gac     1872
Ile Lys Ser Ile Thr Pro Glu Thr Pro Thr Glu Ile Pro Cys Gly Asp
    610                 615                 620

atc cgc ttg aat gct gtg taa                                         1893
Ile Arg Leu Asn Ala Val
625                 630


<210> SEQ ID NO 20
<211> LENGTH: 630
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 20

Met Glu Thr Thr Pro Leu Asn Ser Gln Lys Gln Leu Ser Ala Cys Glu
  1               5                  10                  15

Asp Gly Glu Asp Cys Gln Glu Asn Gly Val Leu Gln Lys Val Val Pro
             20                  25                  30

Thr Pro Gly Asp Lys Val Glu Ser Gly Gln Ile Ser Asn Gly Tyr Ser
         35                  40                  45

Ala Val Pro Ser Pro Gly Ala Gly Asp Asp Thr Arg His Ser Ile Pro
     50                  55                  60

Ala Thr Thr Thr Thr Leu Val Ala Glu Leu His Gln Gly Glu Arg Glu
 65                  70                  75                  80

Thr Trp Gly Lys Lys Val Asp Phe Leu Leu Ser Val Ile Gly Phe Ala
                 85                  90                  95

Val Asp Leu Gly Asn Val Trp Arg Phe Pro Tyr Ile Cys Tyr Gln Asn
            100                 105                 110
```

-continued

```
Gly Gly Gly Ala Phe Leu Leu Pro Tyr Thr Ile Met Ala Ile Phe Gly
        115                 120                 125

Gly Ile Pro Leu Phe Tyr Met Glu Leu Ala Leu Gly Gln Tyr His Arg
    130                 135                 140

Asn Gly Cys Ile Ser Ile Trp Arg Lys Ile Cys Pro Ile Phe Lys Gly
145                 150                 155                 160

Ile Gly Tyr Ala Ile Cys Ile Ile Ala Phe Tyr Ile Ala Ser Tyr Tyr
                165                 170                 175

Asn Thr Ile Met Ala Trp Ala Leu Tyr Tyr Leu Ile Ser Ser Phe Thr
            180                 185                 190

Asp Gln Leu Pro Trp Thr Ser Cys Lys Asn Ser Trp Asn Thr Gly Asn
        195                 200                 205

Cys Thr Asn Tyr Phe Ser Glu Asp Asn Ile Thr Trp Thr Leu His Ser
    210                 215                 220

Thr Ser Pro Ala Glu Glu Phe Tyr Thr Arg His Val Leu Gln Ile His
225                 230                 235                 240

Arg Ser Lys Gly Leu Gln Asp Leu Gly Gly Ile Ser Trp Gln Leu Ala
                245                 250                 255

Leu Cys Ile Met Leu Ile Phe Thr Val Ile Tyr Phe Ser Ile Trp Lys
            260                 265                 270

Gly Val Lys Thr Ser Gly Lys Val Val Trp Val Thr Ala Thr Phe Pro
        275                 280                 285

Tyr Ile Ile Leu Ser Val Leu Leu Val Arg Gly Ala Thr Leu Pro Gly
    290                 295                 300

Ala Trp Arg Gly Val Leu Phe Tyr Leu Lys Pro Asn Trp Gln Lys Leu
305                 310                 315                 320

Leu Glu Thr Gly Val Trp Ile Asp Ala Ala Ala Gln Ile Phe Phe Ser
                325                 330                 335

Leu Gly Pro Gly Phe Gly Val Leu Leu Ala Phe Ala Ser Tyr Asn Lys
            340                 345                 350

Phe Asn Asn Asn Cys Tyr Gln Asp Ala Leu Val Thr Ser Val Val Asn
        355                 360                 365

Cys Met Thr Ser Phe Val Ser Gly Phe Val Ile Phe Thr Val Leu Gly
    370                 375                 380

Tyr Met Ala Glu Met Arg Asn Glu Asp Val Ser Glu Val Ala Lys Asp
385                 390                 395                 400

Ala Gly Pro Ser Leu Leu Phe Ile Thr Tyr Ala Glu Ala Ile Ala Asn
                405                 410                 415

Met Pro Ala Ser Thr Phe Phe Ala Ile Ile Phe Phe Leu Met Leu Ile
            420                 425                 430

Thr Leu Gly Leu Asp Ser Thr Phe Ala Gly Leu Glu Gly Val Ile Thr
        435                 440                 445

Ala Val Leu Asp Glu Phe Pro His Val Trp Ala Lys Arg Arg Glu Arg
    450                 455                 460

Phe Val Leu Ala Val Val Ile Thr Cys Phe Phe Gly Ser Leu Val Thr
465                 470                 475                 480

Leu Thr Phe Gly Gly Ala Tyr Val Val Lys Leu Leu Glu Glu Tyr Ala
                485                 490                 495

Thr Gly Pro Ala Val Leu Thr Val Ala Leu Ile Glu Ala Val Ala Val
            500                 505                 510

Ser Trp Phe Tyr Gly Ile Thr Gln Phe Cys Arg Asp Val Lys Glu Met
        515                 520                 525
```

-continued

```
Leu Gly Phe Ser Pro Gly Trp Phe Trp Arg Ile Cys Trp Val Ala Ile
    530                 535                 540

Ser Pro Leu Phe Leu Leu Phe Ile Ile Cys Ser Phe Leu Met Ser Pro
545                 550                 555                 560

Pro Gln Leu Arg Leu Phe Gln Tyr Asn Tyr Pro Tyr Trp Ser Ile Ile
                565                 570                 575

Leu Gly Tyr Cys Ile Gly Thr Ser Ser Phe Ile Cys Ile Pro Thr Tyr
            580                 585                 590

Ile Ala Tyr Arg Leu Ile Ile Thr Pro Gly Thr Phe Lys Glu Arg Ile
        595                 600                 605

Ile Lys Ser Ile Thr Pro Glu Thr Pro Thr Glu Ile Pro Cys Gly Asp
    610                 615                 620

Ile Arg Leu Asn Ala Val
625                 630
```